(12) United States Patent
Shinohata et al.

(10) Patent No.: US 8,957,241 B2
(45) Date of Patent: Feb. 17, 2015

(54) METHOD FOR PRODUCING CARBONYL COMPOUND

(75) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/821,818

(22) PCT Filed: Feb. 21, 2012

(86) PCT No.: PCT/JP2012/054148
§ 371 (c)(1),
(2), (4) Date: Mar. 8, 2013

(87) PCT Pub. No.: WO2012/115110
PCT Pub. Date: Aug. 30, 2012

(65) Prior Publication Data
US 2013/0178645 A1    Jul. 11, 2013

(30) Foreign Application Priority Data
Feb. 21, 2011    (JP) .................................. 2011-035184

(51) Int. Cl.
| C07C 261/00 | (2006.01) |
| C07C 269/00 | (2006.01) |
| C07C 271/00 | (2006.01) |
| C07C 269/04 | (2006.01) |
| C07C 263/04 | (2006.01) |
| C07C 269/06 | (2006.01) |

(52) U.S. Cl.
CPC ............. C07C 269/04 (2013.01); C07C 263/04 (2013.01); C07C 269/06 (2013.01)
USPC ............................. 560/159; 560/157; 560/345

(58) Field of Classification Search
CPC .... C07C 269/04; C07C 269/06; C07C 263/04
USPC .......................................... 560/159, 157, 345
See application file for complete search history.

(56) References Cited

U.S. PATENT DOCUMENTS

| 2,145,242 | A | 1/1939 | Arnold |
| 2,409,701 | A | 10/1946 | Loth |

(Continued)

FOREIGN PATENT DOCUMENTS

| CA | 2033634 A1 | 7/1991 |
| CA | 2094484 A1 | 10/1993 |

(Continued)

OTHER PUBLICATIONS

Office Action issued in corresponding Chinese Patent Application No. 200980124092.1 dated Dec. 28, 2012.

(Continued)

*Primary Examiner* — Jafar Parsa
*Assistant Examiner* — Amy C Bonaparte
(74) *Attorney, Agent, or Firm* — Morgan, Lewis & Bockius LLP

(57) ABSTRACT

A method for producing a carbonyl compound of the present invention comprises a step (X) of reacting a specific compound having a urea bond with a carbonic acid derivative having a carbonyl group (—C(=O)—) under heating at a temperature equal to or higher than the thermal dissociation temperature of the urea bond to obtain the carbonyl compound.

29 Claims, 4 Drawing Sheets

(56) References Cited

U.S. PATENT DOCUMENTS

| | | | |
|---|---|---|---|
| 2,409,712 A | | 10/1946 | Schweitzer |
| 2,677,698 A | | 5/1954 | Deutschman, Jr. et al. |
| 2,692,275 A | | 10/1954 | Bortnick |
| 3,466,346 A | * | 9/1969 | Perga et al. ............... 203/58 |
| 3,734,941 A | | 5/1973 | Sydor |
| 3,873,553 A | | 3/1975 | Hearsey |
| 3,992,430 A | | 11/1976 | Bacskai |
| 4,081,472 A | | 3/1978 | Tsumura et al. |
| 4,097,676 A | | 6/1978 | Romano |
| 4,290,970 A | | 9/1981 | Merger et al. |
| 4,297,501 A | | 10/1981 | Becker et al. |
| 4,381,404 A | * | 4/1983 | Buysch et al. ............... 560/24 |
| 4,388,238 A | | 6/1983 | Heitkamper et al. |
| 4,388,246 A | | 6/1983 | Sundermann et al. |
| 4,388,426 A | | 6/1983 | Schure et al. |
| 4,430,505 A | | 2/1984 | Heitkamper et al. |
| 4,480,110 A | * | 10/1984 | Heitkamper et al. ......... 549/467 |
| 4,482,499 A | | 11/1984 | Merger et al. |
| 4,497,963 A | | 2/1985 | Merger et al. |
| 4,514,339 A | | 4/1985 | Romano et al. |
| 4,611,079 A | | 9/1986 | Merger et al. |
| 4,692,550 A | | 9/1987 | Engbert et al. |
| 4,713,476 A | | 12/1987 | Merger et al. |
| 4,925,971 A | * | 5/1990 | Aoki et al. ............... 560/137 |
| 5,087,739 A | | 2/1992 | Bohmholdt et al. |
| 5,360,931 A | | 11/1994 | Bohmholdt et al. |
| 5,386,053 A | | 1/1995 | Otterbach et al. |
| 5,744,633 A | | 4/1998 | Wilmes et al. |
| 7,122,697 B2 | | 10/2006 | Yoshida et al. |
| 2010/0029981 A1 | | 2/2010 | Shinohata et al. |
| 2010/0036154 A1 | | 2/2010 | Michalczak et al. |
| 2010/0069665 A1 | | 3/2010 | Shinohata et al. |
| 2010/0113823 A1 | | 5/2010 | Shinohata et al. |
| 2010/0274046 A1 | | 10/2010 | Kloetzer et al. |
| 2013/0178643 A1 | | 7/2013 | Shinohata et al. |

FOREIGN PATENT DOCUMENTS

| | | |
|---|---|---|
| CA | 2707336 A1 | 2/2011 |
| CN | 101234998 A | 8/2008 |
| CN | 101374802 A | 2/2009 |
| DE | 1042891 B | 11/1958 |
| DE | 3928595 A1 | 3/1991 |
| EP | 0355443 A2 | 2/1990 |
| EP | 0566925 A2 | 10/1993 |
| EP | 0568782 A2 | 11/1993 |
| EP | 0657420 A1 | 6/1995 |
| JP | 52-071443 A | 6/1977 |
| JP | 56-103152 A | 8/1981 |
| JP | 56-103153 A | 8/1981 |
| JP | 57-091967 A | 6/1982 |
| JP | 57-112363 A | 7/1982 |
| JP | 59-108754 A | 6/1984 |
| JP | 01-203356 A | 8/1989 |
| JP | 02-000262 A | 1/1990 |
| JP | 2000759 A | 1/1990 |
| JP | 03-020254 A | 1/1991 |
| JP | 03-184947 A | 8/1991 |
| JP | 04-164060 A | 6/1992 |
| JP | 04-221359 A | 8/1992 |
| JP | 05-310677 A | 11/1993 |
| JP | 06-041045 A | 2/1994 |
| JP | 06-192204 A | 7/1994 |
| JP | 06-239826 A | 8/1994 |
| JP | 07-157463 A | 6/1995 |
| JP | 08-109118 A | 4/1996 |
| JP | 08-277255 A | 10/1996 |
| JP | 08-277257 A | 10/1996 |
| JP | 09-255630 A | 9/1997 |
| JP | 2804132 B2 | 7/1998 |
| JP | 2804232 B2 | 7/1998 |
| JP | 3382289 B2 | 12/2002 |
| JP | 2009-502792 A | 1/2009 |
| TW | 200930693 A | 7/2009 |
| WO | 2008/059953 A1 | 5/2008 |
| WO | 2008/084824 A1 | 7/2008 |
| WO | 2008/120645 A1 | 10/2008 |

OTHER PUBLICATIONS

Search Report issued in International Patent Application No. PCT/JP2012/054148 dated May 15, 2012.

Office Action issued in corresponding Japanese Patent Application No. 2012-088122 dated Jun. 1, 2012.

Office Action issued in corresponding Canadian Patent Application No. 2707336 dated Feb. 27, 2012.

Office Action issued in corresponding Taiwanese Patent Application No. 098134456 dated Apr. 13, 2012.

Office Action issued in corresponding Japanese Patent Application No. 2010-539966 dated Feb. 23, 2010.

Hofmann, "Ueber die aromatischen Cyanate," Berchte der Deutechen Chemischen Gescellschaft, 3: 653-658 (1870).

Schiff, "Berchte der Deutechen Chemischen," Gesellschaft, 3:649-652 (1870).

Dyer et al., "Thermal Degradation of Alkyl N-Phenylcarbamates," Journal of the American Chemical Society, 81: 2138-2143 (1959).

Bayer, "Das Diisocyanat-Polyadditionsverfahren," 1963.

Miyake, Reactions of Amines with Urea and its Derivatives, III, Reactions of Urea with Diamines, Journal of Synthetic Organic Chemistry, 20: 1003-1008 (1962) (with English abstract).

"Yukikagaku Seikagaku Meimeihous" Organic Chemistry and Biochemistry Nomenclature (2nd revision published in Japan in 1992 by Nankodo Co., Ltd).

Recommendations 1993, "IUPAC Nomenclature of Organic Chemistry," Advanced Chemistry Development, Inc.

Recommendations 1979, "IUPAC Nomenclature of Organic Chemistry," Advanced Chemistry Development, Inc.

Katchalski et al., "The Chemical Structure of Some Diamine Carbamates," Journal of American Chemical Society, 73: 1829-1831 (1951).

Gittos et al., "A New Synthesis of Isocyanates," Journal of the Chemical Society, Perkin Transactions I: Organic and Bio-Organic Chemistry, 141-143 (1976).

Harris et al., "Thermal oligomerization of N,N-(1,6-hexanediyl)bisurea," Polymer, 35: 3766-3768 (1994).

Yadav et al., "Three-Component Coupling Strategy for Expeditious Synthesis of 4-Aminobenzoxazinones on Mineral Support," Synlett, No. 20: 3055-3058 (2005).

Stedman et al., "The Methylurethanes of the Isomeric a-Hydroxyphenylethyldimethylamines and their Miotic Activity," Journal of the Chemical Society, 609-617 (1929).

Office Action issued in related U.S. Appl. No. 13/001,238 dated Apr. 29, 2013.

Office Action issued in related U.S. Appl. No. 12/810,668 dated Jan. 3, 2013.

Office Action issued in corresponding Chinese Patent Application No. 200980160125.8 dated May 22, 2013.

Office Action issued in corresponding Taiwanese Patent Application No. 101105787 dated Oct. 17, 2013.

* cited by examiner

METHOD FOR PRODUCING CARBONYL COMPOUND

TECHNICAL FIELD

The present invention relates to a method for producing a carbonyl compound, especially, a method for producing an N-substituted carbamic acid ester, and a method for producing an isocyanate using the N-substituted carbamic acid ester.

BACKGROUND ART

It has been known from long ago that an isocyanate and a hydroxy compound can be obtained by the pyrolysis of an N-substituted carbamic acid ester. The basic reaction thereof is represented by the following formulae (a) and (b):

(a)

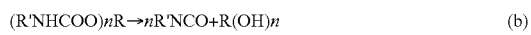
(b)

wherein
R represents an n-valent organic residue, R' represents a monovalent organic residue, and n represents an integer of 1 or greater.

Various studies have been conducted so far, regarding a method for producing an N-substituted carbamic acid ester that is used as a raw material.

For example, Patent Document 1 describes a method comprising reacting a primary diamine and alcohol with urea or a carbonic acid derivative in the presence of a catalyst to convert them to an N-substituted carbamic acid ester. In addition, Patent Document 2 describes a method comprising producing bisurea from an aliphatic primary polyamine, urea and alcohol, and then producing an N-substituted carbamic acid ester from the bisurea. Moreover, Patent Document 3 describes a method comprising partially reacting urea with alcohol in a first step and then supplying a diamine to the reaction product in the second step to produce an N-substituted carbamic acid ester.

LIST OF PRIOR ART DOCUMENTS

Patent Document

[Patent Document 1] U.S. Pat. No. 4,713,476
[Patent Document 2] European Patent Application Laid-Open No. 0568782
[Patent Document 3] European Patent Application Laid-Open No. 0657420

SUMMARY OF INVENTION

Problems to be Solved by Invention

The reaction formula of an N-substituted carbamic acid ester produced from a primary amine, urea and alcohol used as raw materials, is represented by the following formula (i):
Initial-stage Reaction

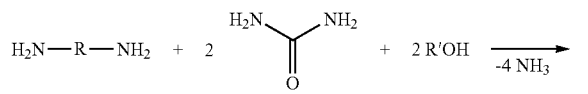
(i)

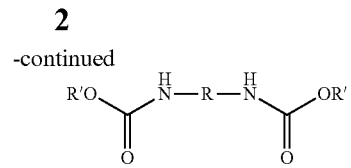

At the initial stage of the reaction, a sufficient amount of urea is present with respect to the primary amine. However, at the late stage of the reaction, the concentrations of both of the substances (the primary amine and the urea) decrease, and the N-substituted carbamic acid ester is present in a high concentration. The cationicity of carbonyl carbon in the urea or carbonic acid derivative is low (since electrons are donated from an $NH_2$ group or an alkoxy group). Moreover, the difference in reactivity between the carbonyl carbon of the N-substituted carbamic acid ester as a product and the primary amine is small. Accordingly, unless a largely excessive amount of urea is present with respect to the primary amine, a reaction as shown in the following formula (ii) will progress at the late stage of the reaction.

Late-stage Reaction: Reaction with N-substituted Carbamic Acid Ester

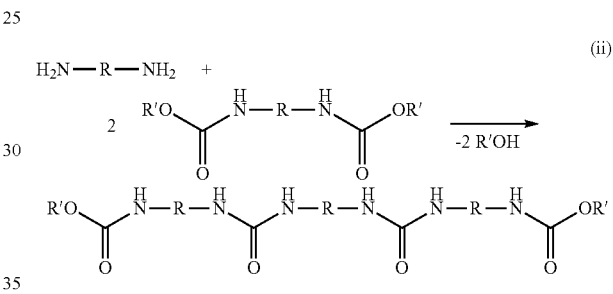
(ii)

Specifically, the primary amine reacts with the N-substituted carbamic acid ester as a product, so that it degenerates to an undesired compound having an N,N-disubstituted urea bond. In a case in which a polyamine is used, since each amino group successively reacts, reactions for generating various degenerated products other than that shown in the above formula (ii) may occur. Examples of such reactions include a reaction of generating an isocyanate according to the following formula (iii) and a reaction of the generated isocyanate with urea according to the following formula (iv). It is considered that, as the N-substituted carbamic acid ester is accumulated and the concentration of the urea is decreased, such reactions of generating these degenerated products extremely easily progress.

Late-stage Reaction: Generation of Isocyanate

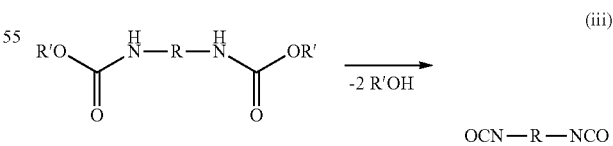
(iii)

Late-stage Reaction: Reaction with Isocyanate

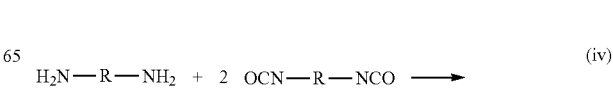
(iv)

-continued

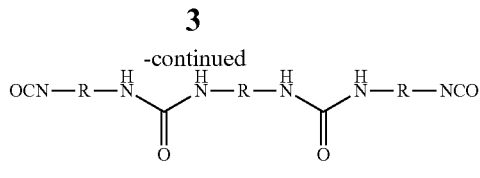

Naturally, on the bases of the principles of the formula (ii), formula (iii), and formula (iv), high-molecular-weight products, which are further polymerized, are also generated. These compounds each having an N,N'-disubstituted urea bond, which are generated as a result of the degeneration, have low reactivity, and thus, it is difficult to re-add the dissociated alcohol. Such a reaction of re-adding alcohol may occur at a high temperature. In a high temperature range, however, an isocyanate begins to be generated as a result of the pyrolysis of the N-substituted carbamic acid ester, and it results in causing a wider variety of side reactions.

Since a high-molecular-weight product generated as a result of the above described reaction has extremely low solubility in a solvent or the like, there are many cases in which adhesion of the high-molecular-weight product to a reaction vessel, solidification of the high-molecular-weight product, and the like occur. Accordingly, the conventional method for producing the N-substituted carbamic acid ester is not considered to be an industrially satisfactory method. In order to overcome such a problem, a method comprising producing bisurea from a primary amine, urea and alcohol, and then reacting the bisurea with alcohol to produce an N-substituted carbamic acid ester, which is as described in Patent Document 2 or the like, has been studied. However, this method has not yet overcome the above described problem that occurs upon production of the N-substituted carbamic acid ester.

Means for Solving Problems

Hence, as a result of intensive studies directed towards overcoming the aforementioned problem, the present inventors have found that the above described problem can be overcome by a method for producing a carbonyl compound, comprising reacting a specific compound having a urea bond with a carbonic acid derivative under heating at a temperature equal to or higher than the thermal dissociation temperature of the urea bond of the specific compound. Moreover, the inventors have also found that the above described problem can be overcome by a method for producing an N-substituted carbamic acid ester from an organic primary amine, a hydroxy compound, and a carbonic acid derivative used as raw materials, comprising reacting a specific compound having a urea bond with a carbonic acid derivative under heating at a temperature equal to or higher than the thermal dissociation temperature of the urea bond of the specific compound, thereby completing the present invention.

Specifically, the present invention is as follows.

[1]

A method for producing a carbonyl compound, comprising a step (X) of reacting a compound having a urea bond represented by a formula (1) as shown below with a carbonic acid derivative having a carbonyl group (—C(=O)—) under heating at a temperature equal to or higher than the thermal dissociation temperature of the urea bond to obtain the carbonyl compound:

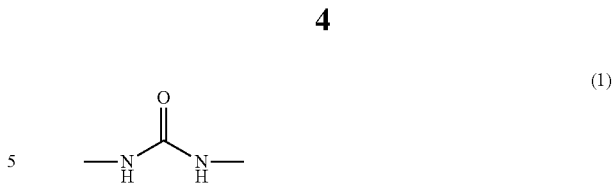

[2]

The method for producing the carbonyl compound according to [1] above, wherein the step (X) is carried out in the coexistence of a hydroxy compound.

[3]

The method for producing the carbonyl compound according to [1] or [2] above, wherein the carbonyl compound comprises an N-substituted carbamic acid ester.

[4]

The method for producing the carbonyl compound according to any one of [1] to [3] above, wherein the carbonic acid derivative is urea or an N-unsubstituted carbamic acid ester.

[5]

The method for producing the carbonyl compound according to any one of [1] to [3] above, wherein the carbonic acid derivative is a carbonic acid ester.

[6]

The method for producing the carbonyl compound according to any one of [1] to [5] above, wherein the compound having the urea bond is a compound represented by a formula (2) as shown below, which is produced from raw material ingredients comprising an organic primary amine and a carbonic acid derivative:

wherein $R^1$ and $R^2$ each independently represent an organic group comprising a group derived from the organic primary amine.

[7]

The method for producing the carbonyl compound according to any one of [1] to [5] above, wherein the compound having the urea bond is a polyurethane-urea copolymer.

[8]

The method for producing the carbonyl compound according to [1] above, wherein the carbonic acid derivative is a phosgene, and the carbonyl compound comprises a compound having a group represented by the following formula (3):

[9]

The method for producing the carbonyl compound according to [8] above, wherein the compound having the urea bond is a compound produced from an organic primary amine and a phosgene.

[10]
The method for producing the carbonyl compound according to any one of [1] to [9] above, wherein the step (X) is carried out in a distillation column.

[11]
A method for producing an isocyanate, comprising a step of subjecting a carbonyl compound obtained by the production method according to any one of [1] to [10] above to a pyrolytic reaction to produce the isocyanate.

[12]
The method for producing the carbonyl compound according to any one of [1] to [10] above, wherein
the step (X) is carried out using a distillation column comprising a supply port A, a supply port B, and a discharge port C;
the step (X) comprises steps of:
supplying raw material ingredients comprising the compound having the urea bond, or raw material ingredients comprising a precursor of the compound having the urea bond, to the distillation column via at least one supply port A,
supplying the carbonic acid derivative to the distillation column via at least one supply port B, and
recovering a generated mixture comprising a carbonyl compound via at least one discharge port C disposed at a lower part of the distillation column; and
the at least one supply port B is disposed at a position the same as or lower than the supply port A,
the at least one discharge port C is disposed at a position the same as or lower than the supply port B, and
a temperature of the distillation column at a height of the supply port B is equal to or higher than the thermal dissociation temperature of the urea bond in the compound having the urea bond.

[13]
The method for producing the carbonyl compound according to [12] above, wherein the precursors of the compound having the urea bond are an organic primary amine and a carbonic acid derivative.

[14]
The method for producing the carbonyl compound according to [12] above, wherein the precursor of the compound having the urea bond is a compound having a ureido group represented by the following formula (4):

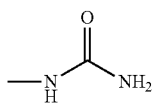

(4)

[15]
The method for producing the carbonyl compound according to any one of [12] to [14] above, wherein the raw material ingredients to be supplied via the supply port A further comprise hydroxy compound.

[16]
The method for producing the carbonyl compound according to [12] above, wherein
the raw material ingredients to be supplied via the supply port A are indicated by a combination (i) or (ii) described below, and
the mixture to be recovered via the discharge port C comprises an N-substituted carbamic acid ester and a hydroxy compound:
combination (i): an organic primary amine, urea, and a hydroxy compound; or
combination (ii): a hydroxy compound and a compound having a ureido group represented by the following formula (4):

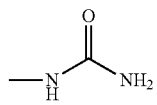

(4)

[17]
The method for producing the carbonyl compound according to [12] above, wherein
the raw material ingredients to be supplied via the supply port A are indicated by combination (iii): an organic primary amine, a carbonic acid ester, and a hydroxy compound, and
the mixture to be recovered via the discharge port C comprises an N-substituted carbamic acid ester and a hydroxy compound.

[18]
The method for producing the carbonyl compound according to [12] above, wherein
the raw material ingredients to be supplied via the supply port A are indicated by combination (iv): a polyurethane-urea copolymer and a hydroxy compound, and
the mixture to be recovered via the discharge port C comprises an N-substituted carbamic acid ester and a hydroxy compound.

[19]
The method for producing the carbonyl compound according to any one of [12] to [18] above, wherein a hydroxy compound is further supplied to the distillation column via the supply port B.

[20]
The method for producing the carbonyl compound according to any one of [12] to [19] above, wherein
the distillation column comprises a plurality of the supply ports B, and
a mixture of a carbonic acid derivative and a hydroxy compound is supplied to the distillation column via the plurality of supply ports B.

[21]
The method for producing the carbonyl compound according to [12] above, wherein
the distillation column further comprises a condenser;
the method further comprises a step of condensing a portion of gas discharged from a top of the distillation column using the condenser to obtain a condensate;
a hydroxy compound is further supplied to the distillation column via the supply port A and/or the supply port B;
the carbonic acid derivative to be supplied via the supply port B is urea and/or an N-unsubstituted carbamic acid ester;
the gas discharged from the top of the distillation column comprises a compound having a carbonyl group derived from the carbonic acid derivative and/or a compound having a carbonyl group derived from the compound having the urea bond, a hydroxy compound, and ammonia; and
the condensate comprises a compound having a carbonyl group and a hydroxy compound.

[22]
The method for producing the carbonyl compound according to [21] above, wherein a part of or an entire condensate is circulated inside the distillation column.

[23]
The method for producing the carbonyl compound according to [21] above, wherein a part of or an entire condensate is supplied to the distillation column via the supply port B.

[24]

The method for producing the carbonyl compound according to [21] above, wherein a part of or an entire condensate is recycled as a raw material ingredient for producing a compound having a ureido group represented by the following formula (4):

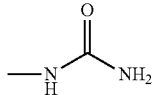
(4)

[25]

The method for producing the carbonyl compound according to [21] above, further comprising a step of reacting the ammonia comprised in the gas discharged from the top of the distillation column with carbon dioxide to produce urea, the urea being recycled.

[26]

The method for producing the carbonyl compound according to any one of [6], [9], [13], [16], and [17]above, wherein the organic primary amine is a compound represented by the following formula (5):

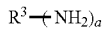
(5)

wherein $R^3$ represents an organic group containing 1 to 85 carbon atoms, and a represents an integer from 1 to 10.

[27]

The method for producing the carbonyl compound according to any one of [2] and [15] to [21] above, wherein the hydroxy compound is an aromatic hydroxy compound, and the carbonyl compound comprises an N-substituted carbamic acid-O-aryl ester represented by the following formula (6):

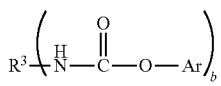
(6)

wherein $R^3$ represents an organic group containing 1 to 85 carbon atoms,

Ar represents a group derived from an aromatic hydroxy compound, which is a residue obtained by removing one hydroxy group from the aromatic hydroxy compound, and b represents an integer from 1 to 10.

[28]

The method for producing the carbonyl compound according to any one of [2] and [15] to [21] above, wherein the hydroxy compound is alcohol, and the carbonyl compound comprises an N-substituted carbamic acid-O-alkyl ester represented by the following formula (7):

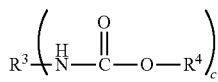
(7)

wherein $R^3$ represents an organic group containing 1 to 85 carbon atoms, $R^4$ represents a group derived from alcohol, which is a residue obtained by removing one hydroxy group from the alcohol, and c represents an integer from 1 to 10.

[29]

The method for producing the carbonyl compound according to [28] above, further comprising a step of reacting the N-substituted carbamic acid-O-alkyl ester with an aromatic hydroxy compound to obtain an N-substituted carbamic acid-O-aryl ester represented by the following formula (6) and alcohol:

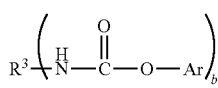
(6)

wherein $R^3$ represents an organic group containing 1 to 85 carbon atoms,

Ar represents a group derived from an aromatic hydroxy compound, which is a residue obtained by removing one hydroxy group from the aromatic hydroxy compound, and b represents an integer from 1 to 10.

[30]

A method for producing an isocyanate, comprising a step of subjecting an N-substituted carbamic acid-O-aryl ester obtained by the production method according to [27] or [29] above to a pyrolytic reaction to obtain a product comprising an isocyanate and an aromatic hydroxy compound.

[31]

The method for producing the carbonyl compound according to any one of [2] and [15] to [21] above, wherein the hydroxy compound is alcohol obtained by the production method according to [29] above.

[32]

The method for producing the carbonyl compound according to any one of [2], [15] to [21], and [29] above, wherein the hydroxy compound or the aromatic hydroxy compound is an aromatic hydroxy compound obtained by the production method according to [30] above.

[33]

The method for producing an isocyanate according to [30] above, further comprising a step of separating the product obtained by the pyrolytic reaction into a gaseous phase ingredient and a liquid phase ingredient and then recovering a part of or an entire liquid phase ingredient, wherein the liquid phase ingredient comprises a compound having a urea bond.

[34]

The method for producing the carbonyl compound according to [1] above, wherein the compound having the urea bond is a compound having a urea bond comprised in the liquid phase ingredient obtained by the production method according to [33] above.

Advantages of Invention

According to the method for producing the carbonyl compound of the present embodiment, a compound having a carbonyl group derived from a carbonic acid derivative can be efficiently produced from a compound having a urea bond and a carbonic acid derivative. In particular, since a compound having a urea bond obtained as a by-product can be converted to an N-substituted carbamic acid ester in a method for producing an N-substituted carbamic acid ester, such an N-substituted carbamic acid ester that is preferably used in the production of an isocyanate can be produced at a high yield. In addition, a carbonic acid derivative that has been excessively used in the reaction can be recovered and recycled, so that an N-substituted carbamic acid ester can be further efficiently produced without impairing the amounts of a carbonic acid derivative and an organic primary amine used.

MODE FOR CARRYING OUT INVENTION

Figure 1:
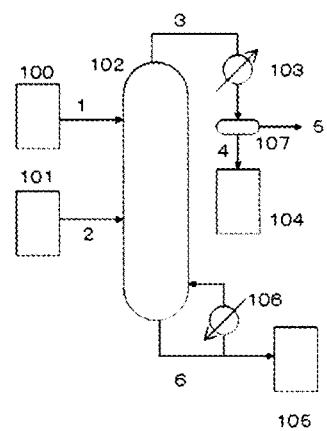
FIG. 1 is a schematic view showing an example of the reaction apparatus used in the production method of the present embodiment.

Hereinafter, the embodiment for carrying out the present invention (hereinafter referred to as "the present embodiment") will be described in detail. It is to be noted that the present invention is not limited to the following embodiment, and that it can be carried out in various modified forms within the range of the gist thereof.

<<Nomenclature of Compounds Used in the Present Embodiment, Etc.>>

First of all, the nomenclature of compounds used in the present embodiment, etc. will be described.

In the present specification, as compound names, names that are based on the regulations described in the Nomenclature (IUPAC Nomenclature of Organic Chemistry) defined by IUPAC (The International Union of Pure and Applied Chemistry) are used in many cases. The aforementioned regulations are based on Recommendations on Organic & Biochemical Nomenclature. Hereinafter, when the IUPAC regulations, and the Nomenclature regulations defined by IUPAC (except for the case of particularly citing IUPAC recommendation in other business years, etc.) are applied in the present application, there is cited "Yuki Kagaku/Seikagaku Meimeihou (Nomenclature of Organic Chemistry/Biochemistry)" (Nankodo Co., Ltd., Japan, Revised $2^{nd}$ edition, 1992), which is based on "Edition 1980" that is on the basis of Recommendations 1979 and includes all of the regulations for organic chemistry and biochemistry and the regulations regarding translation into Japanese, published as a supplementary volume of "Kagaku no Ryoiki (Field of Chemistry)," and which includes all of the subsequent revisions and recommendations. The term "organic" is used herein to mean a general group of compounds that are considered as targets of the nomenclature disclosed in the aforementioned publication. The targets may be the same as those described in the recommendations published in 1993. However, the "organic" compound as a target of the above described Nomenclature also includes organic metal compounds and metal complexes. In the present embodiment, "organic" and/or "organic groups" and/or "substituents," as well as the compounds used in the present embodiment will be described below. Such compounds are constituted with atoms excluding metal atoms and/or semi-metal atoms, unless otherwise specified. More preferably, "organic compounds," "organic groups," and "substituents" that are constituted with atoms selected from among H (hydrogen atom), C (carbon atom), N (nitrogen atom), O (oxygen atom), S (sulfur atom), Cl (chlorine atom), Br (bromine atom), and I (iodine atom), are used in the present embodiment.

Moreover, in the subsequent descriptions, the terms "aliphatic" and "aromatic" will be frequently used. In accordance with the above-mentioned IUPAC Regulations, organic compounds are classified into aliphatic compounds and aromatic compounds. The aliphatic compounds are defined based on the IUPAC Recommendations in 1995. In the Recommendations, the aliphatic compounds are defined as "linear or cyclic, saturated or unsaturated carbon compounds, excluding aromatic compounds." Furthermore, the aliphatic compounds used in the descriptions of the present embodiment include all of saturated and unsaturated, linear and cyclic compounds, and indicate the above described "organic compounds," "organic groups," and "substituents" that are constituted with atoms selected from among H (hydrogen atom); C (carbon atom); N (nitrogen atom); O (oxygen atom); S (sulfur atom); Si (silicon atom); halogen atoms selected from among Cl (chlorine atom), Br (bromine atom), and I (iodine atom).

When an aromatic group binds to an aliphatic group as in the case of an "aralkyl group," such a group is often referred to as an "aliphatic group substituted with an aromatic group," an "aromatic aliphatic group," or an "aromatic group-binding aliphatic group." This is based on the reactivity in the present embodiment, and this is because the properties of a group such as an aralkyl group regarding reactivity are extremely similar, not to the reactivity of aromatic compounds, but to that of aliphatic compounds. Further, there may be cases in which a non-aromatic reactive group including an aralkyl group and an alkyl group is often referred to as an "aliphatic group optionally substituted with an aromatic group," an "aliphatic group substituted with an aromatic group," an "aromatic group-binding aliphatic group," etc., and in which these groups are included in "aliphatic groups."

When the general formulae of the compounds used in the present specification will be described, they are defined using the Nomenclature Regulations defined by the above described IUPAC. However, as names of specific groups and names of exemplified compounds, trivial names are often used. In addition, the number of atoms, the number of substituents, and other numbers are all indicated as integers in the present specification.

When the substituents and compounds exemplified in the present specification have structural isomers, these structural isomers are included in the scope of the present invention, unless otherwise specified.

<<Method for Producing Carbonyl Compound>>

The method for producing the carbonyl compound of the present embodiment comprises a step (X) of reacting a compound having a urea bond represented by a formula (1) as shown below with a carbonic acid derivative having a carbonyl group (—C(=O)—) under heating at a temperature equal to or higher than the thermal dissociation temperature of the urea bond to obtain the carbonyl compound:

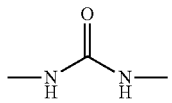

(1)

In addition, the step (X) is preferably carried out in the coexistence of a hydroxy compound.

The carbonyl compound obtained by the production method of the present embodiment preferably comprises an N-substituted carbamic acid ester.

Hereinafter, the compounds used in the present embodiment will be described in detail.

<Carbonic Acid Derivative>

The carbonic acid derivative used in the present embodiment indicates the general compound having a carbonyl group (—C(=O)—). Preferred examples of the carbonic acid derivative include a carbonic acid ester, an N-unsubstituted carbamic acid ester, urea, and phosgene. The carbonic acid derivative is preferably urea or an N-unsubstituted carbamic acid ester, and more preferably a carbonic acid ester.

<Carbonic Acid Ester>

The carbonic acid ester indicates a compound in which one or two hydrogen atoms of carbonic acid, $CO(OH)_2$, are substituted with an aliphatic group, an aromatic group and the like. The carbonic acid ester used in the present embodiment is preferably a compound represented by the following formula (8):

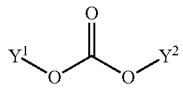

(8)

wherein $Y^1$ and $Y^2$ each independently represent an aliphatic group containing 1 to 20 carbon atoms, an aromatic group containing 6 to 20 carbon atoms, or an aromatic aliphatic group containing 7 to 20 carbon atoms, which optionally contain an oxygen atom.

The $Y^1$ and $Y^2$ in the above formula (8) are preferably groups constituted with specific non-metal atoms (carbon, oxygen, nitrogen, sulfur, silicon, and halogen atoms).

Preferred examples of such an aliphatic group include a linear hydrocarbon group, a cyclic hydrocarbon group, and a group to which at least one group selected from the linear hydrocarbon group and the cyclic hydrocarbon group binds (for example, a cyclic hydrocarbon group substituted with a linear hydrocarbon group, a linear hydrocarbon group substituted with a cyclic hydrocarbon group, etc.). An example of the aralkyl group is a linear and/or branched linear alkyl group substituted with an aromatic group. It is preferably an alkyl group containing 1 to 14 carbon atoms substituted with an aromatic group containing 6 to 19 carbon atoms. As described above, such an aromatic group is preferably a group constituted with specific non-metal atoms (carbon, oxygen, nitrogen, sulfur, silicon, and halogen atoms). Examples of such an aromatic group include a monocyclic aromatic group, a condensed polycyclic aromatic group, a crosslinked cyclic aromatic group, a multi-ring aromatic group, and a heterocyclic aromatic group. More preferred examples include a substituted and/or unsubstituted phenyl group, a substituted and/or unsubstituted naphthyl group, and a substituted and/or unsubstituted anthryl group.

When $Y^1$ and $Y^2$ are aromatic groups, an example of such a group is a group constituted with specific non-metal atoms (carbon, oxygen, nitrogen, sulfur, silicon, and halogen atoms). Examples of such a group include a monocyclic aromatic group, a condensed polycyclic aromatic group, a crosslinked cyclic aromatic group, a multi-ring aromatic group, and a heterocyclic aromatic group. More preferred examples include a substituted and/or unsubstituted phenyl group, a substituted and/or unsubstituted naphthyl group, and a substituted and/or unsubstituted anthryl group. The substituent may be substituted with a hydrogen atom, an aliphatic group (a linear hydrocarbon group, a cyclic hydrocarbon group, and a group to which at least one group selected from the linear hydrocarbon group and the cyclic hydrocarbon group binds (for example, a cyclic hydrocarbon group substituted with a linear hydrocarbon group, a linear hydrocarbon group substituted with a cyclic hydrocarbon group, etc.)), or the above described aromatic group, or it may be a group constituted with the above described aliphatic group and aromatic group.

Examples of such $Y^1$ and $Y^2$ include:

alkyl groups each containing 1 to 20 carbon atoms, such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group;

aryl groups each containing 6 to 20 carbon atoms, such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a diheptylphenyl group, a terphenyl group, a trimethylphenyl group, a triethylphenyl group, a tripropylphenyl group, and a tributylphenyl group; and an aralkyl groups each containing 7 to 20 carbon atoms, such as a phenylmethyl group, a phenylethyl group, a phenylpropyl group, a phenylbutyl group, a phenylpentyl group, a phenylhexyl group, a phenylheptyl group, a phenyloctyl group, and a phenylnonyl group.

Of these groups, aliphatic hydrocarbon groups, that is, alkyl groups each containing 1 to 8 carbon atoms, such as an ethyl group, a propyl group, a butyl group, a pentyl group, a hexyl group, a heptyl group or an octyl group, and aromatic groups such as a phenyl group, a methylphenyl group, an ethylphenyl group, a propylphenyl group, a butylphenyl group, a pentylphenyl group, an octylphenyl group, a nonylphenyl group, a cumylphenyl group, a biphenyl group, a dimethylphenyl group, a diethylphenyl group, a dipropylphenyl group, and a dipentylphenyl group, are more preferably used.

Specific examples of the carbonic acid ester include dimethyl carbonate, diethyl carbonate, dipropyl carbonate, dibutyl carbonate, dipentyl carbonate, dihexyl carbonate, diheptyl carbonate, dioctyl carbonate, diphenyl carbonate, dimethylphenyl carbonate, diethylphenyl carbonate, dipropylphenyl carbonate, dibutylphenyl carbonate, dipentylphenyl carbonate, dioctylphenyl carbonate, dinonylphenyl carbonate, dicumylphenyl carbonate, di(biphenyl)carbonate, di(dimethylphenyl)carbonate, di(diethylphenyl)carbonate, di(dipropylphenyl)carbonate, di(dipentylphenyl)carbonate, and di(dicumylphenyl)carbonate.

<N-Unsubstituted Carbamic Acid Ester>

The N-unsubstituted carbamic acid ester used in the present embodiment is preferably a compound represented by the following formula (9):

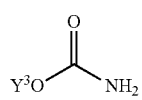

(9)

wherein $Y_3$ represents an aliphatic group containing 1 to 20 carbon atoms, an aromatic group containing 6 to 20 carbon atoms, or an aromatic aliphatic group containing 7 to 20 carbon atoms, which optionally contain an oxygen atom.

In the above formula (9), $Y^3$ preferably represents the same groups as those defined for $Y^1$ above.

Specific examples of the N-unsubstituted carbamic acid ester include
methyl carbamate, ethyl carbamate, propyl carbamate, butyl carbamate, pentyl carbamate, hexyl carbamate, heptyl carbamate, octyl carbamate, nonyl carbamate, decyl carbamate, undecyl carbamate, dodecyl carbamate, tridecyl carbamate, tetradecyl carbamate, pentadecyl carbamate, hexadecyl carbamate, heptadecyl carbamate, octadecyl carbamate, nonadecyl carbamate, phenyl carbamate, methylphenyl carbamate, ethylphenyl carbamate, propylphenyl carbamate, butylphenyl carbamate, pentylphenyl carbamate, hexylphenyl carbamate, heptylphenyl carbamate, octylphenyl carbamate, nonylphenyl)carbamate, decylphenyl carbamate, biphenyl carbamate, dimethylphenyl carbamate, diethylphenyl carbamate, dipropylphenyl carbamate, dibutylphenyl carbamate, dipentylphenyl carbamate, dihexylphenyl carbamate, diheptylphenyl carbamate, terphenyl carbamate, trimethylphenyl carbamate, triethylphenyl carbamate, tripropylphenyl carbamate, tributylphenyl carbamate, phenylmethyl carbamate, phenylethyl carbamate, phenylpropyl carbamate, phenylbutyl carbamate, phenylpentyl carbamate, phenylhexyl carbamate, phenylheptyl carbamate, phenyloctyl carbamate, and phenylnonyl carbamate.

<Organic Primary Amine>

In the method for producing the carbonyl compound of the present embodiment, an organic amine is used in some cases. As such an organic amine, an organic primary amine is preferably used. The term "organic primary amine" is used herein to mean "the primary amine (a mono primary amine and a poly primary amine)" stipulated by the Regulation C-8 described in Nomenclature (IUPAC Nomenclature of Organic Chemistry) defined by IUPAC (The International Union of Pure and Applied Chemistry). The organic primary amine is preferably a compound represented by the following formula (5):

(5)

wherein $R^3$ represents an organic group containing 1 to 85 carbon atoms, and a represents an integer from 1 to 10.

Examples of $R^3$ include an aliphatic group, an aromatic group, and a group formed by binding an aliphatic group to an aromatic group. Examples of such a group include a linear hydrocarbon group, a cyclic hydrocarbon group (for example, a monocyclic hydrocarbon group, a condensed polycyclic hydrocarbon group, a crosslinked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which at least one selected from the linear hydrocarbon group and the cyclic hydrocarbon group binds, and a group to which the above described group binds via a covalent bond with specific non-metal atoms (carbon, oxygen, nitrogen, sulfur, and silicon).

Among these $R^3$, if taking into consideration the unlikeliness of side reactions, the $R^3$ that can be preferably used in the present embodiment is a group containing 1 to 85 carbon atoms, which is selected from an aliphatic group, an aromatic group, and a group formed by binding an aliphatic group to an aromatic group. If taking into consideration flowability and the like, the $R^3$ is preferably a group containing 1 to 70 carbon atoms, and more preferably a group containing 1 to 13 carbon atoms.

Examples of the further preferred aliphatic group include a linear hydrocarbon group, a cyclic hydrocarbon group, and a group to which at least one group selected from the linear hydrocarbon group and the cyclic hydrocarbon group binds (for example, a cyclic hydrocarbon group substituted with a linear hydrocarbon group, a linear hydrocarbon group substituted with a cyclic hydrocarbon group, etc.), each of which contains 6 to 70 carbon atoms.

Preferred examples of the organic primary amine constituted with the $R^3$ include:

(1) an aromatic organic mono primary amine, in which $R^3$ represents a group containing 6 to 85 carbon atoms, which contains one or more aromatic rings optionally substituted with aliphatic and/or aromatic groups, the aromatic rings of which are substituted with $NH_2$ groups, and a is an integer of 1;

(2) an aromatic organic poly primary amine, in which $R^3$ represents a group containing 6 to 85 carbon atoms, which contains one or more aromatic rings optionally substituted with aliphatic and/or aromatic groups, the aromatic rings of which are substituted with $NH_2$ groups, and a is an integer of 2 or greater; and (3) an aliphatic organic poly primary amine, in which $R^3$ represents an aliphatic group containing 1 to 85 carbon atoms, which is optionally substituted with an aromatic group, and a is an integer of 2 or 3.

With regard to the above-mentioned organic amines, an organic amine, in which an atom (preferably, a carbon atom) to which an $NH_2$ group binds is contained in the aromatic ring, is defined as an aromatic organic amine, whereas an organic amine, in which an $NH_2$ group binds to an atom (mainly, a carbon atom) that is not in the aromatic ring, is defined as an aliphatic organic amine.

Specific examples of preferred organic primary amines will be given below.

(1) Aromatic Organic Mono Primary Amine

An example of the organic primary amine used in the present embodiment is an aromatic organic mono primary amine, wherein, in the above formula (5), $R^3$ is a group containing 6 to 85 carbon atoms, which contains one or more aromatic rings optionally substituted with aliphatic and/or aromatic groups, the aromatic rings of which are substituted with $NH_2$ groups, and a is an integer of 1. A preferred example of the organic primary amine used in the present embodiment is an aromatic organic mono primary amine, wherein, in the above formula (5), $R^3$ is a group containing 6 to 70 carbon atoms and a is an integer of 1. If taking into consideration flowability and the like, a more preferred example is an aromatic organic mono primary amine, wherein, in the above formula (5), $R^3$ is a group containing 6 to 13 carbon atoms and a is an integer of 1, and it is an aromatic organic mono primary amine represented by the following formula (10):

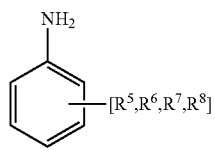

(10)

wherein at least one of the ortho-position and/or para-position of the $NH_2$ group is unsubstituted, and each of $R^5$ to $R^8$ independently represents a group substituted in any given position at which the aromaticity of the ring is maintained.

$R^5$ to $R^8$ may independently substitute the aromatic ring, or $R^5$ to $R^8$ may bind to one another to form a ring together with the aromatic ring. In addition, each of $R^5$ to $R^8$ preferably represents a hydrogen atom, or a group constituted with an alkyl group, a cycloalkyl group, an aryl group, and a group to which a group selected from these groups binds via a saturated aliphatic bond and/or an ether bond. The aryl group optionally has a hydroxy group.

The number of carbon atoms contained in each of $R^5$ to $R^8$ is an integer ranging from 0 to 7. The total number of carbon atoms constituting the aromatic organic mono primary amine represented by the formula (10) is an integer from 6 to 50, and preferably an integer from 6 to 13.

A more preferred example of the aromatic organic mono primary amine represented by the formula (10) is an aromatic organic mono primary amine, wherein $R^5$ to $R^8$ in the formula (10) each represent a hydrogen atom, or a group selected from alkyl groups such as a methyl group and an ethyl group. Examples of such an aromatic organic mono primary amine include aniline, aminotoluene, dimethylaniline, diethylaniline, dipropylaniline, aminonaphthalene, aminomethylnaphthalene, dimethylnaphthylamine, and trimethylnaphthylamine. Of these, aniline is more preferably used.

It is to be noted that compounds given as specific examples in the present embodiment may have isomers, such individual isomers are also included in the specific examples.

(2) Aromatic Organic Poly Primary Amine

An example of the organic primary amine used in the present embodiment is an aromatic organic poly primary amine, wherein, in the above formula (5), $R^3$ is a group containing 6 to 85 carbon atoms, which contains one or more aromatic rings optionally substituted with aliphatic and/or aromatic groups, the aromatic rings of which are substituted with $NH_2$ groups, and a is an integer of 2 or greater. A preferred example of the organic primary amine used in the present embodiment is an aromatic organic poly primary amine, wherein, in the above formula (5), $R^3$ is a group containing 6 to 70 carbon atoms and a is an integer of 2 or greater. If taking into consideration flowability and the like, a more preferred example is an aromatic organic poly primary amine, wherein, in the above formula (5), $R^3$ is a group containing 6 to 13 carbon atoms, which contains one or more aromatic rings that are further optionally substituted with an alkyl group, an aryl group or an aralkyl group, an $NH_2$ group binds to the aromatic group contained in $R^3$, and a is an integer of 2 or greater.

Examples of such an aromatic organic poly primary amine include diaminobenzene, diaminotoluene, methylenedianiline, diaminomesitylene, diaminobiphenyl, diaminodibenzyl, bis(aminophenyl)methane, bis(aminophenyl)propane, bis(aminophenyl)ether, bis(aminophenoxyethane), α,α'-diaminoxylene, diaminoanisole, diaminophenetole, diaminonaphthalene, di(aminomethyl)benzene, di(aminomethyl)pyridine, diaminomethylnaphthalene, and polymethylenepolyphenylpolyamine represented by the following formula (11):

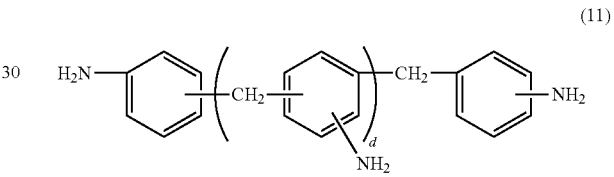

(11)

wherein d represents an integer from 0 to 6.

(3) Aliphatic Organic Poly Primary Amine

An example of the organic primary amine used in the present embodiment is an aliphatic organic poly primary amine, wherein, in the above formula (5), $R^3$ is an aliphatic group containing 1 to 85 carbon atoms, which is optionally substituted with an aromatic group, and a is an integer of 2 or 3.

The aliphatic organic poly primary amine is preferably an aliphatic organic poly primary amine, in which the aliphatic group is a linear hydrocarbon group, a cyclic hydrocarbon group, or a group to which at least one group selected from the linear hydrocarbon group and the cyclic hydrocarbon group binds (for example, a cyclic hydrocarbon group substituted with a linear hydrocarbon group, a linear hydrocarbon group substituted with a cyclic hydrocarbon group, etc.). The number of carbon atoms contained in the aliphatic group is more preferably 1 to 70, and if taking into consideration flowability necessary for industrial mass production, etc., the number of carbon atoms is further preferably 6 to 13.

A specific example of the aliphatic organic poly primary amine is an aliphatic organic poly primary amine, wherein, in the formula (5), $R^3$ is a straight chain and/or branched chain alkyl group, a cycloalkyl group, or a group constituted with the alkyl group and the cycloalkyl group.

Examples of such an aliphatic organic poly primary amine include:

alkyl-di-primary amines such as ethylenediamine, diaminopropane, diaminobutane, diaminopentane, diaminohexane, diaminoheptane, diaminooctane, diaminononane, and diaminodecane;

alkyl-tri-primary amines such as triaminohexane, triaminoheptane, triaminooctane, triaminononane, and triaminodecane;

cycloalkyl primary amines such as diaminocyclobutane, diaminocyclopentane, and diaminocyclohexane; and cyclohexyl poly primary amines substituted with alkyl groups, such as 3-aminomethyl-3,5,5-trimethylcyclohexylamine (cis- and/or trans-forms) and methylenebis(cyclohexylamine).

The organic primary amines described in (1), (2), and (3) above are preferably used. Among others, organic primary amines, which are organic primary monoamines, organic primary diamines or organic primary triamines (organic primary amines wherein, in the above formula (5), a is an integer of 1, 2, or 3), are more preferable.

<Compound Having Urea Bond>

The compound having the urea bond used in the present embodiment is a compound containing a urea bond represented by the following formula (1) (hereinafter simply referred to as a "compound containing a urea bond" at times):

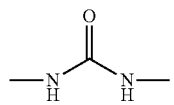

(1)

Specific examples of such a compound containing a urea bond will be given below.

<N-substituted Urea>

The N-substituted urea represented by the following formula (12) is one of the compounds having the urea bond represented by the above formula (1):

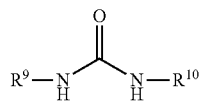

(12)

wherein $R^9$ and $R^{10}$ each independently represent an organic group containing 1 to 85 carbon atoms.

In the above formula (12), it is preferable that $R^9$ and $R^{10}$ each independently represent an aliphatic group containing 1 to 85 carbon atoms, or an aromatic group containing 6 to 85 carbon atoms. The aliphatic group containing 1 to 85 carbon atoms is optionally substituted with an aromatic group. The aromatic group containing 6 to 85 carbon atoms contains one or more aromatic rings, and the aromatic rings are optionally substituted with aliphatic groups and/or aromatic groups. Examples of a preferred aliphatic group include a linear hydrocarbon group, a cyclic hydrocarbon group (including an aromatic group), and a group to which at least one group selected from the linear hydrocarbon group and the cyclic hydrocarbon group binds (for example, a cyclic hydrocarbon group substituted with a linear hydrocarbon group, a linear hydrocarbon group substituted with a cyclic hydrocarbon group, etc.). Examples of a more preferred aliphatic group include a linear hydrocarbon group, a cyclic hydrocarbon group, and a group to which at least one group selected from the linear hydrocarbon group and the cyclic hydrocarbon group binds (for example, a cyclic hydrocarbon group substituted with a linear hydrocarbon group, a linear hydrocarbon group substituted with a cyclic hydrocarbon group, etc.), each of which contains 1 to 70 carbon atoms. Taking into consideration flowability necessary for industrial mass production, etc., a further preferred example is a compound wherein $R^9$ and $R^{10}$ each independently represent a linear hydrocarbon group, a cyclic hydrocarbon group, and a group to which at least one group selected from the linear hydrocarbon group and the cyclic hydrocarbon group binds (for example, a cyclic hydrocarbon group substituted with a linear hydrocarbon group, a linear hydrocarbon group substituted with a cyclic hydrocarbon group, etc.), each of which contains 6 to 13 carbon atoms and each of which is constituted with a carbon atom and a hydrogen atom.

That is to say, it is the case of a group wherein $R^9$ and $R^{10}$ are a straight chain and/or branched chain alkyl group, a cycloalkyl group, and a group constituted with the alkyl group and the cycloalkyl group. Moreover, when $R^9$ and $R^{10}$ are aromatic groups, they are aromatic groups containing 6 to 70 carbon atoms. Taking into consideration flowability and the like, $R^9$ and $R^{10}$ more preferably contain one or more aromatic rings, and further, the aromatic rings are aromatic groups containing 6 to 13 carbon atoms that are optionally substituted with alkyl groups, aryl group, and aralkyl groups.

Examples of such N-substituted urea include 1,3-dimethyl urea, 1,3-diethyl urea, 1,3-dipropyl urea, 1,3-dibutyl urea, 1,3-dipentyl urea, 1,3-dihexyl urea, 1,3-dioctyl urea, 1,3-didecyl urea, 1,3-dioctadecyl urea, 1,3-dicyclopentyl urea, 1,3-dicyclohexyl urea, 1,3-dicyclooctyl urea, 1,3-di(phenolethyl)urea, 1,3-di(phenylbutyl)urea, 1,3-di(phenyloctyl) urea, 1,3-di(phenyldodecyl)urea, 1,3-diphenyl urea, 1,3-di(methylphenyl)urea, 1,3-di(ethylphenyl)urea, 1,3-di(propylphenyl)urea, 1,3-di(butylphenyl)urea, 1,3-di(pentylphenyl)urea, 1,3-di(hexylphenyl)urea, 1,3-di(heptylphenyl)urea, 1,3-di(octylphenyl)urea, 1,3-di(nonylphenyl group, 1,3-di(decylphenyl)urea, 1,3-di(biphenyl)urea, 1,3-di(dimethylphenyl)urea, 1,3-di(diethylphenyl)urea, 1,3-di(dipropylphenyl)urea, 1,3-di(dibutylphenyl)urea, 1,3-di(dipentylphenyl)urea, 1,3-di(dihexylphenyl)urea, 1,3-di(diheptylphenyl)urea, 1,3-di(terphenyl)urea, 1,3-di(trimethylphenyl)urea, 1,3-di(triethylphenyl)urea, 1,3-di(tripropylphenyl)urea, 1,3-di(tributylphenyl)urea, 1,3-di(phenylmethyl)urea, 1,3-di(phenylethyl)urea, 1,3-di(phenylpropyl)urea, 1,3-di(phenylbutyl)urea, 1,3-di(phenylpentyl)urea, 1,3-di(phenylhexyl)urea, 1,3-di(phenylheptyl)urea, 1,3-di(phenyloctyl)urea, and 1,3-di(phenylnonyl)urea.

<Method for Producing Compound Having Urea Bond>

The compound having the urea bond represented by the above formula (1) can be produced, for example, from raw material ingredients containing an organic primary amine and a carbonic acid derivative. The compound having the urea bond obtained by this production method is, for example, a compound represented by the following formula (2):

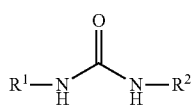

(2)

wherein $R^1$ and $R^2$ each independently represent an organic group containing a group derived from the organic primary amine.

For instance, when the organic primary amine is the organic primary amine represented by the above formula (5), and it is an organic primary monoamine wherein, in the above formula (5), a is 1, the compound represented by the above formula (2) can be represented by the following formula (13):

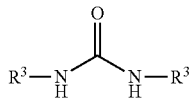
(13)

wherein $R^3$ represents an organic group containing 1 to 85 carbon atoms.

In addition, when the organic primary amine is the organic primary amine represented by the above formula (5) wherein a is 2, the compound having the urea bond represented by the above formula (2) can be represented by the following formula (14):

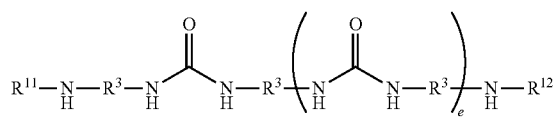
(14)

wherein $R^3$ represents an organic group containing 1 to 85 carbon atoms, $R^{11}$ and $R^{12}$ each independently represent one group selected from the group consisting of the following formulae (15) to (17), and e represents 0 or a positive integer.

—H            (15)

—COOR$^{13}$  (16)

—CONH$_2$     (17)

wherein $R^{13}$ represents a residue obtained by removing one OH group from a hydroxy compound.

The above described compound having the urea bond may be a compound obtained together with an N-substituted carbamic acid ester, when an organic primary amine is reacted with a carbonic acid derivative to produce the N-substituted carbamic acid ester. Hereafter, a method for producing a compound having a urea bond as well as an N-substituted carbamic acid ester by reacting an organic primary amine with a carbonic acid derivative will be described.

There are several methods for producing a compound having a urea bond from raw material ingredients containing an organic primary amine and a carbonic acid derivative. Thus, the production method used herein is not particularly limited. The following methods are preferably used.

Method (1): A method of producing a compound having a urea bond from an organic primary amine, urea, and a hydroxy compound, in which the urea is used as a carbonic acid derivative.

Method (2): A method of producing a compound having a urea bond from an organic primary amine and a carbonic acid ester, in which the carbonic acid ester represented by the above formula (8) is used as a carbonic acid derivative.

Method (3): A method of producing a compound having a urea bond from an organic primary amine and a phosgene, in which the phosgene is used as a carbonic acid derivative.

[Method (1)]

First, the method (1) will be described.

The method (1) is further classified into two methods, namely, the following method (i) and method (ii).

Method (i): A method comprising a step (A) of "simultaneously" reacting an organic primary amine, urea, and a hydroxy compound.

Method (ii): A method comprising a step (B) of reacting an organic primary amine with urea to obtain a reaction mixture comprising a compound having a ureido group, and a step (C) of reacting the compound having the ureido group obtained in the step (B) with a hydroxy compound.

(Method (i))

First of all, the term "simultaneously" used in the step (A) of the method (i) means that the step is not divided, differing from the method (ii). It does not necessarily mean that the organic primary amine, the urea, and the hydroxy compound are reacted with one another completely simultaneously.

In the step (A), for example, an N-substituted carbamic acid ester is generated as a result of the reaction represented by the following formula (18), and at the same time, a compound having a urea bond is generated as a result of the reactions represented by the following formula (19) and formula (20).

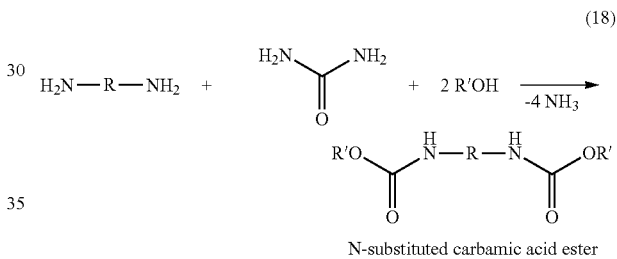
(18)

N-substituted carbamic acid ester

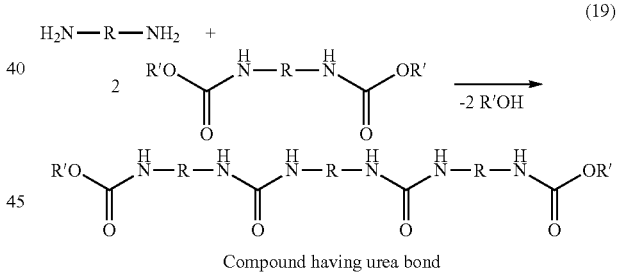
(19)

Compound having urea bond

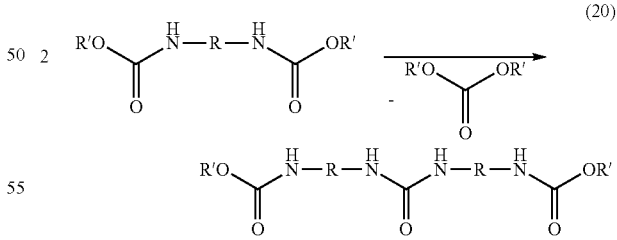
(20)

wherein

R and R' each independently represent an organic group.

In the above formulae (18) to (20), the case of using a bifunctional organic primary amine is described in order to facilitate explanation. However, the method of the present embodiment is not limited to the use of such a bifunctional organic primary amine. In addition, the processes of generating an N-substituted carbamic acid ester and a compound having a urea bond are not limited to the above formulae.

Reaction conditions for reacting an organic primary amine, urea, and a hydroxy compound are different depending on the types of compounds to be reacted. The hydroxy compound is used at a stoichiometric ratio of 0.5:1 to 500:1 based on the amount of the amino group of the organic primary amine used. If taking into consideration the size of a reaction vessel or the solubility of a urea derivative, the hydroxy compound is used at a stoichiometric ratio of, preferably from 1:1 to 200:1, more preferably from 1.5:1 to 100:1, and further preferably from 2:1 to 50:1, based on the amount of the amino group of the organic primary amine used.

The urea is used at a stoichiometric ratio of 0.5:1 to 50:1 based on the amount of the amino group of the organic primary amine used. If the amount of urea used is small, there may be a case in which an unreacted amino group remains. Accordingly, an excessive amount of urea is preferably used. If taking into consideration the size of a reaction vessel or the solubility of urea, the urea is used at a stoichiometric ratio of, preferably from 1.1:1 to 10:1, and more preferably from 1.5:1 to 5:1, based on the amount of the amino group of the organic primary amine used.

The reaction temperature depends on the reactivity of the organic amine, urea, and hydroxy compound used. It is preferably in a range of 100° C. to 350° C. If the reaction temperature is 350° C. or lower, decomposition of the urea or dehydrogenation of the hydroxy compound can be suppressed. Otherwise, the decomposition reaction, degeneration reaction, and the like of the N-substituted carbamic acid ester as a product can be suppressed. From such a viewpoint, the reaction temperature is more preferably in a range of 120° C. to 320° C., and further preferably in a range of 140° C. to 300° C.

The reaction pressure depends on, for example, the composition of the reaction system, the reaction temperature, a method of removing by-products (e.g. ammonia), the reaction apparatus, etc. The reaction pressure can be set to a reduced pressure, an ordinary pressure, or a compressed pressure. In general, the reaction pressure is preferably in a range of 0.01 kPa to 10 MPa (absolute pressure). If taking into consideration facilitation of industrial production, a reduced pressure or an ordinary pressure is preferable, and a pressure in a range of 0.1 kPa to 0.1 MPa (absolute pressure) is more preferable.

A type of a reaction vessel in which the step (A) is carried out is not particularly limited, and a known reaction vessel can be used. Tank-type and/or column-type reaction vessels, which comprise a condenser, are preferably used. Specifically, conventionally known reaction vessels, such as an agitation tank, a pressurized agitation tank, a depressurized agitation tank, a column-type reaction vessel, a distillation column, a packed column, and a thin-film distiller, can be used in combination, as appropriate.

In addition, the reaction vessel preferably comprises a condenser. The type of such a condenser is not particularly limited, and a known condenser can be used. For example, conventionally known condensers, such as a multitubular cylindrical condenser, a double-tube condenser, a single-tube condenser, and an air-cooled condenser, can be used in combination, as appropriate. The condenser may be equipped inside the reaction vessel, or it may also be equipped outside the reaction vessel and may be connected with the reaction vessel via a pipe. Considering the type of the reaction vessel or condenser, a method of handling a condensate, and the like, various forms can be adopted.

Materials for the reaction vessel and condenser are not particularly limited. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added, as necessary. For example, steps and apparatuses, such as a step of removing the generated ammonia, a step of purifying the organic primary amine, a step of dissolving the urea in the hydroxy compound, a step of dissolving the hydroxy compound, a step of separating the hydroxy compound, a step of separating and/or purifying the hydroxy compound, a step of burning or discarding by-products, etc., may be added, to such an extent that they seem to be required in the present technical field.

In the reaction of the organic primary amine, the urea, and the hydroxy compound, ammonia is generated as a by-product in many cases. Thus, the reaction is preferably carried out, while removing such ammonia from the reaction system. As such a removal method, a reaction distillation method, a method using inert gas, membrane separation, a method involving adsorptive separation, and the like can be applied. For example, the reaction distillation method is a method of separating ammonia, which has been successively generated as a result of the reaction, in a gaseous state by distillation. In order to increase the distillation efficiency of ammonia, distillation can be carried out, while boiling a solvent or the hydroxy compound. In addition, the method using inert gas is a method of accompanying ammonia successively generated as a result of the reaction in a gaseous state with inert gas to separate the ammonia from the reaction system. A method of using inert gas such as nitrogen, helium, argon, carbon dioxide, methane, ethane or propane, singly or in combination, and introducing the inert gas into the reaction system, is preferable. As adsorbents used in the method involving adsorptive separation, adsorbents that can be used under temperature conditions in which the present reaction is carried out, such as silica, alumina, various types of zeolites, and diatomaceous earths, can be used. These methods of removing ammonia from the reaction system may be applied, either singly or in combination of multiple types of methods.

In the present reaction, for the purpose of increasing the reaction rate for example, a catalyst can be used. Examples of such a catalyst that can be preferably used herein include: basic catalysts such as the methylate, ethylate and butylate of lithium, sodium, potassium, calcium and barium; single bodies of rare earth elements, antimony and bismuth, and the oxides, sulfides and salts of these elements; boron as a single body and boron compounds; the metals of copper elements, zinc elements, aluminum elements, carbon elements and titanium elements in the periodic table, and the metal oxides and sulfides thereof; and the carbides and nitrides of carbon elements other than carbon, titanium elements, vanadium elements and chromium elements, in the periodic table. In the case of using such a catalyst, the amount used is not particularly limited. The catalyst can be used at a stoichiometric ratio of 0.0001:1 to 100:1 based on the amount of the amino group of the organic primary amine. If a catalyst is added, it becomes necessary to remove the catalyst in many cases. Thus, the reaction is preferably carried out without adding catalysts. When a catalyst is used, such a catalyst may be removed after completion of the reaction.

The reaction time (which is a retention time, when the reaction is a continuous reaction) is different depending on the composition of the reaction system, the reaction temperature, the reaction apparatus, the reaction pressure, and the like. It is generally 0.01 to 100 hours. The reaction time can be determined based on the amount of a compound of interest generated. For example, the reaction solution is sampled, the content of a compound of interest in the reaction solution is then quantified, and it is then confirmed that a desired yield can be achieved with respect to the amount of the organic primary amine used, so that the reaction can be terminated.

In the reaction, it is not always necessary to use a reaction solvent. However, for the purpose of facilitating the reaction operations, etc., a suitable reaction solvent can be used. Examples of such a reaction solvent that can be preferably used herein include: alkanes such as pentane, hexane, heptane, octane, nonane, and decane; aromatic hydrocarbons and alkyl-substituted aromatic hydrocarbons, such as benzene, toluene, xylene, ethylbenzene, diisopropylbenzene, dibutylbenzene, and naphthalene; nitrile compounds such as acetonitrile and benzonitrile; aromatic compounds substituted with halogen or a nitro group, such as chlorobenzene, dichlorobenzene, bromobenzene, dibromobenzene, chloronaphthalene, bromonaphthalene, nitrobenzene, and nitronaphthalene; polycyclic hydrocarbon compounds such as diphenyl, substituted diphenyl, diphenylmethane, terphenyl, anthracene, and dibenzyltoluene; aliphatic hydrocarbons such as cyclohexane, cyclopentane, cyclooctane, and ethylcyclohexane; ketones such as methyl ethyl ketone and acetophenone; esters such as dibutyl phthalate, dihexyl phthalate, dioctyl phthalate, and benzyl butyl phthalate; ethers and thioethers, such as tetrahydrofuran, 1,4-dioxane, 1,2-dimethoxyethane, diphenyl ether, and diphenyl sulfide; ketone compounds such as acetone and methyl ethyl ketone; ester compounds such as ethyl acetate and ethyl benzoate; and sulfoxides such as dimethyl sulfoxide and diphenyl sulfoxide. Needless to say, a hydroxy compound, which is used in an excessive amount in the present reaction, is also preferably used as the reaction solvent.

It is to be noted that compounds given as specific examples in the present embodiment may have isomers, such individual isomers are also included in the specific examples.

(Method (ii))

Next, the method (ii) will be described.

The method (ii) is a method of reacting an organic primary amine, urea, and a hydroxy compound via steps comprising the above described step (B) and step (C).

Hereafter, the step (B) will be described in detail.

The step (B) is a step of reacting an organic primary amine with urea to obtain a reaction mixture containing a compound having a ureido group (this compound having a ureido group will be described later). As described later, there may be a case in which a compound having a urea bond is generated even in the step (B). The compound having the urea bond obtained in the step (B) can also be used as the compound having the urea bond of the present embodiment.

Reaction conditions for carrying out the reaction of the organic primary amine with the urea are different depending on the types of compounds to be reacted. The number of urea groups used is 0.5 to 100 times larger than the number of amino groups of the organic primary amine used.

In the step (B), the reaction of generating a compound having a ureido group is a reaction in which equilibrium largely lies on the generation side, or an irreversible reaction. In the step (B), ammonia is generated as a by-product. It was revealed that the ammonia concentration in the system is hardly dependent on the yield of a compound having a ureido group in the reaction of generating the compound having the ureido group. On the other hand, when a hydroxy compound is used as a solvent in the step (B) (details will be described later), there may be a case in which the compound having the ureido group reacts with the hydroxy compound, and an N-substituted carbamic acid ester is then generated as a result of dissociation of ammonia. However, since the equilibrium of the reaction of generating such an N-substituted carbamic acid ester largely lies on the raw material side, unless the generated ammonia is removed to reduce the concentration of the ammonia, the N-substituted carbamic acid ester is hardly generated in many cases. Thus, by maintaining the ammonia concentration in the reaction solution in the step (B) at a certain level, the generation of the N-substituted carbamic acid ester as a result of the reaction of the generated compound having the ureido group with the hydroxy compound can be suppressed, and the compound having the ureido group can be selectively generated. Accordingly, the ammonia concentration is preferably higher than 10 ppm, more preferably higher than 100 ppm, further preferably higher than 300 ppm, and particularly preferably higher than 1000 ppm.

The step (B) can be carried out in a reaction temperature range of 30° C. to 250° C. A high temperature is preferably applied in order to increase the reaction rate. On the other hand, there is a case in which an unfavorable reaction (e.g. the decomposition reaction of urea, etc.) occurs at a high temperature and as a result, complicatedly substituted urea derivatives and the like are generated. Thus, the reaction temperature is in a range, more preferably of 50° C. and 200° C., and further preferably of 70° C. and 180° C. In order to keep the reaction temperature constant, a reaction vessel, in which the step (B) is carried out, may be equipped with a known cooling device and/or heating device.

In the step (B), as a result of a reaction represented by the following formula (21), in addition to a compound having a ureido group, a condensate of the compound having the ureido group or a compound having a urea bond with the compound having the ureido group may also be generated (for example, the following formulae (22) and (23)).

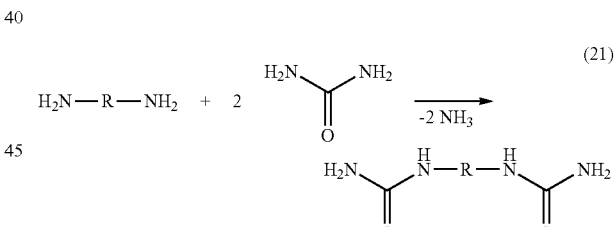

Compound having ureido group

Compound having urea bond

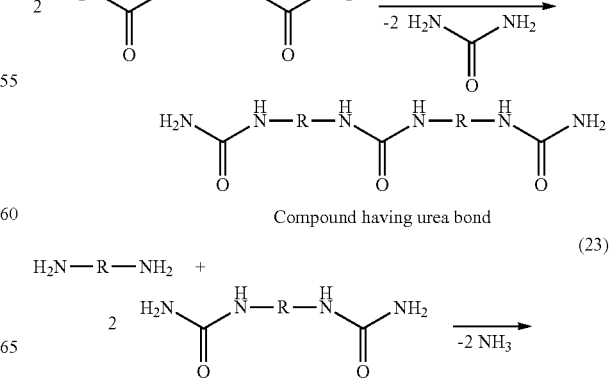

-continued

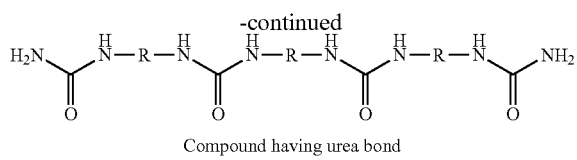

Compound having urea bond wherein

R and R' each independently represent an organic group.

In the above formulae (21) to (23), the case of using a bifunctional organic primary amine is described in order to facilitate explanation. However, the method of the present embodiment is not limited to the use of such a bifunctional organic primary amine. In addition, the processes of generating a compound having a ureido group, an N-substituted carbamic acid ester and a compound having a urea bond are not limited to the above formulae.

The reaction pressure is different depending on the type of a compound used, the composition of the reaction system, the reaction temperature, the reaction apparatus, etc. In general, the reaction pressure is preferably in a range of 0.01 kPa to 10 MPa (absolute pressure). If taking into consideration facilitation of industrial production, the reaction pressure is more preferably in a range of 0.1 kPa to 1 MPa (absolute pressure).

The reaction time (which is a retention time, when the reaction is a continuous reaction) is not particularly limited. It is generally 0.001 to 100 hours, preferably 0.01 to 80 hours, and more preferably 0.1 to 50 hours. Otherwise, the reaction solution is sampled, and it is then confirmed by, for example, liquid chromatography that a desired amount of compound having a ureido group has been generated, so that the reaction can be terminated. The step (B) is a step of producing a compound having a ureido group. If large quantities of amino groups derived from unreacted organic primary amines are present in the step (B), there may be a case in which an unpredictable side reaction occurs in a step (C) following the step (B). Accordingly, it is preferable that, in the step (B), a compound having a ureido group be generated at a yield as high as possible, and that the amounts of the amino groups derived from the organic primary amines be reduced. Specifically, it is preferable to continue the reaction, until the ratio of the number of the amino groups derived from the organic primary amines to the number of ureido groups constituting the compounds having ureido groups becomes preferably 0.25 or less, more preferably 0.1 or less, and further preferably 0.05 or less.

In the present reaction, a catalyst can be used, as necessary. Examples of such a catalyst that can be used herein include: organic metal compounds and inorganic metal compounds, such as tin, lead, copper, and titanium; and basic catalysts, such as the alcoholates of alkali metals and alkali earth metals, which include the methylate, ethylate and butylate of lithium, sodium, potassium, calcium and barium.

From the viewpoint of a decrease in the viscosity of a reaction solution and/or the achievement of a homogeneous reaction solution, the reaction in the step (B) is preferably carried out in the presence of a solvent. Examples of such a reaction solvent that can be preferably used herein include: alkanes such as pentane, hexane, heptane, octane, nonane, and decane; aromatic hydrocarbons and alkyl-substituted aromatic hydrocarbons, such as benzene, toluene, xylene, ethylbenzene, diisopropylbenzene, dibutylbenzene, and naphthalene; nitrile compounds such as acetonitrile and benzonitrile; aromatic compounds substituted with halogen or a nitro group, such as chlorobenzene, dichlorobenzene, bromobenzene, dibromobenzene, chloronaphthalene, bromonaphthalene, nitrobenzene, and nitronaphthalene; polycyclic hydrocarbon compounds such as diphenyl, substituted diphenyl, diphenylmethane, terphenyl, anthracene, and dibenzyltoluene; aliphatic hydrocarbons such as cyclohexane, cyclopentane, cyclooctane, and ethylcyclohexane; ketones such as methyl ethyl ketone and acetophenone; esters such as dibutyl phthalate, dihexyl phthalate, dioctyl phthalate, and benzyl butyl phthalate; ethers and thioethers, such as tetrahydrofuran, 1,4-dioxane, 1,2-dimethoxyethane, diphenyl ether, and diphenyl sulfide; ketone compounds such as acetone and methyl ethyl ketone; ester compounds such as ethyl acetate and ethyl benzoate; sulfoxides such as dimethyl sulfoxide and diphenyl sulfoxide; water; hydroxy compounds such as alcohol and aromatic hydroxy compounds. From the viewpoint of the solubility of the compound having the ureido group as a product, the reaction solvent is preferably water or a hydroxy compound (alcohol or an aromatic hydroxy compound). These solvents can be used singly or in the form of a mixture of two or more types.

The above-mentioned reaction solvent can be used in any given amount. When a hydroxy compound is used as such a reaction solvent, it can be used in an amount 1 to 100 times, at a stoichiometric ratio, as large as the amount of the amino group of the organic primary amine. In order to improve the flowability of a reaction solution and to efficiently promote the reaction, alcohol is preferably used in an excessive amount with respect to the amount of the amino group of the organic primary amine. However, if an extremely large amount of alcohol is used, there is a risk of requiring a large reaction vessel, etc. Thus, the reaction solvent may be used in an amount range, more preferably 5 to 50 times, and further preferably 8 to 20 times, as large as the amount of the amino group of the organic primary amine.

A type of a reaction apparatus used to carry out the present reaction is not particularly limited, and a known reaction vessel can be used. For example, conventionally known reaction vessels, such as an agitation tank, a pressurized agitation tank, a depressurized agitation tank, a column-type reaction vessel, a distillation column, a packed column, and a thin-film distiller, can be used in combination, as appropriate. Materials used for the reaction vessel are not particularly limited, either. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added, as necessary. For example, steps and apparatuses, such as a step of removing the generated ammonia, a step of purifying the organic primary amine, a step of dissolving the urea in the aromatic hydroxy compound, a step of dissolving the aromatic hydroxy compound, a step of separating alcohol, a step of separating and/or purifying the aromatic hydroxy compound, a step of purifying the compound having the ureido group from the generated reaction solution, a step of burning or discarding by-products, etc., may be added, to such an extent that they seem to be required in the present technical field.

The subsequent step (C) is a step of reacting the compound having the ureido group obtained in the step (B) with a hydroxy compound. In the step (C), an N-substituted carbamic acid ester is generated as a result of a reaction represented by the following formula (24), and at the same time, a compound having a urea bond is also generated, for example, as a result of reactions represented by the following formula (25) and formula (26):

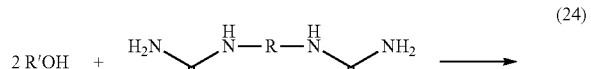

(24)

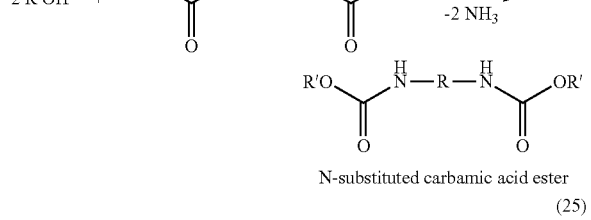

N-substituted carbamic acid ester (25)

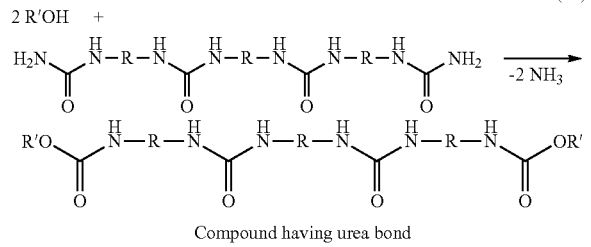

Compound having urea bond (26)

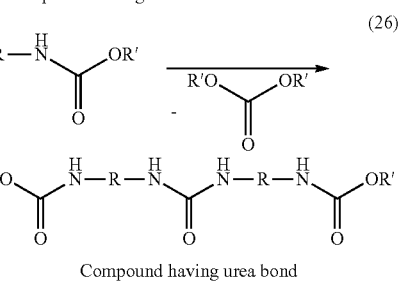

Compound having urea bond wherein

R and R' each independently represent an organic group.

In the above formulae (24) to (26), the case of using a bifunctional organic primary amine is described in order to facilitate explanation. However, the method of the present embodiment is not limited to the use of such a bifunctional organic primary amine. In addition, the processes of generating an N-substituted carbamic acid ester and a compound having a urea bond are not limited to the above formulae.

When a reaction solvent is used in the step (B), the reaction solvent may be removed from the reaction solution of the step (B) before performing the step (C), or the step (C) may be directly performed without removing the reaction solvent. When the reaction solvent used in the step (B) is different from the hydroxy compound in the step (C), a hydroxy compound may be newly added, and the step (C) may be then carried out.

Reaction conditions for reacting a compound having a ureido group with a hydroxy compound in the step (C) are different depending on the types of compounds to be reacted. The hydroxy compound is used at a stoichiometric ratio of 1:1 to 500:1 based on the numbers of the ureido groups in the compound having the ureido groups used. In order to ensure the solubility of the compound having the ureido group and a product, a largely excessive amount of hydroxy compound is preferably used. However, if taking into consideration the size of a reaction vessel, the hydroxy compound is used at a stoichiometric ratio of, preferably from 1:1 to 100:1, more preferably from 2:1 to 50:1, and further preferably from 3:1 to 20:1.

The reaction temperature depends on the types of compounds to be used, and it is preferably in a temperature range of 100° C. to 350° C. If the reaction temperature is 100° C. or higher, the strong binding of the hydroxy compound to ammonia generated as a by-product can be suppressed, and thus, a desired reaction favorably progresses. In addition, generation of a complicatedly substituted carbonyl compound can be suppressed. On the other hand, if the reaction temperature is 350° C. or lower, decomposition of the urea or dehydrogenation of the hydroxy compound can be suppressed. From such a viewpoint, the reaction temperature is more preferably in a range of 120° C. to 320° C., and further preferably in a range of 140° C. to 300° C.

The reaction pressure is different depending on the composition of the reaction system, the reaction temperature, a method of removing ammonia, the reaction apparatus, etc. In general, the reaction pressure is preferably in a range of 0.01 kPa to 10 MPa (absolute pressure). If taking into consideration facilitation of industrial production, the reaction pressure is preferably in a range of 0.1 Pa and 5 MPa (absolute pressure). If taking into consideration the removal of gaseous ammonia from the reaction system, the reaction pressure is more preferably in a range of 0.1 Pa to 1.5 MPa (absolute pressure).

In the reaction of the step (C), ammonia is generated as a by-product in many cases. Thus, the reaction is preferably carried out, while removing such ammonia from the reaction system. Preferably, ammonia is removed so that the concentration of the ammonia in the reaction solution becomes preferably 1000 ppm or less, more preferably 300 ppm or less, further preferably 100 ppm or less, and particularly preferably 10 ppm or less. As a method of removing ammonia, a reaction distillation method, a method using inert gas, membrane separation, a method involving adsorptive separation, and the like can be applied. For example, the reaction distillation method is a method of separating ammonia, which has been successively generated as a result of the reaction, in a gaseous state by distillation. In order to increase the distillation efficiency of ammonia, distillation can be carried out, while boiling a solvent or the hydroxy compound. In addition, the method using inert gas is a method of accompanying ammonia successively generated as a result of the reaction in a gaseous state with inert gas to separate the ammonia from the reaction system. A method of using inert gas such as nitrogen, helium, argon, carbon dioxide, methane, ethane or propane, singly or in combination, and introducing the inert gas into the reaction system, is preferable. These methods of removing ammonia from the reaction system may be applied, either singly or in combination of multiple types of methods.

In the present reaction, for the purpose of increasing the reaction rate for example, a catalyst can be used. For example, the catalysts exemplified in the above step (A) can be used. In the case of using such a catalyst, the amount used is not particularly limited. The catalyst can be used at a stoichiometric ratio of 0.0001:1 to 100:1 based on the amount of the ureido group of the compound having the ureido group.

The reaction time (which is a retention time, when the reaction is a continuous reaction) is different depending on the composition of a reaction system, the reaction temperature, the method of removing ammonia, the reaction apparatus, the reaction pressure, and the like. It is generally 0.01 to 100 hours. The reaction time can be determined based on the amount of a compound of interest generated. For example, the reaction solution is sampled, the content of a compound of interest in the reaction solution is then quantified, and it is then confirmed that a desired yield can be achieved, so that the reaction can be terminated.

In the reaction, it is not always necessary to use a reaction solvent. However, for the purpose of facilitating the reaction operations, etc., a suitable reaction solvent can be used. As such reaction solvents, those exemplified in the above step (A) can be used.

The reaction apparatus used to carry out the present reaction and the material therefor are not particularly limited. Those exemplified in the step (A) can be used.

[Method (2)]

Next, the method (2), which comprises using the carbonic acid ester represented by the above formula (8) as a carbonic acid derivative, and reacting an organic primary amine with the carbonic acid ester to produce a compound having a urea bond, will be described. In the method (2), for example, an N-substituted carbamic acid ester is generated as a result of a reaction represented by the following formula (27), and at the same time, a compound having a urea bond is generated as a result of a reaction represented by the following formula (28):

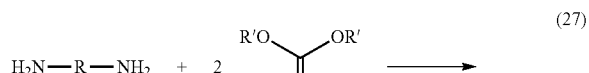

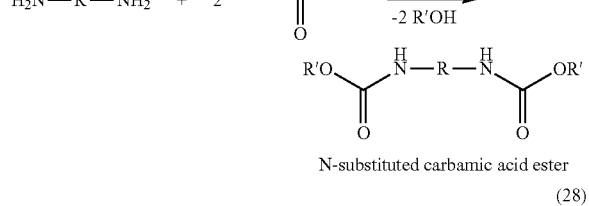

wherein

R and R' each independently represent an organic group.

In the above formulae (27) and (28), the case of using a bifunctional organic primary amine is described in order to facilitate explanation. However, the method of the present embodiment is not limited to the use of such a bifunctional organic primary amine. In addition, the processes of generating an N-substituted carbamic acid ester and a compound having a urea bond are not limited to the above formulae.

Reaction conditions are different depending on the types of compounds to be reacted. The carbonic acid ester is used at a stoichiometric ratio of 1.1:1 to 1000:1 based on the amino group of the organic primary amine. In order to increase the reaction rate to complete the reaction at an early stage, an excessive amount of the carbonic acid ester is preferably used based on the amino group of the organic primary amine. If taking into consideration the size of the reaction vessel, the carbonic acid ester is used at a stoichiometric ratio, more preferably from 2:1 to 100:1, and further preferably from 2.5:1 to 30:1, based on the amino group of the organic primary amine. The reaction temperature is generally in a range of an ordinary temperature (20° C.) to 200° C. A high temperature is preferably applied in order to increase the reaction rate. On the other hand, there is a case in which an unfavorable reaction occurs at a high temperature. Thus, the reaction temperature is preferably in a range of 50° C. to 150° C. In order to keep the reaction temperature constant, the above described reaction vessel may be equipped with a known cooling device and/or heating device. The reaction pressure is different depending on the types of compounds used or the reaction temperature. It may be any one of a reduced pressure, an ordinary pressure and a compressed pressure, and it is generally in a range of 20 to $1 \times 10^6$ Pa. The reaction time (which is a retention time, when the reaction is a continuous reaction) is not particularly limited. It is generally 0.001 to 50 hours, preferably 0.01 to 10 hours, and more preferably 0.1 to 5 hours. Otherwise, it is also possible that the reaction solution is analyzed, that it is then confirmed that the amount of the N-substituted carbamic acid ester generated and/or the amount of the compound having the urea bond generated are in desired ranges, and that the reaction is then terminated.

In the present reaction, a catalyst can be used, as necessary. Examples of such a catalyst that can be used herein include: organic metal compounds and inorganic metal compounds, such as tin, lead, copper, and titanium; and basic catalysts, such as the alcoholates of alkali metals and alkali earth metals, which include the methylate, ethylate and butylate of lithium, sodium, potassium, calcium and barium.

In the present reaction, it is not always necessary to use a reaction solvent. However, for the purpose of facilitating the reaction operations, etc., a suitable reaction solvent can be used. The same solvents as those exemplified in the above described step (A) can be used. Also, the carbonic acid ester used in an excessive amount based on the amino group of the amine compound is preferably used as a solvent in the present reaction.

A type of a reaction apparatus used to carry out the present reaction is not particularly limited, and a known reaction vessel can be used. For example, conventionally known reaction vessels, such as an agitation tank, a pressurized agitation tank, a depressurized agitation tank, a column-type reaction vessel, a distillation column, a packed column, and a thin-film distiller, can be used in combination, as appropriate. Materials used for the reaction vessel are not particularly limited, either. Known materials can be used. Examples of the material that can be used herein include glass, stainless steel, carbon steel, Hastelloy, a glass-lined base material, and a base material coated with Teflon (registered trademark).

[Method (3)]

Next, the method (3), which comprises using a phosgene as a carbonic acid derivative, and reacting an organic primary amine with the phosgene to produce a compound having a urea bond, will be described. In the method (3), an N-substituted carbamic acid chloride is generated as a result of a reaction represented by a formula (29) as shown below, and at the same time, a compound having a urea bond is generated as a result of a reaction represented by a formula (30) as shown below, for example. Moreover, there is also a case in which an isocyanate generated by the pyrolysis of the N-substituted carbamic acid chloride coexists.

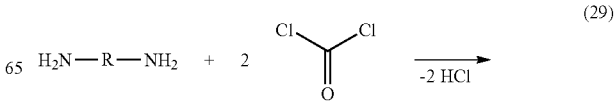

-continued

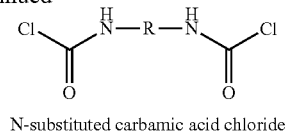

N-substituted carbamic acid chloride (30)

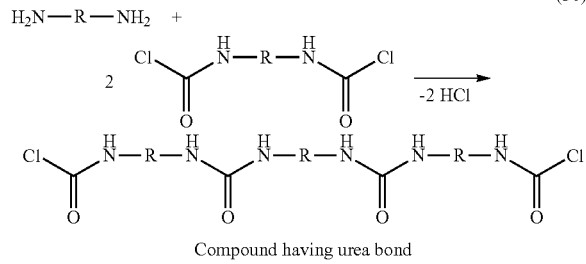

Compound having urea bond wherein

R and R' each independently represent an organic group.

In the above formulae (29) and (30), the case of using a bifunctional organic primary amine is described in order to facilitate explanation. However, the method of the present embodiment is not limited to the use of such a bifunctional organic primary amine. In addition, the processes of generating an N-substituted carbamic acid ester and a compound having a urea bond are not limited to the above formulae.

As an organic primary amine, the organic primary amine represented by the above formula (5) can be used, for example. The organic primary amine may be used in the form of a free amine, or it may be converted to a salt with organic acid, inorganic acid or the like, before subjecting it to the reaction with a phosgene. Examples of such a salt include carboxylate, carbonate, and hydrochloride.

The phosgene is used in the form of a mixture of a phosgene and a solvent. A type of a solvent used herein is not particularly limited, as long as it is inactive on a phosgene, an N-substituted carbamic acid chloride, and an isocyanate as a decomposed product of the N-substituted carbamic acid chloride. Specific examples of such a solvent include: ester-based solvents such as amyl formate, n-butyl acetate, n-amyl acetate, methylisoamyl acetate, methoxybutyl acetate, 2-ethylbutyl acetate, 2-ethylhexyl acetate, cyclohexyl acetate, methylcyclohexyl acetate, benzyl acetate, ethyl propionate, n-butyl propionate, isoamyl propionate, butyl stearate, methyl salicylate, dimethyl phthalate, and methyl benzoate; aromatic solvents such as benzene, toluene, xylene, chlorobenzene, dichlorobenzene, trichlorobenzene, nitrobenzene, naphthalene, chloronaphthalene, and dichloronaphthalene; and their mixtures. If considering time and trouble necessary for the recovery of such a solvent, the solvent used herein is more preferably identical to the after-mentioned reaction solvent.

The liquefied phosgene may be used in the reaction, directly or after regasification. The oxygen concentration in raw materials other than the phosgene used in the present embodiment is preferably 0.1 wt % or less. Thereby, the amount of tar generated as a by-product can be reduced, and thus, an isocyanation reaction can be carried out at a high yield, while the reaction product is hardly colored. As a method of removing oxygen from an organic primary amine and/or a salt of the organic primary amine, or from a reaction solvent, a method comprising blowing inert gas such as nitrogen into them and substituting oxygen dissolved therein with the inert gas, etc. can be applied. Otherwise, for example, a phosgene or a solution containing such a phosgene, which contains oxygen in a concentration of 0.1 wt % or less, is excessively supplied into the reaction system from the initial stage of the reaction, so that the dissolved oxygen contained in an organic primary amine, a salt of the organic primary amine, or a raw material used, can be removed, together with unreacted phosgene, from the reaction system.

The reaction temperature is preferably 10° C. to 300° C., more preferably 30° C. to 250° C., and further preferably 50° C. to 200° C. The reaction pressure may be a reduced pressure, an atmospheric pressure, or a compressed pressure.

As reaction solvents, the same solvents as the above described solvents used for dissolving phosgene can be used. More preferably, solvents of the same types as those of the above described solvents used for dissolving phosgene can be used. If taking into consideration the solubility of a raw material compound and a product and easy handlability, chlorobenzene, orthodichlorobenzene, and isoamyl acetate are preferably used.

The amount of the solvent used is different depending on the types of compounds to be used and reaction conditions. The solvent is used at a stoichiometric ratio of preferably from 1:1 to 200:1 based on an organic primary amine and a salt of the organic primary amine. If taking into consideration the size of a reaction vessel and solubility, the solvent is used at a stoichiometric ratio, more preferably from 2:1 to 50:1, and further preferably from 5:1 to 30:1, based on an organic primary amine and a salt of the organic primary amine.

The reaction phase may be either a homogeneous system or a heterogeneous system (a suspension). A method of keeping the reaction temperature in the system constant and carrying out an isocyanation reaction, while supplying gaseous or liquid phosgene and/or a mixture of phosgene and a solvent into the reaction system, can be applied.

A type of a reaction apparatus used to carry out the present reaction is not particularly limited, and a known reaction vessel can be used. For example, conventionally known reaction vessels, such as an agitation tank, a pressurized agitation tank, a depressurized agitation tank, a column-type reaction vessel, a distillation column, a packed column, and a thin-film distiller, can be used in combination, as appropriate.

<Polyurethane-urea Copolymer>

As the compound having the urea bond represented by the above formula (1), a polyurethane-urea copolymer can be used. The polyurethane-urea copolymer used in the present embodiment is preferably a polymer compound comprising at least one repeating unit containing a urethane group represented by the following formula (31) and at least one repeating unit containing a urea bond represented by the following formula (1):

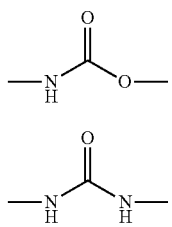

The polyurethane-urea copolymer may consist of all straight chain molecules, or may comprise straight chain molecules and some branched chain molecules. If taking into consideration flowability necessary for supplying the copolymer from the after-mentioned supply port A to the reaction distillation column, compatibility with a hydroxy compound, and the like, molecules having a small number of branched chains are preferable. If the degree of branched chains in polymer molecules is indicated with an average valence of functional groups, it is preferably 1.7 to 2.3, more preferably 1.8 to 2.2, and particularly preferably 1.9 to 2.1.

It is difficult to specifically explain the structure of the polyurethane-urea copolymer. The polyurethane-urea copolymer is a polymer produced by the reaction of at least one isocyanate ingredient, at least one diamine ingredient, and/or an aminoalcohol ingredient.

Examples of the polyol ingredient that can be used herein include:

diols such as ethylene glycol, propylene-1,2-glycol, propylene-1,3-glycol, butane-1,4-diol, butane-2,3-diol, diethylene glycol, triethylene glycol, hexane-1,6-diol, octane-1,8-diol, neopentyl glycol, 2-methyl-1,3-propanediol, and neopentyl glycol hydroxypyvalate; and polyols, in which the number of OH groups in a single molecule is 3 or greater, such as trimethylolpropane, glycerol, erythritol, pentaerythritol, trimethylolbenzene, and trishydroxyethyl isocyanurate.

In addition, the following macropolyol ingredients can also be used as diol ingredients.

As the macropolyol ingredient, at least one macropolyol ingredient selected from the group consisting of polyether polyol, polycarbonate polyol, and polyester polyol, is preferably used.

An example of such polyether polyol is a hydroxyl-containing polyether, which is prepared, for example, by polymerizing cyclic ethers in the presence of $BF_3$ or a basic catalyst, or by making a mixture of such a cyclic compound and a reactive hydrogen atom-containing starter ingredient, or successively performing an addition reaction of them.

Examples of the above described cyclic ether include ethylene oxide, propylene oxide, butylene oxide, tetrahydrofuran, styrene oxide, and epichlorohydrin. Examples of the reactive hydrogen atom-containing starter ingredient include alcohol and amine or aminoalcohol, such as water, ethylene glycol, propylene-1,2-glycol, or propylene-1,3-glycol.

Of these substances, ethylene oxide, propylene oxide, tetrahydrofuran, and a polyether based on a mixture of these cyclic ethers are preferable.

Polycarbonate polyol is preferably obtained by the reaction of a carboxylic acid derivative with polyol.

Examples of the above described carboxylic acid derivative include diphenyl carbonate, dimethyl carbonate, and phosgene. The above described polyol is preferably diol. Examples of such diol include ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethylpentane-1,3-diol, di-, tri- or tetra-ethylene glycol, dipropylene glycol, polypropylene glycol, dibutylene glycol, polybutylene glycol, bisphenol A, tetrabromobisphenol A, and lactone-modified diol.

The polyester polyol is preferably a reaction product from the reaction of polyhydric alcohol (preferably, divalent alcohol) with polybasic (preferably, dibasic) polycarboxylic acid.

The polycarboxylic acid may be aliphatic, alicyclic, aromatic, and/or heterocyclic polycarboxylic acid. In an appropriate case, the polycarboxylic acid may be substituted with, for example, a halogen atom, and/or it may be unsaturated. Among others, aliphatic and alicyclic dicarboxylic acids are preferable. Specific examples include succinic acid, adipic acid, azelaic acid, sebacic acid, phthalic acid, tetrachlorophthalic acid, isophthalic acid, terephthalic acid, tetrahydrophthalic acid, hexahydrophthalic acid, cyclohexanedicarboxylic acid, itaconic acid, glutaric acid, suberic acid, 2-methylsuccinic acid, 3,3-diethylglutaric acid, 2,2-dimethylsuccinic acid, maleic acid, malonic acid, fumaric acid, and dimethyl terephthalate. Moreover, in a case in which an acid anhydride is present, it can be used in the same manner. Examples of such an acid anhydride include maleic anhydride, phthalic anhydride, tetrahydrophthalic anhydride, glutaric anhydride, hexahydrophthalic anhydride, and tetrachlorophthalic anhydride.

The used polyhydric alcohol is preferable diol. Preferred examples of such diol include ethylene glycol, propylene-1,2-glycol, propylene-1,3-glycol, butane-1,4-diol, butane 2,3-diol, diethylene glycol, triethylene glycol, hexane-1,6-diol, octane-1,8-diol, neopentyl glycol, 2-methyl-1,3-propanediol, and neopentylglycol hydroxypyvalate. It is also possible to use polyester diol generated from lactone, for example, from c-caprolactone.

Examples of the polyol that can be used herein include trimethylolpropane, glycerol, erythritol, pentaerythritol, trimethylolbenzene, and trishydroxyethyl isocyanurate. Of these, polyether polyol is preferably used, and polyether diol is particularly preferably used.

As isocyanate ingredients, all of aromatic, aromatic-aliphatic, aliphatic, and alicyclic isocyanates, which preferably have an average NCO valence of 2 or greater, can be used, regardless of whether they are produced by a method using phosgene or a method without using phosgene. Moreover, the isocyanate may comprise the structures of iminooxadiazinedione, isocyanurate, uretdione, urethane, allophanate, biuret, urea, oxadiazinetrione, oxazolidinone, acyl urea, and/or carbodiimide.

Examples of a compound preferable as the isocyanate ingredient include the above described isocyanate compounds having the aliphatically and/or alicyclically bound NCO group, such as bis(isocyanatoalkyl)ether, bis- and tris-(isocyanatoalkyl) benzene, toluene and xylene, propane diisocyanate, butane diisocyanate, pentane diisocyanate, hexane diisocyanate, heptane diisocyanate, octane diisocyanate, nonane diisocyanate, nonane triisocyanate, decane diisocyanate, decane triisocyanate, undecane diisocyanate, undecane triisocyanate, dodecane diisocyanate, dodecane triisocyanate, 1,3- and 1,4-bis(isocyanatomethyl)cyclohexane ($H_6$XDI), 3-isocyanatomethyl-3,5,5-trimethylcyclohexyl isocyanate (isoholon diisocyanate, IPDI), bis(4-isocyanatocyclohexyl)methane ($H_{12}$MDI), and bis(isocyanatomethyl) norbornane (NBDI). Of these, preferred examples of the isocyanate ingredient include hexamethylene diisocyanate (HDI), trimethyl-HDI (TMDI), 2-methylpentane-1,5-diisocyanate (MPDI), isoholon diisocyanate (IPDI), 1,3- and 1,4-bis(isocyanatomethyl)cyclohexane ($H_6$XDI), bis(isocyanatomethyl)norbornane (NBDI), 3(4)-isocyanatomethyl-1-methylcyclohexyl isocyanate (IMCI), and/or 4,4'-bis(isocyanatocyclohexyl)methane ($H_{12}$MDI).

A ratio between the isocyanate ingredient and the polyol ingredient in the production of the polyurethane-urea copolymer is preferably 1.0 to 4.0, more preferably 1.2 to 3.8, and particularly preferably 1.5 to 3.5, at the ratio of the stoichiometric amount of the isocyanate ingredient/the stoichiometric amount of the polyol ingredient.

Examples of the diamine ingredient include hydrazine, 1,2-ethylenediamine, 1,2- and 1,3-diaminopropane, 1,4-diaminobutane, 1,6-diaminohexane, isoholondiamine, an isomeric mixture of 2,2,4- and 2,4,4-trimethylhexamethylenediamines, 2-methylpentamethylenediamine, diethylenetriamine, 1,3- and 1,4-xylylenediamines, α,α,α', α'-tetramethyl-1,3- and -1,4-xylylenediamine and 4,4'-diaminodicyclohexylmethane, dimethylethylenediamine, 1,4-bis(aminomethyl)cyclohexane, 4,4'-diamino-3,3'-dimethyldicyclohexylmethane, and other ($C_1$-$C_4$) di- and tetra-alkyldicyclohexylmethanes, such as 4,4'-diamino-3,5-diethyl-3',5'-diisopropyldicyclohexylmethane.

Examples of the aminoalcohol ingredient include N-aminoethylethanolamine, ethanolamine, 3-aminopropanol, and neopentanolamine.

A ratio of the diamine ingredient and the aminoalcohol ingredient to the polyol ingredient in the production of the polyurethane-urea copolymer is preferably 0.05 to 3.0, more preferably 0.1 to 2.0, and particularly preferably 0.2 to 1.5, at the ratio of the stoichiometric amount of the diamine ingredient+the stoichiometric amount of the aminoalcohol ingredient/the stoichiometric amount of the polyol ingredient.

The polyurethane-urea copolymer may comprise common agents to be added to improve appearance or physical properties, such as a coloring agent, an additive and a filler.

<Hydroxy Compound: Alcohol>

Examples of the hydroxy compound used in the present embodiment include alcohol and an aromatic hydroxy compound.

<Alcohol>

In accordance with the definition of IUPAC (Rule C-201), alcohol is "a compound in which a hydroxy group binds to a saturated carbon atom (Compounds in which a hydroxy group, —OH, is attached to a saturated carbon atom: $R_3COH$)," and it is a hydroxy compound represented by the following formula (32):

(32)

wherein $R^{14}$ represents an aliphatic group containing 1 to 50 carbon atoms substituted with an f number of hydroxy groups, or an aliphatic group containing 7 to 50 carbon atoms to which an aromatic group binds;

the OH group of the alcohol represented by the formula (32) is an OH group that does not bind to an aromatic group; and f represents an integer from 1 to 5.

However, $R^{14}$ is a group having no active hydrogen other than hydroxy groups.

In the above explanation, the term "active hydrogen" is used. The term "active hydrogen" is used to mean a hydrogen atom (excluding an aromatic hydroxy group) that binds to an oxygen atom, a sulfur atom, a nitrogen atom, a silicon atom, etc., and a hydrogen atom of a terminal methine group. For example, it is hydrogen contained in an atomic group such as a —OH group, a —C(=O)OH group, a —C(=O)H group, a —SH group, a —$SO_3H$ group, a —$SO_2H$ group, a —SOH group, a —$NH_2$ group, a —NH— group, a —SiH group, and a —C≡CH group.

The hydroxy group (—OH group) is also active hydrogen. Although the hydroxy group is also contained in compounds or reaction raw materials used in the present embodiment, the hydroxy group does not have harmful effects. Thus, unless otherwise specified, the hydroxy group is excluded from groups containing active hydrogen. The term "active hydrogen" is often used in other sites in the present embodiment. In such cases, the above described definition is applied.

Examples of the $R^{14}$ include a methyl group, an ethyl group, a propyl group, a butyl group, a pentyl group, a hexyl group, a heptyl group, an octyl group, a nonyl group, a decyl group, a dodecyl group, an octadecyl group, cyclopentane, cyclohexane, cycloheptane, cyclooctane, methylcyclopentane, ethylcyclopentane, methylcyclohexane, ethylcyclohexane, propylcyclohexane, butylcyclohexane, pentylcyclohexane, hexylcyclohexane, dimethylcyclohexane, diethylcyclohexane, and dibutylcyclohexane.

Specific examples of alcohol having such $R^{14}$ include methanol, ethanol, propanol, butanol, pentanol, hexanol, heptanol, octanol, nonanol, decanol, dodecanol, octadecanol, cyclopentanol, cyclohexanol, cycloheptanol, cyclooctanol, methylcyclopentanol, ethylcyclopentanol, methylcyclohexanol, ethylcyclohexanol, propylcyclohexanol, butylcyclohexanol, pentylcyclohexanol, hexylcyclohexanol, dimethylcyclohexanol, diethylcyclohexanol, and dibutylcyclohexanol.

Other examples of the $R^{14}$ include a phenylmethyl group, a phenylethyl group, a phenylpropyl group, a phenylbutyl group, a phenylpentyl group, a phenylhexyl group, a phenylheptyl group, a phenyloctyl group, and a phenylnonyl group.

Specific examples of alcohol having such $R^{14}$ include phenyl methanol, phenyl ethanol, phenylpropanol, phenyl butanol, phenyl pentanol, phenyl hexanol, phenyl heptanol, phenyl octanol, and phenyl nonanol.

If considering industrial use, among the above described alcohols, alcohol having one or two alcoholic hydroxy groups (hydroxy groups directly added to carbon atoms other than an aromatic ring, which constitute a hydroxy compound) is preferable because it has low viscosity. Monoalcohol having one alcoholic hydroxy group is more preferable.

From the viewpoint of easy availability and the solubility of a raw material and a product therein, among these alcohols, alkyl alcohol containing 1 to 20 carbon atoms is preferably used.

<Aromatic Hydroxy Compound>

The hydroxy compound used in the present embodiment may be an aromatic hydroxy compound. In accordance with the definition of IUPAC (Rule C-202), the term "aromatic hydroxy compound" is used to mean phenols ("compounds having one or more hydroxy groups attached to a benzene ring or other arene ring.") It is an aromatic hydroxy compound represented by the following formula (33):

(33)

wherein ring A represents an organic group containing 6 to 50 carbon atoms, which contains an aromatic group substituted with a g number of hydroxy groups in any position at which aromaticity is maintained, and it may be a single ring, multiple rings, or a heterocyclic ring, or it may also be substituted with another substituent; and g represents an integer from 1 to 6.

The ring A is preferably configured to contain at least one structure selected from the group consisting of a benzene ring, a naphthalene ring, and an anthracene ring. The ring A is more preferably configured to contain one benzene ring.

As described above, the term "active hydrogen" is used to mean a hydrogen atom (excluding an aromatic hydroxy group) that binds to an oxygen atom, a sulfur atom, a nitrogen atom, a silicon atom, etc., and a hydrogen atom of a terminal methine group. For example, it is hydrogen contained in an atomic group such as a —OH group, a —C(=O)OH group, a —C(=O)H group, a —SH group, a —SO$_3$H group, a —SO$_2$H group, a —SOH group, a —NH$_2$ group, a —NH— group, a —SiH group, and —C≡CH group. The aromatic hydroxy group (a —OH group directly attached to an aromatic ring) is also active hydrogen. Although the aromatic hydroxy group is also contained in compounds or reaction raw materials used in the present embodiment, the aromatic hydroxy group does not have harmful effects. Thus, the aromatic hydroxy group is excluded from groups containing active hydrogen.

The hydroxy group attached to the aromatic group of the ring A means a hydroxy group attached to the carbon atom of the aromatic group of the ring A. The number of the hydroxy groups is an integer from 1 to 6, preferably from 1 to 3, more preferably from 1 or 2, and further preferably 1 (that is, g=1).

Also, the hydroxy group used in the present embodiment is preferably an aromatic hydroxy compound represented by the following formula (34):

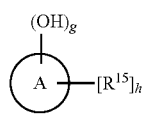

(34)

wherein ring A represents an aromatic ring selected from a benzene ring, a naphthalene ring, and an anthracene ring;

$R^{15}$ represents a group substituted in any given position at which the aromaticity of the ring A is maintained; g represents an integer from 1 to 6; h represents an integer of 6−g when the ring A is a benzene ring, or an integer of 8−g when the ring A is a naphthalene ring, or an integer of 10−g when the ring A is an anthracene ring.

In the formula (34), the OH group is substituted in any given position at which aromaticity is maintained. In addition, if there are a plurality of $R^{15}$s, the $R^{15}$s may be each independently substituted with the ring A, or the plurality of $R^{15}$s bind to one other to form a ring together with the ring A. The $R^{15}$ is, for example, a hydrogen atom, a halogen atom, a group selected from the group consisting of an alkyl group, a cycloalkyl group, an aryl group, an aralkyl group and an ether group (substituted and/or unsubstituted alkyl ether and/or aryl ether and/or aralkyl ether), and/or a group to which one or more groups selected from the above described group bind, and/or a group selected from groups constituted with groups, to which one or more groups selected from the above described group bind via a saturated aliphatic bond and/or an ether bond. The total number of carbon atoms in the ring A and the $R^{15}$ is preferably an integer from 6 to 50. The aryl group optionally has a hydroxy group.

As described above, the $R^{15}$ may cyclically bind to the ring A via a carbon-carbon bond and/or an ether bond.

Specific examples of such an aromatic hydroxy compound include: monosubstituted phenols such as phenol, methyl phenol, ethyl phenol, propyl phenol, butyl phenol, pentyl phenol, hexyl phenol, octyl phenol, nonyl phenol, phenoxy phenol, phenyl phenol, benzyl phenol, and cumyl phenol; disubstituted phenols such as dimethyl phenol, diethyl phenol, dipropyl phenol, dibutyl phenol, dipentyl phenol, dihexyl phenol, dioctyl phenol, dinonyl phenol, diphenoxy phenol, diphenyl phenol, dibenzyl phenol, and dicumyl phenol; trisubstituted phenols such as trimethyl phenol, triethyl phenol, tripropyl phenol, tributyl phenol, tripentyl phenol, trihexyl phenol, trioctyl phenol, trinonyl phenol, triphenoxy phenol, triphenyl phenol, tribenzyl phenol, and tricumyl phenol; and naphthol.

A more preferred aromatic hydroxy compound is an aromatic hydroxy compound represented by the following formula (35):

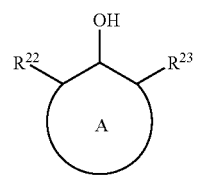

(35)

wherein ring A represents an aromatic hydrocarbon ring optionally having a substituent, and it may be either a single ring or multiple rings, $R^{22}$ and $R^{23}$ each independently represent any one group defined in the following (i) to (v), the number of carbon atoms constituting the aromatic hydroxy compound is an integer from 6 to 50, and further the $R^{22}$ and $R^{23}$ may bind to the ring A to form a ring structure:

(i) a hydrogen atom;

(ii) a halogen atom;

(iii) a group containing 1 to 44 carbon atoms, in which the atom at position α is a nitrogen atom, wherein the nitrogen atom is a secondary nitrogen atom (which represents a nitrogen atom forming a —NH— bond), and which does not contain active hydrogen (excluding hydrogen binding to the nitrogen atom at the position α);

(iv) a group containing 1 to 44 carbon atoms, in which the atom at position α is a carbon atom, wherein the carbon atom is a primary or secondary carbon atom (which represents carbon of a methyl group, carbon forming a —CH$_2$— bond), and which does not contain active hydrogen. However, when the $R^{22}$ and/or $R^{23}$ form a saturated and/or unsaturated condensed ring structure with the aromatic ring A, and the condensed ring is a 6- or less-membered ring, the carbon atom at the position α may be a tertiary or quaternary carbon atom. Examples of such a case are shown in a formula (36) and a formula (37) as shown below. In addition, when the carbon atom at the position α forms a double bond or triple bond with a position β (which represents, among atoms forming the $R^{22}$ and $R^{23}$, an atom adjacent to the atom binding to the aromatic ring of the ring A), the carbon atom at the position α may be a tertiary or quaternary carbon atom:

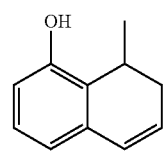

(36)

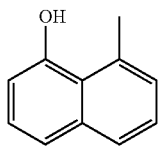

(37)

(v) a group containing 1 to 44 carbon atoms, in which the atom at position α is an oxygen atom, and which does not contain active hydrogen.

In the above formula (35), the term "the atom at position α" is used. This term "the atom at position α" means an atom adjacent to a carbon atom on the aromatic hydrocarbon ring to which the $R^{22}$ and $R^{23}$ groups bind, among atoms constituting the $R^{22}$ and $R^{23}$.

A substituent substituted with the aromatic group of the aromatic hydroxy compound represented by the above formula (35) (excluding $R^{22}$ and $R^{23}$) is selected from a hydrogen atom, a halogen atom, an aliphatic group, and an aromatic group. Examples of such a substituent include a group selected from the group consisting of a linear hydrocarbon group and a cyclic hydrocarbon group (e.g. a monocyclic hydrocarbon group, a condensed polycyclic hydrocarbon group, a crosslinked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which one or more groups selected from the above described linear hydrocarbon group and the above described cyclic hydrocarbon group bind, and a group to which the above described group binds via a covalent bond with a specific non-metal atom (carbon, oxygen, nitrogen, sulfur, or silicon). The above described covalent bond with the specific non-metal atom (carbon, oxygen, nitrogen, sulfur, or silicon) means, for example, that groups represented by the following formulae (38) to (45) bind to the above described group via a covalent bond:

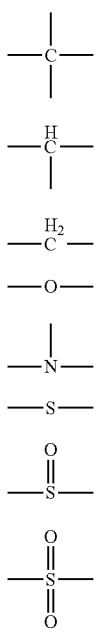

(38)

(39)

(40)

(41)

(42)

(43)

(44)

(45)

If taking into consideration the unlikeliness of side reactions, among the aforementioned substituents, examples of a substituent that can be preferably used as a substituent substituted with the aromatic group of the aromatic hydroxy compound represented by the above formula (35) (excluding $R^{22}$ and $R^{23}$) include: a group selected from the group consisting of a linear hydrocarbon group and a cyclic hydrocarbon group (a monocyclic hydrocarbon group, a condensed polycyclic hydrocarbon group, a crosslinked cyclic hydrocarbon group, a spiro hydrocarbon group, a multi-ring hydrocarbon group, and a cyclic hydrocarbon group having a side chain); and a group to which at least one group selected from the above described group binds (wherein the two groups are substituted with each other).

An example of the case of using an aromatic hydroxy compound in the method for producing the carbonyl compound of the present embodiment is a case in which an organic primary amine, a carbonic acid derivative, and an aromatic hydroxy compound are reacted to obtain an N-substituted carbamic acid ester. When such a reaction is carried out at a high temperature, it is preferable to use an aromatic hydroxy compound, in which the substituent substituted with the ring A thereof is preferably an inactive substituent. The term "inactive substituent" is used herein to mean a group that does not contain the above described active hydrogen (provided that it may have an aromatic hydroxyl group).

Examples of such a substituent substituted with the ring A, other than $R^{22}$ and $R^{23}$ include: a group selected from the group consisting of an alkyl group, a cycloalkyl group, an aryl group, an aralkyl group, and an ether group (substituted and/or unsubstituted alkyl ether and/or aryl ether and/or aralkyl ether); a group, to which one or more groups selected from the above described group bind; a group selected from groups, to which one or more groups selected from the above described group bind via a saturated aliphatic bond and/or an ether bond; and a group which is a halogen atom and in which a total of the number of carbon atoms constituting the ring A and the number of carbon atoms constituting all of the substituents substituted with the ring A can be an integer from 6 to 50.

In the above definition (iii), it is described that the nitrogen atom at position α of $R^{22}$ and $R^{23}$ may be a nitrogen atom that forms a —NH— bond. According to the definition of the above described "active hydrogen," the hydrogen atom of the —NH— bond is also active hydrogen. However, as a result of the present inventors' studies, it was found that the hydrogen atom attached to the nitrogen atom at the position α has low reactivity and thus it hardly affects the invention of the present embodiment. The present inventors have assumed that it may be due to steric hindrance around the hydroxy group.

The present inventors have found that, in an aromatic ring to which a hydroxy group binds, as defined in $R^{22}$ and $R^{23}$, a group attached to the carbon at the ortho position with respect to the carbon to which the hydroxy group binds has influence on the reactivity of an aromatic hydroxy compound in the method for producing the carbonyl compound of the present embodiment. The reason why such effects are provided has not been clarified. The present inventors have assumed that the size of steric hindrance of the groups as defined in $R^{22}$ and $R^{23}$ in the above formula (35) would have influence on the reactivity of the aromatic hydroxy compound.

In the above formula (35), examples of the ring A include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring, and an acephenanthrylene ring. More preferably, it is a structure containing at least one structure selected from a benzene ring and a naphthalene ring.

If considering industrial use, an aromatic hydroxy compound having an easily available benzene ring as a skeleton is preferable. Such an aromatic hydroxy compound is preferably an aromatic hydroxy compound represented by the following formula (46):

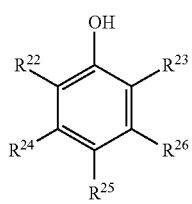

wherein
$R^{22}$ and $R^{23}$ each independently represent the group defined in the above formula (35), and $R^{24}$, $R^{25}$ and $R^{26}$ each independently represent a group selected from the group consisting of an alkyl group, a cycloalkyl group, an aryl group, an aralkyl group, and an ether group (substituted and/or unsubstituted alkyl ether and/or aryl ether and/or aralkyl ether); a group, to which one or more groups selected from the above described groups bind; a group selected from groups, to which one or more groups selected from the above described group bind via a saturated aliphatic bond and/or an ether bond; a halogen atom; or a hydrogen atom, and in which the total number of carbon atoms constituting the $R^{22}$, $R^{23}$, $R^{24}$, $R^{25}$ and $R^{26}$ is an integer from 0 to 44.

In the above formula (46), preferred $R^{24}$, $R^{25}$ and $R^{26}$ are groups each independently selected from the groups described in the following (vi) to (x):

(vi) a hydrogen atom,
(vii) a halogen atom,
(viii) a group containing 1 to 44 carbon atoms, in which the atom at position α is a carbon atom, wherein three groups attached to the carbon atom at the position α are independently selected from among an alkyl group containing 1 to 43 carbon atoms, a cycloalkyl group containing 1 to 43 carbon atoms, an alkoxy group containing 1 to 43 carbon atoms, a polyoxyalkylene alkyl ether group containing 2 to 43 carbon atoms and having no OH groups at the terminus thereof, an aryl group containing 6 to 43 carbon atoms, an aralkyl group containing 7 to 43 carbon atoms, an aralkyloxy group containing 7 to 43 carbon atoms, a group to which one or more of the above described groups bind, and a hydrogen atom,
(ix) an aryl group containing 1 to 44 carbon atoms, which is substituted with a substituent, wherein the substituent is an aryl group optionally substituted with the following 1 to 5 substituents, wherein the substituents are selected from a hydrogen atom, an alkyl group containing 1 to 38 carbon atoms, a cycloalkyl group containing 4 to 38 carbon atoms, an alkoxy group containing 1 to 38 carbon atoms, a polyoxyalkylene alkyl ether group containing 2 to 38 carbon atoms and having no OH groups at the terminus thereof, an aryl group containing 6 to 38 carbon atoms, an aralkyl group containing 7 to 38 carbon atoms, an aralkyloxy group containing 7 to 38 carbon atoms, and a group to which one or more of the above described groups bind, and (x) a group containing 1 to 44 carbon atoms, in which the atom at position α is an oxygen atom, wherein the group attached to the oxygen atom at the position α is selected from among an alkyl group containing 1 to 44 carbon atoms, a cycloalkyl group containing 1 to 44 carbon atoms, an alkoxy group containing 1 to 44 carbon atoms, a polyoxyalkylene alkyl ether group containing 2 to 44 carbon atoms and having no OH groups at the terminus thereof, an aryl group containing 6 to 44 carbon atoms, an aralkyl group containing 7 to 44 carbon atoms, an aralkyloxy group containing 7 to 44 carbon atoms, and a group to which one or more of the above described groups bind.

In the above formula (46), the term "the atom at position α" is used. This term "the atom at position α" means an atom adjacent to a carbon atom on the aromatic hydrocarbon ring to which the $R^{22}$, $R^{23}$, $R^{24}$, $R^{25}$ and $R^{26}$ groups bind, among atoms constituting the $R^{22}$, $R^{23}$, $R^{24}$, $R^{25}$ and $R^{26}$.

Specific examples of such an aromatic hydroxy compound include: monosubstituted phenols such as phenol, methyl phenol, ethyl phenol, propyl phenol, butyl phenol (excluding 2-tert-butyl phenol), phenoxy phenol, benzyl phenol, and cumyl phenol (excluding 2-cumyl phenol); disubstituted phenols such as dimethyl phenol, diethyl phenol, dipropyl phenol, diphenoxy phenol, and dibenzyl phenol; trisubstituted phenols such as trimethyl phenol, triethyl phenol, tripropyl phenol, triphenoxy phenol, triphenyl phenol, and tribenzyl phenol; and naphthol.

As described above, the above-mentioned hydroxy compound (alcohol or an aromatic hydroxy compound) can form an N-substituted carbamic acid ester, for example, by coexisting it in the step (X). The N-substituted carbamic acid ester can be used as a precursor of isocyanate. A method for producing an isocyanate from the N-substituted carbamic acid ester will be described in detail later. It is a method of subjecting the N-substituted carbamic acid ester to pyrolysis to obtain a hydroxy compound and an isocyanate.

If referring to the reaction formula, the hydroxy compound generated in the above described method is a hydroxy compound used in production of the N-substituted carbamic acid ester. That is to say, the above-defined hydroxy compound is generated as a by-product together with an isocyanate, during the pyrolysis of the N-substituted carbamic acid ester. After completion of the pyrolytic step, in one of the present embodiments, the hydroxy compound may be separated from the isocyanate by distillation, and the thus separated hydroxy compound may be then recycled as a hydroxy compound in the reaction of an organic primary amine, urea and a hydroxy compound, although it depends on situation. Accordingly, if taking into consideration the production step of the isocyanate, it is preferable to consider the separating property between the hydroxy compound and the isocyanate. It is difficult to generally define such a separating property. On the basis of the findings that, in general, if the standard boiling points of two ingredients to be separated are 10° C. or more apart from each other, they can be industrially sufficiently separated by distillation, the separating property will be defined as follows. Thus, this definition is a value that is limited to conventionally known separation means, and it is not a definition that constitutes the essence of the present embodiment.

<Compound Having Ureido Group>

In the method for producing the carbonyl compound of the present embodiment, a compound having a ureido group can be used as a precursor of the compound having the urea bond represented by the above formula (1). The compound having the ureido group is preferably a compound produced from the organic primary amine represented by the above formula (5) and urea, namely, a compound represented by the following formula (47):

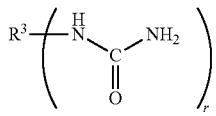

(47)

wherein
r represents an integer from 1 to 10, and
$R^3$ has the same definitions as those of the $R^3$ in the above formula (5).

The compound having the ureido group represented by the above formula (47) is a compound having a "ureido group" defined in Regulation C-971 of the Nomenclature of IUPAC. The compound having the ureido group used in the present embodiment is, for example, a compound having a ureido group, in which an r number of ureido groups (—NH—CONH$_2$) bind to an organic group containing 1 to 85 carbon atoms.

Specific examples of a preferred compound having a ureido group will be given below. "Ureido group" is a name of substituent. In the present specification, the term "N-substituted (substituent name) urea" is also used as a compound name. In order to clearly state that the nitrogen atom (N) of urea is substituted (that is, the nitrogen atom is not a —NH$_2$ group), the term "N-substituted" is used, and whether the substituent is an aromatic group or an aliphatic group is clearly described. In addition, in order to state that the compound is an organic compound, the term "organic" is also used. There are cases in which urea containing a single ureido group in a molecule thereof is referred to as "monourea," and urea containing a plurality of ureido groups in a molecule thereof is referred to as "polyurea." Even if there are a plurality of such ureido groups, ureido groups contained in the after-mentioned compound having ureido groups are N-substituted urea. Thus, as described above, a wording indicating plurality, such as poly-, di-, or tri- is placed immediately before the term "urea," so that the meanings of individual compounds can be distinguished from one another.

Throughout the descriptions of the present specification, when specific compounds are exemplified, the terms "substituted" and "mono" are not used. They are described, either according to the Nomenclature of IUPAC, or with common names.

Examples of the compound having the ureido group used in the present embodiment include an N-substituted aromatic organic monourea, an N-substituted aromatic organic polyurea, and an N-substituted aliphatic organic polyurea.

(1) N-substituted Aromatic Organic Monourea

The N-substituted aromatic organic monourea is an N-substituted aromatic organic monourea wherein, in the above formula (47), $R^3$ represents a group containing 6 to 85 carbon atoms, which contains one or more aromatic rings optionally substituted with aliphatic and/or aromatic groups, and the aromatic group in the $R^3$ is substituted with a ureido group, and r is 1. The N-substituted aromatic organic monourea is preferably an N-substituted aromatic organic monourea wherein $R^3$ represents a group containing 6 to 70 carbon atoms and r is 1. Taking into consideration flowability and the like, the N-substituted aromatic organic monourea is more preferably an N-substituted aromatic organic monourea wherein $R^3$ represents a group containing 6 to 13 carbon atoms and r is 1. It is an N-substituted aromatic organic monourea represented by the following formula (48):

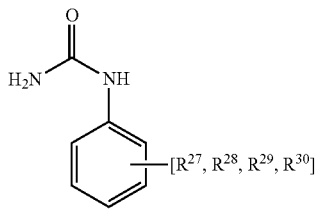

(48)

wherein
at least one of the ortho-position and/or para-position of the ureido group of the N-substituted aromatic organic monourea represented by the formula (48) is unsubstituted, and $R^{27}$ to $R^{30}$ each independently represent a group substituted in any given position at which the aromaticity of the ring is maintained.

Moreover, in the formula (48), $R^{27}$ to $R^{30}$ may bind to one another to form a ring together with the aromatic ring. For example, each of $R^{27}$ to $R^{30}$ preferably represents a hydrogen atom, or a group selected from groups constituted with groups, to which a group selected from an alkyl group, a cycloalkyl group, an aryl group and an aryl group having a hydroxy group binds via a saturated aliphatic bond and/or an ether bond, wherein the number of carbon atoms contained in such a group is an integer from 0 to 7. The total number of carbon atoms in the N-substituted aromatic organic monourea represented by the formula (48), which excludes the ureido group (—NH—CO—NH$_2$), is preferably from 6 to 13.

A preferred example of the N-substituted aromatic organic monourea represented by the formula (48) is an N-substituted aromatic organic monourea wherein $R^{27}$ to $R^{30}$ each represent a hydrogen atom or a group selected from alkyl groups such as a methyl group or an ethyl group. Examples of such an N-substituted aromatic organic monourea include N-phenyl urea, N-tolyl urea, N-dimethylphenyl urea, N-diethylphenyl urea, N-dipropylphenyl urea, N-naphthalene-ylurea, N-methylnaphthalene-ylurea, N-dimethylnaphthalene-ylurea, and N-trimethylnaphthalene-ylurea. Of these, N-phenyl urea is more preferably used.

(2) N-substituted Aromatic Organic Polyurea

The N-substituted aromatic organic polyurea is an N-substituted aromatic organic polyurea wherein, in the above formula (47), $R^3$ represents a group containing 6 to 85 carbon atoms, which contains one or more aromatic rings optionally substituted with aliphatic and/or aromatic groups, and the aromatic group in the $R^3$ is substituted with a ureido group, and r is 2 or greater. The N-substituted aromatic organic polyurea is preferably an N-substituted aromatic organic polyurea wherein $R^3$ represents a group containing 6 to 70 carbon atoms and r is 2 or greater. Taking into consideration flowability and the like, it is more preferably an N-substituted aromatic organic polyurea wherein $R^3$ contains one or more aromatic rings, wherein the aromatic ring is an aromatic group containing 6 to 13 carbon atoms optionally substituted with an alkyl group, an aryl group or an aralkyl group, a ureido group binds to the aromatic group contained in the $R^3$, and r is 2 or greater. Examples of such an N-substituted aromatic organic polyurea include N,N'-phenylene diurea, N,N'-methylphenylene diurea, N,N'-methylenediphenylene diurea, N,N'-mesitylene diurea, N,N'-biphenyl diurea, N,N'-dibenzyl diurea, N,N'-propane-diylphenylene diurea, N,N'- oxydiphenylene diurea, N,N'-diphenyl-diyl-dipropane-diyl diurea, N,N'-phenylenedimethylene diurea, N,N'-methoxyphenylene diurea, N,N'-ethoxyphenylene diurea, N,N'-naphthalene-diyl urea, N,N'-pyridine-diyldimethylene diurea, N,N'-naphthalene-diyldimethylene diurea, and polymethylenepolyphenyl polyurea represented by the following formula (49):

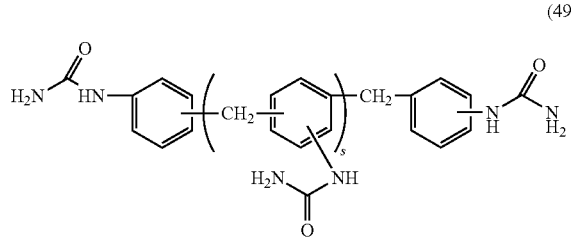

(49)

wherein
s represents an integer from 0 to 6.

(3) N-substituted Aliphatic Organic Polyurea

The N-substituted aliphatic organic polyurea is an N-substituted aliphatic organic polyurea wherein, in the above formula (47), $R^3$ represents an aliphatic group containing 1 to 85 carbon atoms optionally substituted with an aromatic group, and r is 2 or 3. The N-substituted aliphatic organic polyurea is preferably an N-substituted aliphatic organic polyurea, wherein the aliphatic group is a linear hydrocarbon group, a cyclic hydrocarbon group (including an aromatic group), or a group to which at least one group selected from the linear hydrocarbon group and the cyclic hydrocarbon group binds (e.g. a cyclic hydrocarbon group substituted with a linear hydrocarbon, a linear hydrocarbon group substituted with a cyclic hydrocarbon group, etc.). It is more preferably an N-substituted aliphatic organic polyurea, wherein $R^3$ represents an aliphatic group containing 1 to 70 carbon atoms, which is a linear hydrocarbon group, a cyclic hydrocarbon group, or a group to which at least one group selected from the linear hydrocarbon group and the cyclic hydrocarbon group binds (e.g. a cyclic hydrocarbon group substituted with a linear hydrocarbon, a linear hydrocarbon group substituted with a cyclic hydrocarbon group, etc.), and r is 2 or 3. Taking into consideration flowability necessary for industrial mass production, it is further preferably an N-substituted aliphatic organic polyurea, wherein $R^3$ represents a linear hydrocarbon group, a cyclic hydrocarbon group, or a group to which at least one group selected from the linear hydrocarbon group and the cyclic hydrocarbon group binds (e.g. a cyclic hydrocarbon group substituted with a linear hydrocarbon, a linear hydrocarbon group substituted with a cyclic hydrocarbon group, etc.), each of which is constituted with a carbon atom and a hydrogen atom and each of which contains 6 to 13 carbon atoms. That is to say, the case is an N-substituted aliphatic organic polyurea, wherein $R^3$ is a straight chain and/or branched chain alkyl group, cycloalkyl group, or group constituted with the alkyl group and the cycloalkyl group. Examples of such an N-substituted aliphatic organic polyurea include methylene diurea, 1,2-dimethylene diurea, 1,3-trimethylene diurea, 1,4-tetramethylene diurea, 1,5-pentamethylene diurea, 1,6-hexamethylene diurea, 1,8-octamethylene diurea, cyclopentane diurea, cyclohexane diurea, cycloheptane diurea, cyclooctane diurea, methylcyclopentane diurea, ethylcyclopentane diurea, methylcyclohexane diurea, ethylcyclohexane diurea, propylcyclohexane diurea, butylcyclohexane diurea, pentylcyclohexane diurea, hexylcyclohexane diurea, dimethylcyclohexane diurea, diethylcyclohexane diurea, dibutylcyclohexane diurea, 1,5,5-trimethylcyclohexane diurea, 1,5,5-triethylcyclohexane diurea, 1,5,5-tripropyl cyclohexane diurea, 1,5,5-tributylcyclohexane diurea, and 3-ureidomethyl-3,5,5-trimethylcyclohexyl urea.

<Method for Producing Compound Having Ureido Group>

A known method is applied as a method for producing the compound having the ureido group. An example of the method for producing the compound having the ureido group is a method of reacting an organic primary amine with at least one selected from the group consisting of urea, isocyanic acid and an N-unsubstituted carbamic acid ester (which will described later) to obtain a compound having a ureido group.

For example, when the compound having the ureido group is a compound having a ureido group produced by reacting an organic primary amine with urea in the presence of a hydroxy compound, the following production method can be carried out.

First, urea is used at a stoichiometric ratio of 0.5:1 to 100:1 based on the amount of the amino group of the organic primary amine. In order to increase the reaction rate to complete the reaction at an early stage, an excessive amount of urea is preferably used based on the amino group of the organic primary amine. However, if an extremely excessive amount of urea is used, the size of a reaction vessel becomes too large. Accordingly, urea is used at a stoichiometric ratio of, preferably from 1.0:1 to 100:1, more preferably from 1.5:1 to 80:1, and further preferably from 2:1 to 30:1, based on the amount of the amino group of the organic primary amine.

From the viewpoint of suppression of generation of by-products, a method of adding urea and an organic primary amine so that the total number of urea groups in the liquid phase becomes greater than the total number of the amino groups constituting the organic primary amine at an amount ratio is preferable as a reaction method. Specifically, a method of adding an organic primary amine to a mixture of a hydroxy compound and urea is preferable. Also, a method of adding a mixture of a hydroxy compound and an organic primary amine to urea may be applied. The mixture of an aromatic hydroxy compound and urea, or the mixture of an aromatic hydroxy compound and an organic primary amine, may be either a homogeneous solution or a slurry solution.

The temperature at which the above described mixture of a hydroxy compound and urea (a homogeneous solution or a slurry solution) is prepared is preferably in a range of 50° C. to 150° C. If the preparation temperature is too high, the decomposition rate of urea increases, resulting in an increase in by-products caused by urea-decomposed products in many cases.

The organic primary amine is preferably added in the state of a liquid. In general, many of the above-exemplified organic primary amines are in the state of a solid at an ordinary temperature (e.g. 20° C.). In such a case, the organic primary amine is heated to a temperature equal to or higher than the melting point thereof, so that it can be supplied in the state of a liquid. On the other hand, if the organic primary amine is supplied at an extremely high temperature, there may be a case in which side reactions, such as a heat denaturation reaction, occur due to heating. Thus, as described above, the organic primary amine is preferably supplied in the form of a mixture with an aromatic hydroxy compound, at a relatively low temperature, in the state of a liquid.

The temperature at which the present reaction is carried out is in a range of 30° C. to 250° C., and preferably of 50° C. and 200° C. As the reaction temperature decreases, generation of by-products is suppressed, and the yield is improved. However, if the reaction temperature is too low, there may be a case in which the reaction rate becomes low and the production efficiency is thereby reduced. On the other hand, if the reaction temperature is too high, there may be a case in which the decomposition rate of urea becomes high, resulting in an increase in by-products caused by urea-decomposed products. The present reaction is preferably carried out at a temperature lower than the standard boiling points of the organic primary amine, urea, and aromatic hydroxy compound used.

The present reaction is carried out under an atmospheric pressure, under a reduced pressure, or under a compressed pressure. In general, the reaction is carried out in an inert gas atmosphere, such as nitrogen, argon or helium.

The reaction time is not particularly limited. It is generally 0.001 to 100 hours, preferably 0.01 to 80 hours, and more preferably 0.1 to 50 hours. In addition, it is also possible that the reaction solution is collected, and that it is then confirmed by, for example, liquid chromatography that a desired amount of compound having a ureido group has been generated, so that the reaction can be terminated.

In the present embodiment, it is not necessary to use a catalyst in the reaction of an organic primary amine with urea. However, for the purpose of completing the reaction in a short time, decreasing the reaction temperature, etc., the use of such a catalyst is not denied. In general, since an aromatic amine has reactivity lower than that of an aliphatic amine, when such an aromatic amine is used as an organic primary amine, there is a case in which the use of a catalyst is effective. When a catalyst is used, examples of such a catalyst that can be used herein include: organic metal compounds such as tin, lead, copper, and titanium; inorganic metal compounds such as tin, lead, copper, and titanium; the alcoholates of alkali metals; and the alcoholates of alkali earth metals. Specific examples of basic catalysts, such as the alcoholates of alkali metals or the alcoholates of alkali earth metals, include the methylate, ethylate, and butylate of litium, sodium, potassium, calcium, and barium.

In the present reaction, other than the above described aromatic hydroxy compound, no reaction solvents need to be used. However, for the purpose of facilitating reaction operations, etc., a suitable solvent may be used.

Examples of such a solvent include:

alkanes such as hexane, heptane, octane, nonane, and decane;

aromatic hydrocarbons such as benzene, toluene, xylene, ethylbenzene, diisopropylbenzene, dibutylbenzene, and naphthalene;

aromatic compounds substituted with halogen or a nitro group, such as chlorobenzene, dichlorobenzene, bromobenzene, dibromobenzene, chloronaphthalene, bromonaphthalene, nitrobenzene, and nitronaphthalene;

polycyclic hydrocarbon compounds such as diphenyl, substituted diphenyl, diphenylmethane, terphenyl, anthracene, and dibenzyltoluene;

aliphatic hydrocarbons such as cyclohexane, cyclopentane, cyclooctane, and ethylcyclohexane;

alicyclic alcohols such as cyclohexanol, cyclopentanol, and cyclooctanol;

ketones such as methyl ethyl ketone and acetophenone;

esters such as dibutyl phthalate, dihexyl phthalate, dioctyl phthalate, and benzylbutyl phthalate;

ethers and thioethers, such as diphenyl ether and diphenyl sulfide; and sulfoxides such as dimethyl sulfoxide and diphenyl sulfoxide.

As the reaction apparatus, conventionally known reaction vessels, such as an agitation tank, a pressurized agitation tank, a depressurized agitation tank, a column-type reaction vessel, a distillation column, a packed column, and a thin-film distiller, can be used in combination, as appropriate. In order to keep the reaction temperature constant, a known cooling device and/or heating device may be equipped. In addition, materials used for the reaction vessel are not particularly limited. Known materials can be used.

Examples of the material that can be used herein include glass, stainless steel, carbon steel, Hastelloy, a glass-lined base material, and a base material coated with Teflon (registered trademark).

Moreover, as a method of reacting an organic primary amine with an N-unsubstituted carbamic acid ester to produce a compound having a ureido group, for example, a production method comprising the following step (a) and step (b) is applied:

step (a): a step of reacting a hydroxy compound with urea to produce an N-unsubstituted carbamic acid ester; and step (b): a step of reacting the N-unsubstituted carbamic acid ester with an organic primary amine to produce a compound having a ureido group.

As a hydroxy compound used in the step (a), alcohol and/or an aromatic hydroxy compound can be used. When the hydroxy compound is alcohol, the alcohol represented by the above formula (32) is preferable. When the hydroxy compound is an aromatic hydroxy compound, the aromatic hydroxy compound represented by the above formula (33) is preferable. The hydroxy compound used herein has a role as a reaction solvent in the step (a) and a role in reacting with urea to generate a carbamic acid ester. In particular, in the case of using an aromatic hydroxy compound, the reaction rate in the reaction of generating such a carbamic acid ester depends on the structure of the aromatic hydroxy compound, as with the reaction of generating an N-substituted carbamic acid-O-aryl ester. Accordingly, if taking into consideration reactivity with urea, the aromatic hydroxy compound represented by the above formula (35) is preferable, and the aromatic hydroxy compound represented by the above formula (46) is more preferable.

Reaction conditions for the step (a) can be determined, while referring to known methods (see, for example, Japanese Patent Laid-Open No. 5-310677).

An amount ratio between the urea and the hydroxy compound used in the reaction of the step (a) is different depending on the types of compounds to be used. Preferably, the hydroxy compound is used at a stoichiometric ratio of 5:1 or greater based on the urea. When the hydroxy compound is used at a stoichiometric ratio of 5:1 or greater based on the urea, the yield of an N-unsubstituted carbamic acid ester tends to increase, and the reaction time tends to decrease. The upper limit of the amount of the hydroxy compound to the urea is not limited. However, if an extremely excessive amount of hydroxy compound is used, it results in a decrease in the production efficiency of an N-unsubstituted carbamic acid ester. Thus, with respect to the upper limit, the hydroxy compound is generally used at the above described stoichiometric ratio of 100:1 or less based on the urea.

Since equilibrium largely lies on the raw material side in the reaction of the hydroxy compound with the urea, ammonia generated as a by-product as a result of the reaction is preferably removed from the reaction system. One of preferred embodiments is a reaction distillation method. In order to increase the efficiency of removing ammonia, the reaction can be carried out while boiling the hydroxy compound. For the same purpose, it is also possible to use a solvent having a standard boiling point lower than that of the hydroxy compound used, and to carry out the reaction at the boiling point of the solvent. The thus boiled hydroxy compound or solvent is separated from ammonia according to a known method such as distillation, and the ammonia is then removed from the system. Examples of such a solvent include: hydrocarbons such as pentane, hexane, cyclohexane, heptane, benzene, toluene, and xylene; halogenated hydrocarbons such as dichloromethane, chloroform, and carbon tetrachloride; ketones such as acetone and methyl ethyl ketone; and ethers such as tetrahydrofuran and dioxane.

As another preferred embodiment of removing ammonia generated as a by-product in the reaction system, a method using inert gas is also applied. Specifically, a method of accompanying ammonia successively generated as a result of the reaction in a gaseous state with inert gas to separate the ammonia from the reaction system. Examples of such inert gas include nitrogen, helium, argon, carbon dioxide, methane, ethane, and propane.

A further preferred embodiment of removing ammonia generated as a by-product in the reaction system is a method of adsorbing ammonia on an adsorbent to separate it from the reaction system. The type of an adsorbent used herein is not particularly limited, as long as it has ability to adsorb ammonia at a temperature used and under conditions used. Examples of such an adsorbent include silica, alumina, zeolite, and diatomaceous earth.

The reaction temperature applied in the step (a) is in a range, preferably of 120° C. to 250° C., and more preferably of 130° C. to 240° C. At a temperature equal to or higher than the above described lower limit, the reaction rate increases, and a high yield can be achieved in a short time. Thus, such a high temperature is adequate for industrial use. On the other hand, at a temperature equal to or lower than the above described upper limit, side reactions can be suppressed, and the yield can be improved.

The reaction pressure is different depending on conditions such as a composition of the reaction system, the reaction temperature, a method for removing ammonia, and a reaction apparatus. The reaction is generally carried out in a range of 0.01 kPa to 5 MPa (absolute pressure).

A type of a reaction apparatus used to carry out the present reaction is not particularly limited, and a known reaction vessel can be used. For example, conventionally known reaction vessels, such as an agitation tank, a pressurized agitation tank, a depressurized agitation tank, a column-type reaction vessel, a distillation column, a packed column, and a thin-film distiller, can be used in combination, as appropriate. Materials used for the reaction vessel are not particularly limited, either. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added, as necessary.

The use of a catalyst is not essential in the reaction of the step (a). However, a catalyst can be used for the purpose of decreasing the reaction temperature or increasing the reaction rate. Examples of such a catalyst that is preferably used herein include: rare earth elements, antimony and bismuth as single bodies, and the oxides, sulfides and chlorides of these elements; boron as a single body and boron compounds; the metals of copper elements, zinc elements, aluminum elements, carbon elements and titanium elements in the periodic table, and the oxides and sulfides thereof; and the carbides and nitrides of carbon elements, titanium elements, vanadium elements and chromium elements, other than carbon in the periodic table. In the case of using such a catalyst, an amount ratio between the catalyst and urea is not particularly limited. The catalyst is used at a weight ratio from 0.0001:1 to 0.1:1 based on the weight of the urea.

For the purpose of decreasing the viscosity of a reaction solution and/or preparing the reaction solution as a homogeneous system, a reaction solvent may be used in the reaction of the step (a). Examples of such a reaction solvent that can be preferably used herein include: alkanes such as pentane, hexane, heptane, octane, nonane, and decane; aromatic hydrocarbons and alkyl-substituted aromatic hydrocarbons, such as benzene, toluene, xylene, ethylbenzene, diisopropylbenzene, dibutylbenzene, and naphthalene; nitrile compounds such as acetonitrile and benzonitrile; aromatic compounds substituted with halogen or a nitro group, such as chlorobenzene, dichlorobenzene, bromobenzene, dibromobenzene, chloronaphthalene, bromonaphthalene, nitrobenzene, and nitronaphthalene; polycyclic hydrocarbon compounds such as diphenyl, substituted diphenyl, diphenylmethane, terphenyl, anthracene, and dibenzyltoluene; aliphatic hydrocarbons such as cyclohexane, cyclopentane, cyclooctane, and ethylcyclohexane; ketones such as methyl ethyl ketone and acetophenone; esters such as dibutyl phthalate, dihexyl phthalate, dioctyl phthalate, and benzyl butyl phthalate; ethers and thioethers, such as tetrahydrofuran, 1,4-dioxane, 1,2-dimethoxyethane, diphenyl ether, and diphenyl sulfide; ketone compounds such as acetone and methyl ethyl ketone; ester compounds such as ethyl acetate and ethyl benzoate; and sulfoxides such as dimethyl sulfoxide and diphenyl sulfoxide. Needless to say, a hydroxy compound, which is used in an excessive amount in the step (a), is also preferably used as a reaction solvent. In addition, the solvents used herein may be the same as the above described solvents that are used for removing ammonia from the reaction system.

The thus produced reaction solution of the step (a), which contains an N-unsubstituted carbamic acid ester, can be directly used in the step (b). Alternatively, the N-unsubstituted carbamic acid ester can be separated from the reaction solution, and the separated N-unsubstituted carbamic acid ester can be then used in the reaction of the step (b).

The step (b) is a step of reacting the N-unsubstituted carbamic acid ester with an organic primary amine to produce a compound having a ureido group.

The N-unsubstituted carbamic acid ester is used at a stoichiometric ratio of 1:1 to 1000:1 based on the amount of the amino group of the organic primary amine. In order to increase the reaction rate to complete the reaction at an early stage, the N-unsubstituted carbamic acid ester is preferably used in an excessive amount based on the amino group of the organic primary amine. However, if an extremely excessive amount of urea is used, the size of the reaction vessel becomes too large. Accordingly, the N-unsubstituted carbamic acid ester is used at a stoichiometric ratio of, preferably from 0.5:1 to 1000:1, more preferably from 1:1 to 1000:1, further preferably from 1.5:1 to 100:1, and particularly preferably from 2.0:1 to 30:1.

From the viewpoint of suppression of generation of by-products, as a reaction method, a method of adding an N-unsubstituted carbamic acid ester and an organic primary amine at an amount ratio such that the total number of N-unsubstituted carbamic acid esters in the liquid phase becomes greater than the total number of amino groups constituting the organic primary amine is preferable. Specifically, a method of adding an organic primary amine to a mixture of an N-unsubstituted carbamic acid ester and a hydroxy compound is preferable. Otherwise, a method of adding an organic primary amine to the mixture containing an N-unsubstituted carbamic acid ester obtained in the step (a) may also be applied. The organic primary amine may be added singly or in the form of a mixture with a hydroxy compound.

The organic primary amine is preferably added in the state of a liquid. In general, many of the above-exemplified organic primary amines are in the state of a solid at an ordinary temperature (e.g. 20° C.). In such a case, the organic primary amine is heated to a temperature equal to or higher than the melting point thereof, so that it can be supplied in the state of a liquid. On the other hand, if the organic primary amine is supplied at an extremely high temperature, there may be a case in which side reactions, such as a heat denaturation reaction, occur due to heating. Thus, as described above, the organic primary amine is preferably supplied in the form of a mixture with an aromatic hydroxy compound, at a relatively low temperature, in the state of a liquid.

The temperature at which the present reaction is carried out is in a range of 30° C. to 250° C., and preferably of 50° C. and 200° C. As the reaction temperature decreases, generation of by-products is suppressed, and the yield is improved. However, if the reaction temperature is too low, there may be a case in which the reaction rate becomes low and the production efficiency is thereby reduced. On the other hand, if the reaction temperature is too high, there may be a case in which the decomposition rate of the N-unsubstituted carbamic acid ester becomes high, resulting in an increase in by-products caused by the decomposed product of the N-unsubstituted carbamic acid ester. The present reaction is preferably carried out at a temperature lower than the standard boiling points of the organic primary amine, N-unsubstituted carbamic acid ester, and aromatic hydroxy compound used.

The present reaction is carried out under an atmospheric pressure, under a reduced pressure, or under a compressed pressure. In general, the reaction is carried out in an inert gas atmosphere, such as nitrogen, argon or helium.

The reaction time is not particularly limited. It is generally 0.001 to 100 hours, preferably 0.01 to 80 hours, and more preferably 0.1 to 50 hours. In addition, it is also possible that the reaction solution is collected, and that it is then confirmed that a desired amount of compound having a ureido group has been generated, so that the reaction can be terminated.

In the step (b), the hydroxy compound used in the step (a) can be used as a solvent in the step (b). For the purpose of facilitating reaction operations, etc., a suitable solvent may be used.

Examples of such a solvent include:

alkanes such as hexane, heptane, octane, nonane, and decane;

aromatic hydrocarbons such as benzene, toluene, xylene, ethylbenzene, diisopropylbenzene, dibutylbenzene, and naphthalene;

aromatic compounds substituted with halogen or a nitro group, such as chlorobenzene, dichlorobenzene, bromobenzene, dibromobenzene, chloronaphthalene, bromonaphthalene, nitrobenzene, and nitronaphthalene;

polycyclic hydrocarbon compounds such as diphenyl, substituted diphenyl, diphenylmethane, terphenyl, anthracene, and dibenzyltoluene;

aliphatic hydrocarbons such as cyclohexane, cyclopentane, cyclooctane, and ethylcyclohexane;

alicyclic alcohols such as cyclohexanol, cyclopentanol, and cyclooctanol;

ketones such as methyl ethyl ketone and acetophenone;

esters such as dibutyl phthalate, dihexyl phthalate, dioctyl phthalate, and benzylbutyl phthalate;

ethers and thioethers, such as diphenyl ether and diphenyl sulfide; and sulfoxides such as dimethyl sulfoxide and diphenyl sulfoxide.

As the reaction apparatus, conventionally known reaction vessels, such as an agitation tank, a pressurized agitation tank, a depressurized agitation tank, a column-type reaction vessel, a distillation column, a packed column, and a thin-film distiller, can be used in combination, as appropriate. In order to keep the reaction temperature constant, a known cooling device and/or heating device may be equipped. In addition, materials used for the reaction vessel are not particularly limited. Known materials can be used. Examples of the material that can be used herein include glass, stainless steel, carbon steel, Hastelloy, a glass-lined base material, and a base material coated with Teflon (registered trademark).

In the above described method for producing the compound having the ureido group, there is a case in which a compound having a urea bond is generated as a by-product. In such a case, the compound having the ureido compound may be separated, and the thus obtained compound having the urea bond may be used in the method for producing the carbonyl compound of the present embodiment. Otherwise, a mixture containing the compound having the urea bond may be used in the method for producing the carbonyl compound of the present embodiment.

<<Reaction of Compound Having Urea Bond with Carbonic Acid Derivative, Etc.>>

The method for producing the carbonyl compound of the present embodiment comprises a step (X) of reacting a compound having a urea bond represented by the following formula (1) with a carbonic acid derivative having a carbonyl group (—C(=O)—) under heating at a temperature equal to or higher than the thermal dissociation temperature of the urea bond to obtain the carbonyl compound.

The step (X) is preferably carried out in the coexistence of a hydroxy compound:

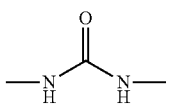

(1)

The above described method for producing a carbonyl compound using a carbonic acid derivative comprises a step (X) of reacting the compound having the urea bond represented by the above formula (1) with the carbonic acid derivative under heating at a temperature equal to or higher than the thermal dissociation temperature of the urea bond of the above described compound. The reaction mechanism of the present reaction has not yet been clarified. The present inventors have assumed as follows. In order to simplify the descriptions of the reaction, only the reaction of a urea bond portion will be described below.

First, by heating the compound having the urea bond represented by the above formula (1) at a temperature equal to or higher than the thermal dissociation temperature of the urea bond of the compound, the urea bond of the compound represented by the above formula (1) induces a thermal dissociation reaction, so that it is dissociated into a compound having an isocyanate group (—NCO group) and into a compound having an amino group (—NH$_2$ group) (the following formula (50)).

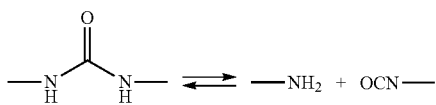
(50)

The compound having the amino group (—NH$_2$ group) reacts with a carbonic acid derivative having a carbonyl group (—C(=O)—) to obtain a carbonyl compound containing a group represented by the following formula (1-1):

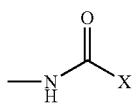
(1-1)

wherein X represents a group attached to the carbon atom of the carbonyl group (—C(=O)—) of the carbonic acid derivative.

On the other hand, the compound having the isocyanate group (—NCO group) reacts with a compound derived from a carbonic acid derivative generated as a result of the above described reaction of the compound having the amino group (—NH$_2$ group) with the carbonic acid derivative to obtain the carbonyl compound containing a group represented by the above formula (1-1).

In addition, when the reaction in the step (X) is carried out in the coexistence of a hydroxy compound, the compound having the isocyanate group (—NCO group) reacts with the hydroxy compound to obtain a carbonyl compound containing a group represented by the following formula (1-2):

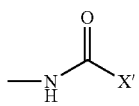
(1-2)

wherein X' represents a residue obtained by removing the hydrogen atom of a hydroxy group (—OH) from the hydroxy compound.

Hereinafter, the specific reaction mechanism of the present reaction will be described.

When the carbonic acid derivative is, for example, a carbonic acid ester represented by the following formula (51), the carbonic acid ester and a compound having an amino group are subjected to a reaction represented by the following formula (52) to generate a carbonyl compound represented by the above formula (1-1):

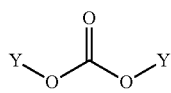
(51)

wherein
Y independently represents an aliphatic group containing 1 to 20 carbon atoms, an aromatic group containing 6 to 20 carbon atoms, or an aromatic aliphatic group containing 7 to 20 carbon atoms, each of which optionally contains an oxygen atom.

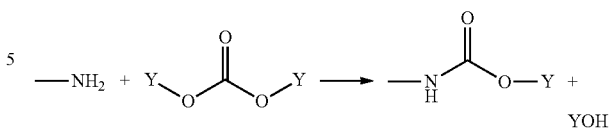
(52)

On the other hand, the compound having the isocyanate group (—NCO group) reacts with a hydroxy compound generated as a result of the reaction of the above formula (52) (YOH, the second item on the right-hand side of the above formula (52)), and/or, when the reaction is carried out in the coexistence of a hydroxy compound, with the hydroxy compound, according to a reaction represented by the following formula (53) to generate carbonyl compounds represented by the above formula (1-1) and/or the above formula (1-2):

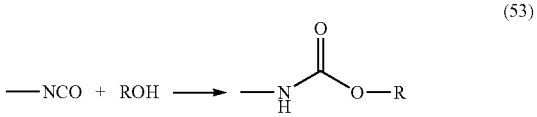
(53)

wherein
ROH represents a hydroxy compound (YOH) generated as a result of the reaction of the above formula (52), and/or when the reaction is carried out in the coexistence of a hydroxy compound, ROH represents that hydroxy compound.

Moreover, when the carbonic acid derivative is, for example, an N-unsubstituted carbamic acid ester represented by the following formula (54), the N-unsubstituted carbamic acid ester and a compound having an amino group are subjected to reactions represented by the following formula (55) and/or the following formula (56) to generate a carbonyl compound represented by the above formula (1-1):

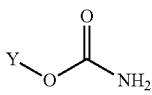
(54)

wherein
Y independently represents an aliphatic group containing 1 to 20 carbon atoms, an aromatic group containing 6 to 20 carbon atoms, or an aromatic aliphatic group containing 7 to 20 carbon atoms, each of which optionally contains an oxygen atom.

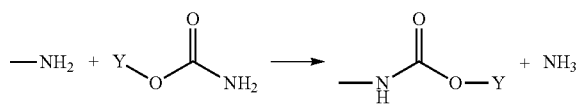
(55)

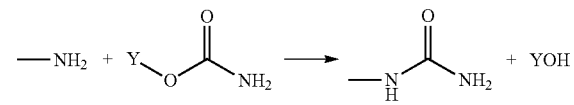
(56)

On the other hand, the compound having the isocyanate group (—NCO group) reacts with ammonia (NH$_3$) generated as a result of the reaction of the above formula (55), and/or with a hydroxy compound (YOH) generated as a result of the reaction of the above formula (56), and/or when the reaction is carried out in the coexistence of a hydroxy compound, with that hydroxy compound to generate carbonyl compounds represented by the above formula (1-1) and/or the above formula (1-2) (the following formulae (57) and (58)):

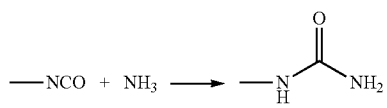

(57)

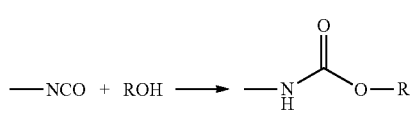

(58)

wherein

ROH represents a hydroxy compound (YOH) generated as a result of the reaction of the above formula (56), and/or when the reaction is carried out in the coexistence of a hydroxy compound, ROH represents that hydroxy compound.

Moreover, when the carbonic acid derivative is a urea, a carbonyl compound represented by the above formula (1-1) is generated as a result of a reaction represented by the following formula (59):

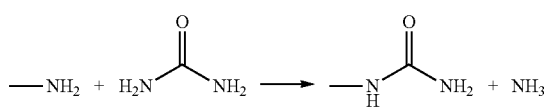

(59)

Furthermore, when the carbonic acid derivative is a phosgene, the urea compound and the compound having the amino group are subjected to a reaction represented by the following formula (60) to generate a carbonyl compound represented by the above formula (1-1):

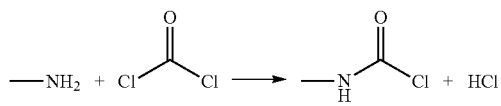

(60)

On the other hand, the compound having the isocyanate group (—NCO group) reacts with hydrogen chloride (HCl) generated as a result of the above formula (60), and/or when the reaction is carried out in the coexistence of a hydroxy compound, with that hydroxy compound to generate carbonyl compounds represented by the above formula (1-1) and/or the above formula (1-2) (the following formulae (61) and (62)):

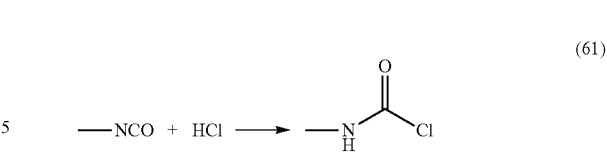

(61)

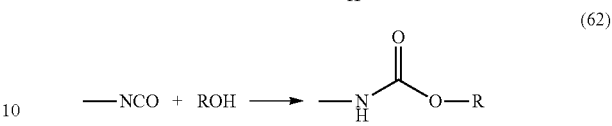

(62)

wherein

ROH represents a hydroxy compound when the reaction is carried out in the coexistence of the hydroxy compound.

As described above, it is assumed that, in the method for producing the carbonyl compound of the present embodiment, two types of compounds each having a carbonyl group represented by the above formula (1-1) are produced from a single compound having a urea bond. According to the production method of the present embodiment, by heating the compound having the urea bond at a temperature equal to or higher than the thermal dissociation temperature, the thermal dissociation reaction of the urea bond is induced, and a compound having an amino group is thereby generated, and thereafter, a carbonic acid derivative is reacted with the compound having the amino group to obtain a compound having a carbonyl group.

<Thermal Dissociation Temperature>

The term "thermal dissociation temperature" is used in the present embodiment to mean a temperature at which the thermal dissociation of the compound having the urea bond represented by the above formula (1) progresses. In general, in a method of measuring the weight of a sample as a temperature function while changing or maintaining the temperature of the sample according to certain program, it is measured as a temperature that causes a reduction in the weight of the compound. When a sample is heated at a rate of temperature rise of 10° C./min under the current of inert gas such as nitrogen, helium or argon, a temperature at which a weight reduction of 3%, and more clearly, of 5% occurs based on the weight of the added sample, is defined as a thermal dissociation temperature.

In this case, depending on the types of compounds used, the above described "weight reduction" is not only a weight reduction caused by the thermal dissociation of a urea bond (—NHCONH—) constituting the compound represented by the above formula (1), but also a weight reduction caused by the thermal dissociation of functional groups other than the urea bond constituting the above described compound. If taking into consideration the gist of the present embodiment, a weight reduction caused by the thermal dissociation of the urea bond is preferably adopted. In this case, as a method of determining which groups are thermally dissociated, the urea bond or the functional groups other than the urea bond constituting the above compound, a method comprising introducing exhaust gas from a thermogravimetric apparatus into a mass spectroscope and then analyzing ingredient contained in the exhaust gas can be applied. Moreover, depending on the types of compounds used, there is a case in which even if the thermal dissociation of the urea bond occurs, the thermal dissociation reaction is not observed in the form of a weight reduction because the molecular weight of a thermal dissociation product is large (because the boiling point of such a thermal dissociation product is high in many cases). In such a case, according to methods such as differential thermal analysis or differential scanning calorimetry, a temperature at which an endothermic reaction attended with the thermal dissociation reaction is observed can be defined as a thermal dissociation temperature. In order to ensure higher accuracy, a method of combining such differential thermal analysis or differential scanning calorimetry with a thermogravimetric apparatus can also be applied. Furthermore, the thermal dissociation reaction of the urea bond during heating is observed using a near-infrared spectrophotometer, a Raman spectrophotometer, etc., the urea bond is then quantified, and a temperature at which a weight reduction of 3%, and more clearly, of 5% occurs based on the weight of the added sample, can be defined as a thermal dissociation temperature.

<Reaction Conditions>

The reaction of the compound having the urea bond represented by the above formula (1) with a carbonic acid derivative is carried out in a state in which they are heated at a temperature equal to or higher than the thermal dissociation temperature of the urea bond of the compound having the urea bond represented by the above formula (1). The "thermal dissociation temperature" is a temperature as defined above, and it is preferably between 100° C. or higher and 350° C. or lower. If the thermal dissociation temperature is too low, the thermal dissociation reaction rate becomes low, and as a result, the reaction efficiency is deteriorated. In contrast, if the thermal dissociation temperature is too high, it induces denaturation reactions of isocyanate groups or amino groups generated as a result of the thermal dissociation reaction. Accordingly, the thermal dissociation temperature is more preferably between 120° C. or higher and 330° C. or lower, and further preferably between 140° C. or higher and 300° C. or lower.

An amount of a carbonic acid derivative used depends on the type of the carbonic acid derivative or reaction conditions. The number of the carbonic acid derivatives is preferably 5 or less based on the number of the urea bonds of the compound having urea bonds in many cases. In order to increase the reaction rate to achieve high reaction efficiency, the amount of the carbonic acid derivative is preferably large. However, if an extremely excessive amount of carbonic acid derivative is used, there may be a case in which it induces side reactions such as N-alkylation. Accordingly, the number of the carbonic acid derivatives is set at preferably 3 or less, and more preferably 2 or less, based on the number of the urea bonds of the compound having urea bonds.

The reaction of the compound having the urea bond with the carbonic acid derivative is preferably carried out in the presence of a solvent. The type of such a solvent is not particularly limited, as long as it is a compound that is able to dissolve the compound having the urea bond and the carbonic acid derivative and is stable at a reaction temperature. The same solvents as those described in the section <Compound having ureido group>, or alcohols and aromatic hydroxy compounds described in the section <Hydroxy compound>, can be used. In particular, aromatic hydroxy compounds are preferably used, in that the compound having the urea bond is highly soluble therein and in that they have a high effect of stabilizing a compound having an amino group generated as a result of the thermal dissociation reaction of the urea bond. Moreover, as described later, in a case in which an N-substituted carbamic acid ester is produced from the reaction of an organic primary amine with a carbonic acid derivative and in which, at the same time, an N-substituted carbamic acid ester is produced from the reaction of a compound having a urea bond generated as a by-product with the carbonic acid derivative, a solvent used in the reaction of the organic primary amine with the carbonic acid derivative, or a hydroxy compound that is used in an excessive amount, can be used as a solvent in the present reaction.

The present reaction is carried out under any condition of a compressed pressure, an ordinary pressure, and a reduced pressure. Moreover, the present reaction is preferably carried out in an inert gas atmosphere, such as nitrogen, argon, helium or neon.

As a reaction apparatus, conventionally known reaction vessels, such as an agitation tank, a pressurized agitation tank, a depressurized agitation tank, a column-type reaction vessel, a distillation column, a packed column, and a thin-film distiller, can be used in combination, as appropriate. In order to keep the reaction temperature constant, a known cooling device and/or heating device may be equipped. In addition, materials used for the reaction vessel are not particularly limited. Known materials can be used.

Examples of the material that can be used herein include glass, stainless steel, carbon steel, Hastelloy, a glass-lined base material, and a base material coated with Teflon (registered trademark).

<Reaction in Distillation Column>

From the viewpoint of increasing the reaction efficiency, the step (X) in the method for producing the carbonyl compound of the present embodiment is preferably carried out in a distillation column.

The type of the distillation column may be either a packed column or a plate column. It can be selected depending on a reaction form or reaction conditions.

In addition, the step (X) in the method for producing the carbonyl compound of the present embodiment is preferably carried out using a distillation column comprising a supply port A, a supply port B, and a discharge port C.

The distillation column preferably comprises a reboiler used for after-heating and vaporizing raw materials and the like to be distilled, and a condenser used for cooling, condensing and recovering a distillate, as well as a column part as a main body. The distillation column more preferably comprises a condenser. The type of the condenser comprised in the distillation column is not particularly limited. A known condenser can be used. For example, conventionally known condensers such as a multitubular cylindrical condenser, a double-tube condenser, a single-tube condenser, and an air-cooled condenser, can be used in combination, as appropriate. The condenser may be equipped inside the distillation column, or it may also be equipped outside the distillation column and may be connected with the distillation column via a pipe. Considering the type of the distillation column or condenser, a method of handling a condensate, and the like, various forms can be adopted.

Materials for the distillation column and the condenser are not particularly limited. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added to the method for producing the carbonyl compound of the present embodiment, as necessary. For example, steps and apparatuses, such as a step of removing the generated ammonia, a step of dissolving the carbonic acid derivative in the hydroxy compound, a step of melting the hydroxy compound, etc., may be added, to such an extent that they can be conceived of in the present technical field.

Hereinafter, an example of a method for producing a carbonyl compound from the compound having the urea bond, using a distillation column, will be given.

The reaction distillation column that is preferably used in the present embodiment is a distillation column comprising a supply port A, a supply port B, and a discharge port C.

Herein, the supply port A is preferably a supply port for supplying raw material ingredients containing the compound having the urea bond, and/or raw material ingredients containing a raw material for producing the compound having the urea bond (a precursor of the compound having the urea bond). Such precursors of the compound having the urea bond include the above described compounds. Among others, such precursors are preferably an organic primary amine and a carbonic acid derivative, and more preferably a compound having a ureido group represented by the following formula (4):

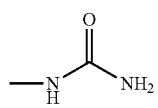

The raw material ingredients to be supplied via the supply port A further preferably contain a hydroxy compound.

The supply port B is preferably a supply port for supplying a carbonic acid derivative to be reacted with the compound having the urea bond. It is more preferable to supply a hydroxy compound via the supply port B to the distillation column.

The discharge port C is preferably a discharge port for discharging from the distillation column a mixture containing a carbonyl compound generated as a result of the reaction of the compound having the urea bond with the carbonic acid derivative under heating at a temperature equal to or higher than the thermal dissociation temperature of the urea bond.

In the method for producing the carbonyl compound of the present embodiment, the raw material ingredients to be supplied via the supply port A are combination (i) or (ii) described below, and a mixture recovered via the discharge port C preferably contains an N-substituted carbamic acid ester and a hydroxy compound:

combination (i): an organic primary amine, urea, and a hydroxy compound; or combination (ii): a hydroxy compound and a compound having a ureido group represented by the following formula (4):

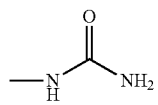

When the raw material ingredients of the above described combination (i) are supplied via at least one supply port A to the distillation column, a compound having a urea bond is generated by the method (i) of the above described method (1).

The raw material ingredients of the above described combination (i) may be supplied in the form of a mixture of an organic primary amine, urea and a hydroxy compound via one supply port A. Alternatively, the raw material ingredients of the above described combination (i) may also be supplied in the form of two types of mixtures, namely, a mixture of an organic primary amine and a hydroxy compound, and a mixture of urea and a hydroxy compound, via two or more supply ports A.

When the raw material ingredients of the above described combination (i) are supplied via the supply port A to the distillation column, as a carbonic acid derivative to be supplied via the supply port B, any one of the above described urea, carbonic acid ester, N-unsubstituted carbamic acid ester and phosgene may be used. Preferably, at least one compound selected from among urea, a carbonic acid ester and an N-unsubstituted carbamic acid ester is used. If taking into consideration easy availability for industrial use or easy recyclability after the recovery of the carbonic acid derivative from a condenser equipped in the distillation column, the same urea as that contained in the raw material ingredients of the above described combination (i) is preferably used. Moreover, the carbonic acid derivative is preferably supplied in the form of a mixture of the carbonic acid derivative and a hydroxy compound via the supply port B. If taking into consideration easy recyclability after the recovery of the hydroxy compound from a condenser equipped in the distillation column, the hydroxy compound used at that time is preferably a hydroxy compound of the same type as that contained in the raw material ingredients of the above described combination (i).

On the other hand, when the raw material ingredients of the above described combination (ii) are supplied via at least one supply port A to the distillation column, a compound having a urea bond is generated by the step (C) in the method (ii) of the above described method (1).

The compound having the ureido group represented by the above formula (4) in the raw material ingredients of the above described combination (ii) is, as described above, preferably the compound having the ureido group represented by the above formula (47), and more preferably the compound having the ureido group produced by steps including the step (B) of the above described method (ii). As stated above, there may be a case in which a compound having a urea bond is generated in the above described step (B). However, there are no problems if the compound having the urea bond is contained in the raw material ingredients.

When the raw material ingredients of the above described combination (ii) are supplied via the supply port A to the distillation column, as a carbonic acid derivative to be supplied via the supply port B, any one of the above described urea, carbonic acid ester, N-unsubstituted carbamic acid ester and phosgene may be used. Preferably, at least one compound selected from among urea, a carbonic acid ester and an N-unsubstituted carbamic acid ester is used. If taking into consideration easy availability for industrial use or easily recyclability after the recovery of the carbonic acid derivative from a condenser equipped in the distillation column, the same urea as that contained in the raw material ingredients of the above described combination (i) is preferably used. Moreover, the carbonic acid derivative is preferably supplied via the supply port B in the form of a mixture of the carbonic acid derivative and a hydroxy compound. If taking into consideration easy recyclability after the recovery of the hydroxy compound from a condenser equipped in the distillation column, the hydroxy compound used at that time is preferably a hydroxy compound of the same type as that contained in the raw material ingredients of the above described combination (i).

Moreover, in the method for producing the carbonyl compound of the present embodiment, the raw material ingredients to be supplied via the supply port A are combination (iii): an organic primary amine, a carbonic acid ester, and a hydroxy compound, and a mixture recovered via the discharge port C preferably contains an N-substituted carbamic acid ester and a hydroxy compound.

When the raw material ingredients of the above described combination (iii) are supplied via at least one supply port A to the distillation column, the compound having the urea bond is generated by the above described method (2).

The raw material ingredients to be supplied via the supply port A may be supplied in the form of a mixture of an organic primary amine and a carbonic acid ester via one supply port A. Alternatively, the organic primary amine and the carbonic acid ester may also be supplied via different supply ports A. The raw material ingredients to be supplied via the supply port A may be supplied in the form of a mixture of the raw material ingredients and a hydroxy compound. When the carbonic acid ester represented by the above formula (8) is used, for example, as a carbonic acid ester herein, the hydroxy compound used at that time is preferably a hydroxy compound represented by $Y^1OH$ and/or $Y^2OH$, from the viewpoint of reduction in the types of compounds to be handled.

When the raw material ingredients of the above described combination (iii) are supplied via at least one supply port A to the distillation column, as a carbonic acid derivative to be supplied via the supply port B, any one of the above described urea, carbonic acid ester, N-unsubstituted carbamic acid ester and phosgene may be used. The carbonic acid ester is preferably at least one compound selected from among urea, a carbonic acid ester and an N-unsubstituted carbamic acid ester, and more preferably a carbamic acid ester of the same type as that used in the raw material ingredients of the above described combination (iii). Moreover, the carbonic acid derivative is preferably supplied in the form of a mixture of the carbonic acid derivative and a hydroxy compound via the supply port B. If taking into consideration easy recyclability after the recovery of the hydroxy compound from a condenser equipped in the distillation column, as described above, when the carbonic acid ester represented by the above formula (8) is used as a carbonic acid ester, the hydroxy compound represented by $Y^1OH$ and/or $Y^2OH$ is preferably used, from the viewpoint of reduction in the types of compounds to be handled.

Furthermore, in the method for producing the carbonyl compound of the present embodiment, the raw material ingredients to be supplied via the supply port A are combination (iv): a polyurethane-urea copolymer and a hydroxy compound, and a mixture recovered via the discharge port C preferably contains an N-substituted carbamic acid ester and a hydroxy compound.

A single distillation column may comprise at least one supply port A, or may comprise a plurality of supply ports A.

The position in which the supply port A is equipped is a plate that is one or more plates higher than the lowest plate of the distillation column (one or more plates higher than the lowest plate at a theoretical plate in a packed column), preferably three or more plates higher than the lowest plate thereof (three or more plates higher than the lowest plate at a theoretical plate in a packed column), and more preferably five or more plates higher than the lowest plate thereof (five or more plates higher than the lowest plate at a theoretical plate in a packed column).

A single distillation column may comprise at least one supply port B. Otherwise, a single distillation column may comprise a plurality of supply ports B, and a carbonic acid derivative may be supplied via such a plurality of supply ports B. It is preferable to supply a mixture of a carbonic acid derivative and a hydroxy compound via the plurality of supply ports B to the distillation column.

In a distillation column, at least one supply port B is disposed in the same position as that in which the supply port A is disposed, or at a position lower than that of the supply port A (the same plate as that in which the supply port A is disposed, or a plate lower than that in which the supply port A is disposed, in a plate column; and the same theoretical plate as that in which the supply port A is disposed, or a theoretical plate lower than that in which the supply port A is disposed, in a packed column). Preferably, the supply port B is disposed at a position one or more plates lower than that of the supply port A (one or more plates lower than the supply port A at a theoretical plate in a packed column), more preferably three or more plates lower than that of the supply port A (three or more plates lower than the supply port A at a theoretical plate in a packed column), and further preferably five or more plates lower than that of the supply port A (five or more plates lower than the supply port A at a theoretical plate in a packed column).

The supply port C is disposed in the same position as that in which the supply port B is disposed, or at a position lower than that of the supply port B (the same plate as that in which the supply port B is disposed, or a plate lower than that in which the supply port B is disposed, in a plate column; and the same theoretical plate as that in which the supply port B is disposed, or a theoretical plate lower than that in which the supply port B is disposed, in a packed column). Preferably, the supply port C is disposed at a position one or more plates lower than that of the supply port B (one or more plates lower than the supply port B at a theoretical plate in a packed column), more preferably three or more plates lower than that of the supply port B (three or more plates lower than the supply port B at a theoretical plate in a packed column), and further preferably five or more plates lower than that of the supply port B (five or more plates lower than the supply port B at a theoretical plate in a packed column).

The compound to be supplied via the supply port A may be either a mixture containing a compound having a urea bond, or a mixture containing raw materials used for producing the compound having the urea bond.

Preferably, in the method for producing the carbonyl compound of the present embodiment, the step (X) is carried out using a distillation column comprising a supply port A, a supply port B, and a discharge port C, wherein the step (X) comprises a step of:

supplying raw material ingredients containing the compound having the urea bond, or raw material ingredients containing a precursor of the compound having the urea bond, to the distillation column via at least one supply port A, supplying the carbonic acid derivative to the distillation column via at least one supply port B, and recovering a generated mixture containing a carbonyl compound via at least one discharge port C disposed at a lower part of the distillation column; and the at least one supply port B is disposed at a position the same as or lower than the supply port A, the at least one discharge port C is disposed at a position the same as or lower than the supply port B, and a temperature of the distillation column at a height of the supply port B is equal to or higher than the thermal dissociation temperature of the urea bond in the compound having the urea bond.

Hereinafter, the case of supplying a mixture containing a compound having a urea bond via the supply port A to the distillation column will be first described.

The compound having the urea bond supplied via the supply port A to the distillation column is preferably supplied in the form of a mixture of the compound and a solvent. A method of melting the compound having the urea bond and then supplying it in the state of a liquid via the supply port A can also be adopted. However, the compound having the urea bond has a high melting point in many cases, and in such cases, the compound having the urea bond must be retained at a high temperature in order to melt it. When the compound having the urea bond is retained at a high temperature, unpredictable side reactions may occur in some cases. Thus, the compound having the urea bond is preferably supplied in the form of a mixture of the compound and a solvent. The type of the solvent used is not particularly limited. Examples of such a solvent include:

alkanes such as hexane, heptane, octane, nonane, and decane;

aromatic hydrocarbons such as benzene, toluene, xylene, ethylbenzene, diisopropylbenzene, dibutylbenzene, and naphthalene;

aromatic compounds substituted with halogen or a nitro group, such as chlorobenzene, dichlorobenzene, bromobenzene, dibromobenzene, chloronaphthalene, bromonaphthalene, nitrobenzene, and nitronaphthalene;

polycyclic hydrocarbon compounds such as diphenyl, substituted diphenyl, diphenylmethane, terphenyl, anthracene, and dibenzyltoluene;

aliphatic hydrocarbons such as cyclohexane, cyclopentane, cyclooctane, and ethylcyclohexane;

alicyclic alcohols such as cyclohexanol, cyclopentanol, and cyclooctanol;

ketones such as methyl ethyl ketone and acetophenone;

esters such as dibutyl phthalate, dihexyl phthalate, dioctyl phthalate, and benzylbutyl phthalate;

ethers and thioethers, such as diphenyl ether and diphenyl sulfide; and sulfoxides such as dimethyl sulfoxide and diphenyl sulfoxide. These solvents can be used depending on the types of compounds to be used (a compound having a urea bond, a carbonic acid derivative, etc.) or reaction conditions.

Moreover, as a solvent used for the compound having the urea bond, the above described hydroxy compounds (alcohol and an aromatic hydroxy compound) are more preferably used. Unexpectedly, these compounds have an effect of moderately stabilizing the urea bond of the compound having the urea bond. An aromatic hydroxy compound tends to have a higher effect of stabilizing the urea bond in many cases. The reason why the aromatic hydroxy compound has such an effect has not been clarified. The present inventors have assumed that the hydroxy compound is located close to the urea bond due to a hydrogen bond, so that it suppresses the approach of compounds each having a urea bond and it thereby suppresses a side reaction between the compounds each having the urea bond.

An amount of the solvent used is different depending on the types of compounds to be used or reaction conditions. If taking into consideration the solubility of compounds to be used, the solvent is used at a stoichiometric ratio of 1:1 or greater, and more preferably 5:1 or greater, based on the number of urea bonds in the compound having urea bonds. On the other hand, if taking into consideration the size of a reaction vessel, the solvent is used at a stoichiometric ratio of 500:1 or less, and more preferably 300:1 or less.

The carbonic acid derivative supplied via the supply port B to the distillation column is preferably supplied in the form of the mixture of the derivative and the solvent. A method of melting the carbonic acid derivative and then supplying it in the state of a liquid via the supply port B can also be adopted. However, in many cases, the carbonic acid derivative has a high melting point, and it tends to induce a pyrolytic reaction around the melting point. Thus, when the carbonic acid derivative is retained at a high temperature in order to melt it, there is a case in which the carbonic acid derivative disappears as a result of the pyrolytic reaction. Accordingly, it is preferable that a suitable solvent be used, and that a carbonic acid derivative be supplied to the reaction distillation column in the state of a solution. The type of the solvent used is not particularly limited. There can be used the same solvents as those exemplified above as solvents used for supplying the compound having the urea bond via the supply port A. Among them, a hydroxy compound is preferably used. Such a hydroxy compound has not only the effect of highly dissolving a carbonic acid derivative, but it unexpectedly has the effect of moderately stabilizing the carbonic acid derivative. An aromatic hydroxy compound tends to have a higher effect of stabilizing the carbonic acid derivative in many cases. The reason why the aromatic hydroxy compound has such an effect has not been clarified. The present inventors have assumed that the hydroxy compound is located close to the carbonyl group of the carbonic acid derivative due to a hydrogen bond, so that it suppresses the approach of carbonic acid derivatives and it thereby suppresses a side reaction between the carbonic acid derivatives. The amount of a solvent used is different depending on the types of compounds to be used or reaction conditions. The solvent is used at a stoichiometric ratio of 1:1 or greater, and more preferably 2:1 or greater, based on the amount of the carbonic acid derivative.

In the distillation column, the temperature of the position of the supply port B through which the carbonic acid derivative is to be supplied (in the same plate in a plate column, whereas in the same theoretical plate in a packed column) is set at a temperature, preferably equal to or higher than the thermal dissociation temperature of the urea bond of the compound represented by the above formula (1), more preferably 5° C. or more higher than the thermal dissociation temperature of the urea bond of the compound represented by the above formula (1), and further preferably 10° C. or more higher than the thermal dissociation temperature of the urea bond of the compound represented by the above formula (1). It is assumed that, by setting the temperature of the position of the supply port B, namely, the temperature of the position through which the carbonic acid derivative is to be supplied, at a temperature equal to or higher than the thermal dissociation temperature of the urea bond, as described above, the urea bond of the compound having the urea bond can be subjected to thermal dissociation, and as a result, the generated compound having an amino group can be reacted with the carbonic acid derivative. In the present reaction, it is important to allow a carbonic acid derivative to coexist in a system in which the urea bond is subjected to thermal dissociation, as described above. A method, which comprises setting the temperature of the position in which the supply port B is disposed in the reaction distillation column equal to or higher than the thermal dissociation temperature of the urea bond and then supplying the carbonic acid derivative via the supply port B, is one of methods that satisfy the aforementioned conditions.

The reaction pressure in the distillation column is different depending on the composition of the reaction system, the temperature, a method of removing ammonia, the reaction apparatus, etc. The reaction pressure can be set to a reduced pressure, an ordinary pressure, or a compressed pressure. In general, the reaction pressure is preferably in a range of 0.01 kPa to 10 MPa (absolute pressure). If taking into consideration facilitation of industrial production, a reduced pressure or an ordinary pressure is preferable, and the pressure is in a range of 0.01 kPa to 100 kPa (absolute pressure), more preferably 0.03 kPa to 80 kPa, and further preferably 0.05 kPa to 50 kPa.

In the reaction carried out in the distillation column, for the purpose of increasing the reaction rate for example, a catalyst can be used. Examples of such a catalyst that can be preferably used herein include: basic catalysts such as the methylate, ethylate and butylate of lithium, sodium, potassium, calcium and barium; single bodies of rare earth elements, antimony and bismuth, and the oxides, sulfides and salts of these elements; boron as a single body and boron compounds; the metals of copper elements, zinc elements, aluminum elements, carbon elements and titanium elements in the periodic table, and the metal oxides and sulfides thereof; and the carbides and nitrides of carbon elements, titanium elements, vanadium elements and chromium elements, other than carbon in the periodic table. There are many cases in which if such a catalyst is used, the catalyst must be then removed. Thus, the reaction is preferably carried out without using such catalysts. In the case of using a catalyst, it may be removed after completion of the reaction. As a method of removing the catalyst, a known method can be applied. Methods such as membrane separation, separation by distillation, or crystallization can be preferably applied.

The reaction time in the distillation column (which is a retention time in the case of a continuous reaction) is different depending on the composition of the reaction system, the reaction temperature, the reaction apparatus, the reaction pressure, and the like. It is generally 0.01 to 100 hours. The reaction time can be determined based on the amount of the carbonyl compound of interest generated. For example, the reaction solution is sampled, it is then confirmed that the carbonyl compound of interest can be obtained at a desired yield, for example, at a yield of 90% or more, and thereafter, the reaction can be terminated. When a carbonic acid derivative is supplied via a single supply port B and the reaction is then performed, if the compound of interest cannot be obtained at a sufficiently desired yield, then, a method of establishing supply ports B in multiple positions in the reaction distillation column, and then performing both the thermal dissociation reaction of the urea bond of the compound having the urea bond and the reaction of the generated amino group with the carbonic acid derivative at multiple sites may also be adopted.

As shown in the above formulae (55) and (59), when an N-unsubstituted carbamic acid ester and/or urea are used as a carbonic acid derivative(s), ammonia is generated. The generated ammonia reacts with the carbonyl compound as the compound of interest, so that the yield of the carbonyl compound is reduced in many cases. Thus, it is preferable to promptly remove such ammonia from the reaction system to prevent the ammonia from remaining in the reaction distillation column. The range of a preferred pressure is as described above. From the aforementioned viewpoint as well, the reaction pressure is preferably a reduced pressure or an ordinary pressure.

In order to increase the distillation efficiency of ammonia, the reaction is preferably carried out, while boiling a solvent. There can also be adopted a method, which comprises introducing inert gas into the reaction distillation column and then accompanying ammonia successively generated as a result of the reaction in a gaseous state with the inert gas to separate the ammonia from the reaction system. As such inert gas, nitrogen, helium, argon, carbon dioxide, methane, ethane or propane can be used singly or in combination.

As adsorbents used in the method involving adsorptive separation, adsorbents that can be used under temperature conditions in which the present reaction is carried out, such as silica, alumina, various types of zeolites, and diatomaceous earths, can be used. These methods of removing ammonia from the reaction system may be applied, either singly or in combination of multiple types of methods.

Preferably, in the method for producing the carbonyl compound of the present embodiment, the distillation column further comprises a condenser;

the method further comprises a step of condensing a portion of gas discharged from a top of the distillation column using the condenser to obtain a condensate;

a hydroxy compound is further supplied to the distillation column via the supply port A and/or the supply port B;

the carbonic acid derivative to be supplied via the supply port B is urea and/or an N-unsubstituted carbamic acid ester;

the gas discharged from the top of the distillation column contains a compound having a carbonyl group derived from the carbonic acid derivative and/or a compound having a carbonyl group derived from the compound having the urea bond, a hydroxy compound, and ammonia; and the condensate contains a compound having a carbonyl group and a hydroxy compound.

The method for producing the carbonyl compound of the present embodiment is preferably a production method, wherein the reaction distillation column comprises the above described condenser when ammonia is generated as a by-product from the reaction carried out in the distillation column, and wherein the production method further comprises: a step of discharging gas containing a compound having a carbonyl group derived from a carbonic acid derivative and/or a compound having a urea bond, a solvent, and ammonia, from the top of the reaction distillation column; and a step of condensing a portion of the gas discharged in the aforementioned step using the condenser to obtain a condensate containing the compound having the carbonyl group derived from the carbonic acid derivative and/or the compound having the urea bond and the solvent.

A handling of the gaseous ingredient containing a solvent, a compound having a carbonyl group derived from a carbonic acid derivative, and ammonia generated as a by-product from the reaction, which is generated as a result of the reaction in the distillation column, will be described below.

In the method for producing the carbonyl compound of the present embodiment, it is preferable that the gas containing a solvent, a compound having a carbonyl group derived from a carbonic acid derivative, and ammonia generated as a by-product from the reaction, which is discharged from the top of the distillation column, be introduced into the condenser equipped in the distillation column, and that a part of or an entire solvent and a part of or an entire compound having a carbonyl group derived from the carbonic acid derivative and/or the compound having the urea bond be condensed to obtain a condensate containing the compound having the carbonyl group derived from the carbonic acid derivative and/or the compound having the urea bond, and the solvent. An amount of the solvent contained in the condensate is preferably at a stoichiometric ratio of 1:1 or greater based on the amount of the compound having the carbonyl group derived from the carbonic acid derivative and/or the compound having the urea bond contained in the condensate. Moreover, when the gas containing ammonia is recovered from a condenser, the ratio between the number of carbonyl groups (—C(=O)—) and the number of ammonia molecules contained in the recovered gas (the number of carbonyl groups/the number of ammonia molecules) is preferably 1:1 or less.

The "carbonyl group" in the recovered gas means a carbonyl group of the carbonyl compound derived from the carbonic acid derivative and/or the compound having the urea bond. Thus, a carbonyl group of carbon dioxide introduced as the above described inert gas is not included.

In the present step, it is preferable that the gas containing a solvent, a compound having a carbonyl group derived from a carbonic acid derivative and/or a compound having a urea bond, and ammonia generated as a by-product from the reaction be introduced into the condenser, and that a part of or an entire solvent and the compound having the carbonyl group derived from the carbonic acid derivative and/or the compound having the urea bond be condensed. In this operation, the solvent to be condensed is used at a stoichiometric ratio of preferably 1:1 or greater based on the amount of the compound having the carbonyl group derived from the carbonic acid derivative to be condensed.

In the present embodiment, the "compound having a carbonyl group derived from the carbonic acid derivative and/or the compound having the urea bond," which is to be condensed with a condenser, is a compound having a carbonyl group that is derived from a carbonic acid derivative supplied via the supply port B and/or a compound having a urea bond supplied via the supply port A. It includes a carbonic acid derivative itself used as a raw material (an unreacted product, and/or an excess obtained when excessively used), the compound having the urea bond itself, a compound generated as a result of the reaction of a hydroxy compound used as a solvent with a carbonic acid derivative, a compound generated as a result of the reaction of the hydroxy compound with the compound having the urea bond, and a compound generated as a result of the reaction of two carbonic acid derivatives or two compounds each having a urea bond.

Specific examples of the compound having the carbonyl group derived from the carbonic acid derivative and/or the compound having the urea bond include urea, isocyanic acid, biuret, isocyanurate, a urea compound such as a urea polymer, an N-unsubstituted carbamic acid ester in which the ester group is derived from a hydroxy compound, and a carbonic acid ester in which the ester group is derived from a hydroxy compound.

The compound having the carbonyl group derived from the carbonic acid derivative and/or the compound having the urea bond can be quantified by detecting a carbonyl group contained in the compound according to a method such as infrared spectrophotometry, near-infrared spectrophotometry, Raman spectrophotometry or ultraviolet spectrophotometry. Alternatively, it can also be quantified by specifically analyzing the generated compound according to a method such as gas chromatography, liquid chromatography or NMR. Many of these compounds each having a carbonyl group derived from carbonic acid derivatives have a high melting point, and thus they tend to be easily precipitated.

In the condensation operation, the amount of the solvent to be condensed is preferably set to 1:1 or greater, at a stoichiometric ratio, based on the amount of the compound having the carbonyl group to be condensed, which is derived from the carbonic acid derivative and/or the compound having the urea bond, so that the mixture thereof can be converted to a homogeneous liquid mixture in the condenser. As a result, it becomes easy to handle the mixture, and at the same time, problems regarding adhesion, accumulation and the like of solid ingredients to the condenser can be prevented.

Moreover, as described later, determination of the amount of the solvent as described above is also effective to set the compound having the carbonyl group derived from the carbonic acid derivative and/or the compound having the urea bond to a predetermined amount or less, as described above. The amount of the solvent to be condensed is more preferably set to 2:1 or greater, and further preferably 3:1 or greater, at a stoichiometric ratio, based on the amount of the compound having the carbonyl group to be condensed, which is derived from the carbonic acid derivative and/or the compound having the urea bond. In order to set the amount of the solvent to be condensed into the above described range, based on the amount of the compound having the carbonyl group to be condensed, which is derived from the carbonic acid derivative and/or the compound having the urea bond, the condenser is preferably retained at a temperature lower than the standard boiling point of the solvent by 90° C. or more, at which the hydroxy compound is not solidified.

When gas containing ammonia is recovered from the condenser, the compound having the carbonyl group derived from the carbonic acid derivative in the recovered gas is set to a predetermined amount or less. Specifically, the ratio between the number of carbonyl groups (—C(=O)—) and the number of ammonia molecules in the recovered gas is preferably 1:1 or less, more preferably 0.5:1 or less, further preferably 0.1:1 or less, and particularly preferably 0.02 or less. The reason why the amount of the compound having the carbonyl group derived from the carbonic acid derivative in the recovered gas is set into a predetermined range is in order to prevent solid ingredients from adhering to and accumulating in a line for transferring the ammonia in the condenser.

All of the solid ingredients adhering to and accumulating in the line for transferring ammonia cannot be identified. However, as a result of studies conducted by the present inventors, it was found that many of them are compounds each having a carbonyl group. As a method of preventing such solid ingredients from adhering to and accumulating in the aforementioned line, there is a method of heating the line for transferring ammonia and decomposing such compounds each having a carbonyl group. In the studies conducted by the present inventors, decomposition products (e.g. isocyanic acid) have been polymerized or have reacted with other compounds having a carbonyl group in many cases. As a result, it has been difficult to completely prevent solid ingredients from adhering to and accumulating in the line. Moreover, it was found that, when the line is simply heated, compounds having a carbonyl group contained in the ammonia or the decomposition products thereof are quenched, particularly, at the outlet of the line for transferring the ammonia (at the part that is allowed to come into contact with air or the like), and they are thereby solidified, so that the amounts of solid ingredients adhering and accumulating thereto are significantly increased in many cases.

The present inventors have conducted intensive studies regarding the aforementioned problem. As a result, the inventors have unexpectedly found that the problem regarding adhesion and accumulation of solid ingredients can be solved by setting the amount of the compound having the carbonyl group derived from the carbonic acid derivative in the recovered gas to the aforementioned predetermined amount or less. The mechanism for providing such an effect has not yet been clarified. The present inventors have assumed that adhesion and accumulation of solid ingredients to the line is caused by the compound having the carbonyl group itself, derived from the carbonic acid derivative, or the decomposition and/or polymerization products of the compound having the carbonyl group derived from the carbonic acid derivative. Thus, the inventors have considered that the level of adhesion of the compound having the carbonyl group itself, derived from the carbonic acid derivative, or the reaction rate of decomposition and/or polymerization of the compound, is significantly decreased by setting the concentration of the carbonyl group to a predetermined concentration or less.

In order to quantify the compound having the carbonyl group derived from the carbonic acid derivative and/or the compound having the urea bond in ammonia, various types of known methods can be applied. For example, methods such as gas chromatography, liquid chromatography, NMR, near-infrared spectrophotometry or ultraviolet spectrophotometry can be applied.

Specifically, the ammonia that is in the form of gas may be directly introduced into a gas chromatography, and it may be then measured, for example (that is, the line for transferring ammonia may be directly connected with a gas chromatography, followed by measurement, or ammonia gas captured in a bag or vessel for capturing gas, such as a Tedlar bag, may be injected into a gas chromatography using gas-tight syringe or the like, followed by measurement). For instance, the compound having the carbonyl group derived from the carbonic acid derivative contained in ammonia in the recovered gas may be absorbed into water, an organic solvent, and the like, and thereafter, the amount of the compound may be measured by a method such as gas chromatography, liquid chromatography, NMR, near-infrared spectrophotometry, or ultraviolet spectrophotometry. Of these methods, there is preferably applied a method, which comprises directly introducing the recovered gas into a gas chromatography equipped with a mass spectrometer, identifying the compound having the carbonyl group, and then obtaining the amount of the compound having the carbonyl group derived from the carbonic acid derivative and/or the compound having the urea bond in the recovered gas, based on the total product of the amount of the compound having the carbonyl group and the number of the carbonyl groups.

A part of or an entire of the above described condensate may be circulated inside the reaction distillation column as a reflux solution for operating the reaction distillation column. Also, it may be supplied, for example, as a mixed solution containing a carbonic acid derivative via the supply port B, and may be recycled as a raw material for producing the carbonyl compound of the present embodiment. Otherwise, a part of or an entire of the above described condensate may be recycled as a raw material for producing the compound having the urea bond. Further, a part of or an entire of the above described condensate may also be recycled as a raw material ingredient for producing a compound having a ureido group represented by the following formula (4):

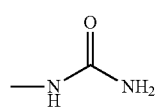

(4)

When an N-unsubstituted carbamic acid ester and/or urea are used as a carbonic acid derivative(s), and a carbonyl compound is produced, for example, according to the reactions of the above formula (52) and formula (57), there is a case in which ammonia is generated and the ammonia is contained in the condensate. In such a case, a step of removing the ammonia may be provided, separately, the amount of the ammonia may be thereby reduced to a desired concentration, and the above described recycling may be then carried out.

It is preferable that the method for producing the carbonyl compound of the present embodiment further comprise a step of allowing ammonia contained in gas discharged from the top of the distillation column to react with carbon dioxide to produce urea, and that the thus produced urea be recycled.

<<Production of N-substituted Carbamic Acid Ester by the Method of the Present Embodiment>>

In the method for producing the carbonyl compound of the present embodiment, the obtained carbonyl compound preferably contains an N-substituted carbamic acid ester. Hereinafter, production of an N-substituted carbamic acid ester by the method of the present embodiment will be described in detail.

As described above, the compound supplied via the supply port A may be either a mixture containing a compound having a urea bond, or a mixture containing a raw material for producing the compound having the urea bond. As described above, a compound having a urea bond obtained by the reaction of an organic primary amine with a carbonic acid derivative can be used as a compound having a urea bond in the method for producing the carbonyl compound of the present embodiment. In addition, the compound having the urea bond may also be a compound obtained together with an N-substituted carbamic acid ester, when an organic primary amine is reacted with a carbonic acid derivative to produce the N-substituted carbamic acid ester. Accordingly, the method for producing the carbonyl compound (which is herein an N-substituted carbamic acid ester) of the present embodiment can be a method for producing an N-substituted carbamic acid ester at a high yield by using the compound having the urea bond obtained together with the N-substituted carbamic acid ester as a compound having a urea bond used in the production method of the carbonyl compound (which is herein an N-substituted carbamic acid ester). Moreover, both the production of an N-substituted carbamic acid ester and a compound having a urea bond by the reaction of an organic primary amine with a carbonic acid derivative, and the production of the carbonyl compound (which is herein an N-substituted carbamic acid ester) of the present embodiment using the aforementioned compound having a urea bond, can be carried out in a single reaction vessel. Hereinafter, the method will be described. It is to be noted that the same applies to a case in which the carbonyl compound produced by the production method of the present embodiment is an N-substituted carbamic acid chloride.

First, a distillation column is preferably used as a reaction vessel, and the distillation column comprising a supply port A, a supply port B and a discharge port C, as described in the above section <Reaction in distillation column>, can be used. The supply port A, supply port B and discharge port C are also as described in the above section <Reaction in distillation column>.

Raw material ingredients to be supplied via each supply port equipped in the reaction distillation column are also as described in the above section <Reaction in distillation column>.

<Carbonyl Compound>

The method for producing the carbonyl compound of the present embodiment comprises a step (X) of reacting the compound having the urea bond represented by the above formula (1) with a carbonic acid derivative having a carbonyl group (—C(=O)—) under heating at a temperature equal to or higher than the thermal dissociation temperature of the urea bond to obtain the carbonyl compound. Moreover, the step (X) is preferably carried out in the coexistence of a hydroxy compound.

The carbonyl compound produced by the method for producing the carbonyl compound of the present embodiment is, for example, a compound containing a group represented by a formula (1-1) as shown below. In addition, when the step (X) is carried out in the coexistence of a hydroxy compound, a compound having a group represented by a formula (1-2) as shown below is also obtained, for example:

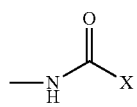
(1-1)

wherein X represents a group attached to the carbon atom of the carbonyl group (—C(=O)—) of the carbonic acid derivative;

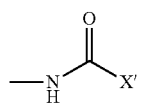
(1-2)

wherein X' represents a residue obtained by removing the hydrogen atom of a hydroxy group (—OH) from the hydroxy compound.

The above formula (1-1) depends on the carbonic acid derivative used. Specifically, it is the group of the first item on the right-hand side of the above formula (52), the group on the right-hand side of the formula (53), the group of the first item on the right-hand side of the above formula (55), the group on the right-hand side of the formula (58), the group of the first item on the right-hand side of the above formula (60), the group on the right-hand side of the formula (61), or the group on the right-hand side of the formula (62). In addition, the group of the first item on the right-hand side of the above formula (56), the group on the right-hand side of the formula (57), and the group of the first item on the right-hand side of the above formula (59) may generate an N-substituted carbamic acid ester group as a result of the reaction thereof with the coexisting hydroxyl compound, represented by the following formula (63):

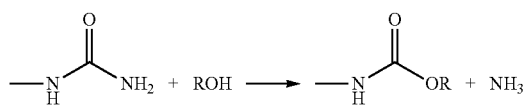
(63)

Moreover, when a phosgene is used as a carbonic acid derivative in the method for producing the carbonyl compound of the present embodiment, the obtained carbonyl compound includes a compound having a group represented by the following formula (3):

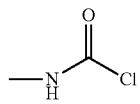
(3)

The carbonyl compound produced by the method for producing the carbonyl compound of the present embodiment is preferably an N-substituted carbamic acid ester or an N-substituted carbamic acid chloride.

<N-substituted Carbamic Acid Ester>

When the hydroxy compound is alcohol in the method for producing the carbonyl compound of the present embodiment, the obtained carbonyl compound contains an N-substituted carbamic acid-O-alkyl ester represented by a formula (7) as shown below.

Specifically, when an organic primary amine represented by a formula (5) as shown below is used and alcohol is used as a hydroxy compound, an N-substituted carbamic acid ester represented by the following formula (7) is obtained by the production method of the present embodiment:

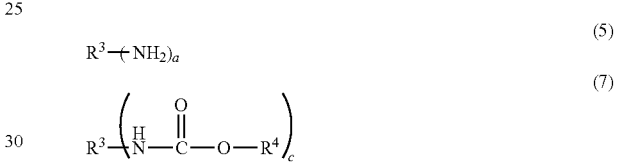

(5)

(7)

wherein $R^3$ represents an organic group containing 1 to 85 carbon atoms, $R^4$ represents a group derived from alcohol, which is a residue obtained by removing one hydroxy group from the alcohol, a represents an integer from 1 to 10, and c represents an integer from 1 to 10 (wherein c=a).

It is to be noted that the N-substituted carbamic acid ester having an ester group derived from alcohol, as shown in the above formula (7), may be referred to as an N-substituted carbamic acid-O-alkyl ester at times.

Specific examples of such an N-substituted carbamic acid-O-alkyl ester will be given below.

(1) N-Aromatic Organic Monocarbamic Acid Ester

An example of the N-substituted carbamic acid-O-alkyl ester is an N-aromatic organic monocarbamic acid ester wherein, in the above formula (7), $R^3$ represents a group containing 6 to 85 carbon atoms which contains an aromatic ring "substituted with one or more carbamic acid ester groups," and c is 1. The number of carbon atoms in the $R^3$ is preferably 6 to 70, and taking into consideration flowability and the like, it is more preferably 6 to 13.

A preferred example of the N-aromatic organic monocarbamic acid ester is an N-substituted carbamic acid mono(-O-alkyl ester) represented by the following formula (64):

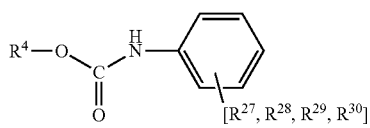
(64)

wherein
$R^{27}$, $R^{28}$, $R^{29}$ and $R^{30}$ each represent a group defined in the above formula (48).

A preferred example of such an N-substituted carbamic acid mono(-O-alkyl ester) represented by the formula (64) is an N-substituted carbamic acid mono(-O-alkyl ester) wherein $R^{27}$ to $R^{30}$ each independently represent a hydrogen atom or a group selected from alkyl groups. Examples of the alkyl group include a methyl group and an ethyl group.

(2) N-Aromatic Organic Polycarbamic Acid Ester

An example of the N-substituted carbamic acid-O-alkyl ester is an N-aromatic organic polycarbamic acid-O-alkyl ester wherein, in the formula (7), $R^3$ represents a group containing 6 to 85 carbon atoms which contains an aromatic ring "substituted with one or more carbamic acid ester groups," and c is 2 or greater. The number of carbon atoms in the $R^3$ is preferably 6 to 70, and taking into consideration flowability and the like, it is more preferably 6 to 13. The aromatic ring may be further substituted with an alkyl group, an aryl group, or an aralkyl group.

In addition, an example of the N-substituted polycarbamic acid-O-alkyl ester is a polymethylenepolyphenyl polycarbamic acid-O-alkyl ester represented by the following formula (65):

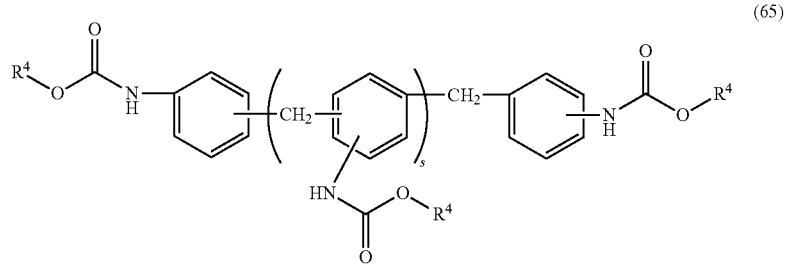

(65)

wherein
$R^4$ represents a group defined in the above formula (7), and s represents 0 or a positive integer.

(3) N-aliphatic Organic Polycarbamic Acid-O-alkyl Ester

An example of the N-substituted carbamic acid-O-alkyl ester is an N-aliphatic organic polycarbamic acid-O-alkyl ester wherein, in the formula (7), $R^3$ represents an aliphatic group containing 1 to 85 carbon atoms and c is 2 or 3. A more preferred N-substituted carbamic acid-O-alkyl ester is an N-substituted carbamic acid-O-alkyl ester wherein the aliphatic group is a linear hydrocarbon group, a cyclic hydrocarbon group, or a group to which at least one group selected from the linear hydrocarbon group and the cyclic hydrocarbon group binds (e.g. a cyclic hydrocarbon group substituted with a linear hydrocarbon, a linear hydrocarbon group substituted with a cyclic hydrocarbon group, etc.). The number of carbon atoms in the $R^3$ is more preferably 1 to 70, and taking into consideration flowability necessary for industrial mass production and the like, it is further preferably 6 to 13.

A specific example of the N-aliphatic organic polycarbamic acid-O-alkyl ester is an N-aliphatic organic polycarbamic acid-O-alkyl ester wherein $R^3$ represents a straight chain and/or branched chain alkyl group, cycloalkyl group, or group constituted with the alkyl group and the cycloalkyl group.

The specific structure of the N-substituted carbamic acid-O-alkyl ester is determined depending on the type of the organic primary amine and alcohol constituting hydroxy compound used. Thus, it is impossible to exemplify all of the specific structures. Examples of such a specific structure include N,N'-hexanediyl-di(carbamic acid methyl ester), N,N'-hexanediyl-di(carbamic acid ethyl ester), N,N'-hexanediyl-di(carbamic acid propyl ester), N,N'-hexanediyl-di(carbamic acid butyl ester), N,N'-hexanediyl-di(carbamic acid pentyl ester), N,N'-hexanediyl-di(carbamic acid hexyl ester), N,N'-hexanediyl-di(carbamic acid heptyl ester), N,N'-hexanediyl-di(carbamic acid octyl ester), N,N'-hexanediyl-di(carbamic acid nonyl ester), N,N'-hexanediyl-di(carbamic acid decyl ester), N,N'-hexanediyl-di(carbamic acid dodecyl ester), N,N'-hexanediyl-di(carbamic acid octadecyl ester), N,N'-methylenediphenylene-di(carbamic acid methyl ester), N,N'-methylenediphenylene-di(carbamic acid ethyl ester), N,N'-methylenediphenylene-di(carbamic acid propyl ester), N,N'-methylenediphenylene-di(carbamic acid butyl ester), N,N'-methylenediphenylene-di(carbamic acid pentyl ester), N,N'-methylenediphenylene-di(carbamic acid hexyl ester), N,N'-methylenediphenylene-di(carbamic acid heptyl ester), N,N'-methylenediphenylene-di(carbamic acid octyl ester), N,N'-methylenediphenylene-di(carbamic acid nonyl ester), N,N'-methylenediphenylene-di(carbamic acid decyl ester), N,N'-methylenediphenylene-di(carbamic acid dodecyl ester), N,N'-methylenediphenylene-di(carbamic acid octadecyl ester), 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester, 3-(propyloxycarbonylamino-methyl)-3,5,5-trimethylcyclohexyl carbamic acid propyl ester, 3-(butyloxycarbonylamino-methyl)-3,5,5-trimethylcyclohexyl carbamic acid butyl ester, 3-(pentyloxycarbonylamino-methyl)-3,5,5-trimethylcyclohexyl carbamic acid pentyl ester, 3-(hexyloxycarbonylamino-methyl)-3,5,5-trimethylcyclohexyl carbamic acid hexyl ester, 3-(heptyloxycarbornylamino-methyl)-3,5,5-trimethylcyclohexyl carbamic acid heptyl ester, 3-(octyloxycarbonylamino-methyl)-3,5,5-trimethylcyclohexyl carbamic acid octyl ester, 3-(nonyloxycarbonylamino-methyl)-3,5,5-trimethylcyclohexyl carbamic acid nonyl ester, 3-(decyloxycarbonylamino-methyl)-3,5,5-trimethylcyclohexyl carbamic acid decyl ester, 3-(dodecyloxycarbonylamino-methyl)-3,5,5-trimethylcyclohexyl carbamic acid dodecyl ester, 3-(octadecyloxycarbonylamino-methyl)-3,5,5-trimethylcyclohexyl carbamic acid octadecyl ester, toluene-di(carbamic acid methyl ester), toluene-di(carbamic acid ethyl ester), toluene-di(carbamic acid propyl ester), toluene-di(carbamic acid butyl ester), toluene-di(carbamic acid pentyl ester), toluene-di(carbamic acid hexyl ester), toluene-di(carbamic acid heptyl ester), toluene-di(carbamic acid octyl ester), toluene-di(carbamic acid nonyl ester), toluene-di(carbamic acid decyl ester), toluene-di(carbamic acid dodecyl ester), toluene-di(carbamic acid octadecyl ester), N,N'-methylenedicyclohexyl-di(carbamic acid methyl ester), N,N'-methylenedicyclohexyl-di(carbamic acid ethyl ester), N,N'-methylenedicyclohexyl-di(carbamic acid propyl ester), N,N'-methylenedicyclohexyl-di(carbamic acid butyl ester), N,N'- methylenedicyclohexyl-di(carbamic acid pentyl ester), N,N'-methylenedicyclohexyl-di(carbamic acid hexyl ester), N,N'-methylenedicyclohexyl-di(carbamic acid heptyl ester), N,N'-methylenedicyclohexyl-di(carbamic acid octyl ester), N,N'-methylenedicyclohexyl-di(carbamic acid nonyl ester), N,N'-methylenedicyclohexyl-di(carbamic acid decyl ester), N,N'-methylenedicyclohexyl-di(carbamic acid dodecyl ester), N,N'-methylenedicyclohexyl-di(carbamic acid octadecyl ester), N-phenyl carbamic acid methyl ester, N-phenyl carbamic acid ethyl ester, N-phenyl carbamic acid propyl ester, N-phenyl carbamic acid butyl ester, N-phenyl carbamic acid pentyl ester, N-phenyl carbamic acid hexyl ester, N-phenyl carbamic acid heptyl ester, N-phenyl carbamic acid octyl ester, N-phenyl carbamic acid nonyl ester, N-phenyl carbamic acid decyl ester, N-phenyl carbamic acid dodecyl ester, N-phenyl carbamic acid octadecyl ester, N-dimethylphenyl carbamic acid methyl ester, N-dimethylphenyl carbamic acid ethyl ester, N-dimethylphenyl carbamic acid propyl ester, N-dimethylphenyl carbamic acid butyl ester, N-dimethylphenyl carbamic acid pentyl ester, N-dimethylphenyl carbamic acid hexyl ester, N-dimethylphenyl carbamic acid heptyl ester, N-dimethylphenyl carbamic acid octyl ester, N-dimethylphenyl carbamic acid nonyl ester, N-dimethylphenyl carbamic acid decyl ester, N-dimethylphenyl carbamic acid dodecyl ester, and N-dimethylphenyl carbamic acid octadecyl ester.

On the other hand, when an aromatic hydroxy compound is used as a hydroxy compound in the production method of the present embodiment, the carbonyl compound contains an N-substituted carbamic acid ester represented by the following formula (6):

wherein
$R^3$ represents a group defined in the above formula (5),
Ar represents a group derived from an aromatic hydroxy compound, which is a residue obtained by removing one hydroxy group attached to the aromatic ring of the aromatic hydroxy compound therefrom, and
b represents an integer from 1 to 10 (wherein b=a).

In the method for producing the carbonyl compound of the present embodiment, it is preferable that the hydroxy compound be an aromatic hydroxy compound, the organic primary amine be the compound represented by the above formula (5), and the produced N-substituted carbamic acid ester be the N-substituted carbamic acid-O-aryl ester represented by the above formula (6).

It is to be noted that the N-substituted carbamic acid ester having an ester group derived from an aromatic hydroxy compound, as shown in the above formula (6), may be referred to as an N-substituted carbamic acid-O-aryl ester at times.

Hereinafter, specific examples of such an N-substituted carbamic acid-O-aryl ester will be given below.

(1) N-aromatic Organic Monocarbamic Acid Ester

An example of the N-substituted carbamic acid-O-aryl ester is an N-aromatic organic monocarbamic acid ester wherein, in the formula (6), $R^3$ represents a group containing 6 to 85 carbon atoms which contains one or more aromatic rings and b is 1. The number of carbon atoms in the $R^3$ is preferably 6 to 70, and taking into consideration flowability and the like, it is more preferably 6 to 13.

The N-aromatic organic monocarbamic acid ester is preferably an N-substituted carbamic acid mono(-O-aryl ester) represented by the following formula (65):

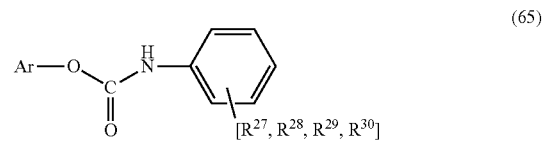

wherein
$R^{27}$, $R^{28}$, $R^{29}$ and $R^{30}$ each represent a group defined in the above formula (48).

A preferred example of the N-substituted carbamic acid mono(-O-aryl ester) represented by the formula (65) is an N-substituted carbamic acid mono(-O-aryl ester) wherein $R^{27}$ to $R^{30}$ each independently represent a hydrogen atom or a group selected from alkyl groups. Examples of the alkyl group include a methyl group and an ethyl group.

(2) N-aromatic Organic Polycarbamic Acid Ester

An example of the N-substituted carbamic acid-O-aryl ester is an N-aromatic organic polycarbamic acid-O-aryl ester wherein, in the formula (6), $R^3$ represents a group containing 6 to 85 carbon atoms which contains an aromatic ring "substituted with one or more carbamic acid ester groups," and b is 2 or greater. The number of carbon atoms in the $R^3$ is preferably 6 to 70, and taking into consideration flowability and the like, it is more preferably 6 to 13. The aromatic ring may be further substituted with an alkyl group, an aryl group, or an aralkyl group.

In addition, an example of the N-aromatic organic polycarbamic acid ester is a polymethylenepolyphenyl polycarbamic acid-O-aryl ester represented by the following formula (66):

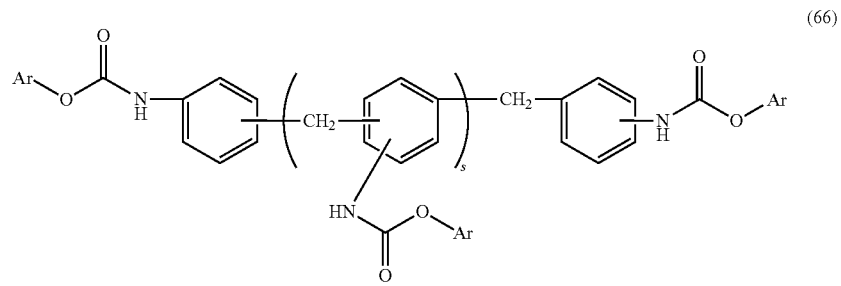

wherein

Ar represents a group defined in the above formula (6), and s represents 0 or a positive integer.

(3) N-aliphatic Organic Polycarbamic Acid-O-aryl Ester

An example of the N-substituted carbamic acid-O-aryl ester is an N-aliphatic organic polycarbamic acid-O-aryl ester wherein, in the formula (6), $R^3$ represents an aliphatic group containing 1 to 85 carbon atoms and b is 2 or 3. A more preferred N-aliphatic organic polycarbamic acid-O-aryl ester is an N-substituted carbamic acid-O-aryl ester wherein the aliphatic group is a linear hydrocarbon group, a cyclic hydrocarbon group, or a group to which at least one group selected from the linear hydrocarbon group and the cyclic hydrocarbon group binds (e.g. a cyclic hydrocarbon group substituted with a linear hydrocarbon, a linear hydrocarbon group substituted with a cyclic hydrocarbon group, etc.). The number of carbon atoms in the $R^3$ is preferably 1 to 70, and taking into consideration flowability necessary for industrial mass production and the like, it is more preferably 6 to 13.

A specific example of the N-aliphatic organic polycarbamic acid-O-aryl ester is an N-aliphatic organic polycarbamic acid-O-aryl ester wherein $R^3$ represents a straight chain and/or branched chain alkyl group, cycloalkyl group, or group constituted with the alkyl group and the cycloalkyl group.

The specific structure of the N-substituted carbamic acid-O-aryl ester is determined depending on the types of the organic primary amine and the aromatic hydroxy compound constituting a hydroxy compound used. Thus, it is impossible to exemplify all of the specific structures. Examples of such a specific structure include N,N'-hexanediyl-di(carbamic acid phenyl ester), N,N'-hexanediyl-di(carbamic acid(methylphenyl)ester), N,N'-hexanediyl-di(carbamic acid(propylphenyl)ester), N,N'-hexanediyl-di(carbamic acid(butylphenyl)ester), N,N'-hexanediyl-di(carbamic acid(pentylphenyl)ester), N,N'-hexanediyl-di(carbamic acid(heptylphenyl)ester), N,N'-hexanediyl-di(carbamic acid(octylphenyl)ester), N,N'-hexanediyl-di(carbamic acid(nonylphenyl)ester), N,N'-hexanediyl-di(carbamic acid(dodecylphenyl)ester), N,N'-hexanediyl-bis(carbamic acid(dimethylphenyl)ester), N,N'-hexanediyl-bis(carbamic acid(dipropylphenyl)ester), N,N'-hexanediyl-bis(carbamic acid(dibutylphenyl)ester), N,N'-hexanediyl-bis(carbamic acid(dipentylphenyl)ester), N,N'-hexanediyl-bis(carbamic acid(dioctadecylphenyl)ester), N,N'-methylenediphenylene-di(carbamic acid phenyl ester), N,N'-methylenediphenylene-di(carbamic acid(methylphenyl)ester), N,N'-methylenediphenylene-di(carbamic acid (ethylphenyl)ester), N,N'-methylenediphenylene-di(carbamic acid(propylphenyl)ester), N,N'-methylenediphenylene-di(carbamic acid(butylphenyl)ester), N,N'-methylenediphenylene-di(carbamic acid(pentylphenyl)ester), N,N'-methylenediphenylene-di(carbamic acid(hexylphenyl)ester), N,N'-methylenediphenylene-di(carbamic acid(heptylphenyl)ester), N,N'-methylenediphenylene-di (carbamic acid(octylphenyl)ester), N,N'-methylenediphenylene-di(carbamic acid(nonylphenyl)ester), N,N'-methylenediphenylene-di(carbamic acid(decylphenyl)ester), N,N'-methylenediphenylene-di(carbamic acid(dodecylphenyl) ester), N,N'-methylenediphenylene-di(carbamic acid (octadecylphenyl)ester), N,N'-methylenediphenylene-bis (carbamic acid(dimethylphenyl)ester), N,N'-methylenediphenylene-bis(carbamic acid(diethylphenyl) ester), N,N'-methylenediphenylene-bis(carbamic acid (dipropylphenyl)ester), N,N'-methylenediphenylene-bis (carbamic acid(dibutylphenyl)ester), N,N'-methylenediphenylene-bis(carbamic acid(dipentylphenyl) ester), N,N'-methylenediphenylene-bis(carbamic acid (dihexylphenyl)ester), N,N'-methylenediphenylene-bis (carbamic acid(diheptylphenyl)ester), N,N'-methylenediphenylene-bis(carbamic acid(dioctylphenyl) ester), N,N'-methylenediphenylene-bis(carbamic acid (dinonylphenyl)ester), N,N'-methylenediphenylene-bis (carbamic acid(didecylphenyl)ester), N,N'-methylenediphenylene-bis(carbamic acid(didodecylphenyl) ester), N,N'-methylenediphenylene-bis(carbamic acid (dioctadecylphenyl)ester), 3-(phenoxycarbonylamino-methyl)-3,5,5-trimethylcyclohexyl carbamic acid phenyl ester, 3-((methylphenoxy)carbonylamino-methyl)-3,5,5-trimethylcyclohexyl carbamic acid(methylphenyl)ester, 3-((ethylphenoxy)carbonylamino-methyl)-3,5,5-trimethylcyclohexyl carbamic acid(ethylphenyl)ester, 3-((propylphenoxy)carbonylamino-methyl)-3,5,5-trimethylcyclohexyl carbamic acid(propylphenyl)ester, 3-((butylphenoxy)carbonylamino-methyl)-3,5,5-trimethylcyclohexyl carbamic acid (butylphenyl)ester, 3-((pentylphenoxy)carbonylamino-methyl)-3,5,5-trimethylcyclohexyl carbamic acid (pentylphenyl)ester, 3-((hexylphenoxy)carbonylamino-methyl)-3,5,5-trimethylcyclohexyl carbamic acid (hexylphenyl)ester, 3-((heptylphenoxy)carbonylamino-methyl)-3,5,5-trimethylcyclohexyl carbamic acid (heptylphenyl)ester, 3-((octylphenoxy)carbonylamino-methyl)-3,5,5-trimethylcyclohexyl carbamic acid (octylphenyl)ester, 3-((nonylphenoxy)carbonylamino-methyl)-3,5,5-trimethylcyclohexyl carbamic acid (nonylphenyl)ester, 3-((decylphenoxy)carbonylamino-methyl)-3,5,5-trimethylcyclohexyl carbamic acid (decylphenyl)ester, 3-((dodecylphenoxy)carbonylamino-methyl)-3,5,5-trimethylcyclohexyl carbamic acid (dodecylphenyl)ester, 3-((octadecylphenoxy) carbonylamino-methyl)-3,5,5-trimethylcyclohexyl carbamic acid(octadecylphenyl)ester, 3-((dimethylphenoxy)carbonylamino-methyl)-3,5,5-trimethylcyclohexyl carbamic acid (dimethylphenyl)ester, 3-((diethylphenoxy)carbonylamino-methyl)-3,5,5-trimethylcyclohexyl carbamic acid (diethylphenyl)ester, 3-((dipropylphenoxy)carbonylamino-methyl)-3,5,5-trimethylcyclohexyl carbamic acid (dipropylphenyl)ester, 3-((dibutylphenoxy)carbonylamino-methyl)-3,5,5-trimethylcyclohexyl carbamic acid (dibutylphenyl)ester, 3-((dipentylphenoxy)carbonylamino-methyl)-3,5,5-trimethylcyclohexyl carbamic acid (dipentylphenyl)ester, 3-((dihexylphenoxy)carbonylamino-methyl)-3,5,5-trimethylcyclohexyl carbamic acid (dihexylphenyl)ester, 3-((diheptylphenoxy)carbonylamino-methyl)-3,5,5-trimethylcyclohexyl carbamic acid (diheptylphenyl)ester, 3-((dioctylphenoxy)carbonylamino-methyl)-3,5,5-trimethylcyclohexyl carbamic acid (dioctylphenyl)ester, 3-((dinonylphenoxy) carbonylamino-methyl)-3,5,5-trimethylcyclohexyl carbamic acid (dinonylphenyl)ester, 3-((didecylphenoxy)carbonylamino-methyl)-3,5,5-trimethylcyclohexyl carbamic acid (didecylphenyl)ester, 3-((didodecylphenoxy) carbonylamino-methyl)-3,5,5-trimethylcyclohexyl carbamic acid(didodecylphenyl)ester, 3-((dioctadecylphenoxy)carbonylamino-methyl)-3,5,5-trimethylcyclohexyl carbamic acid (dioctadecylphenyl)ester, toluene-di(carbamic acid phenyl ester), toluene-di(carbamic acid(methylphenyl)ester), toluene-di(carbamic acid(ethylphenyl)ester), toluene-di(carbamic acid(propylphenyl)ester), toluene-di(carbamic acid (butylphenyl)ester), toluene-di(carbamic acid(pentylphenyl) ester), toluene-di(carbamic acid(hexylphenyl)ester), toluene-di(carbamic acid(heptylphenyl)ester), toluene-di(carbamic acid(octylphenyl)ester), toluene-di(carbamic acid(nonylphenyl)ester), toluene-di(carbamic acid(decylphenyl)ester), toluene-di(carbamic acid(dodecylphenyl)ester), toluene-di (carbamic acid(octadecylphenyl)ester), toluene-bis(carbamic acid(dimethylphenyl)ester), toluene-bis(carbamic acid(diethylphenyl)ester), toluene-bis(carbamic acid(dipropylphenyl)ester), toluene-bis(carbamic acid(dibutylphenyl)ester), toluene-bis(carbamic acid(dipentylphenyl)ester), toluene-bis(carbamic acid(dihexylphenyl)ester), toluene-bis(carbamic acid(diheptylphenyl)ester), toluene-bis(carbamic acid(dioctylphenyl)ester), toluene-bis(carbamic acid(dinonylphenyl)ester), toluene-bis(carbamic acid(didecylphenyl) ester), toluene-bis(carbamic acid(didodecylphenyl)ester), toluene-bis(carbamic acid(dioctadecylphenyl)ester), N,N'-methylenedicyclohexyl-di(carbamic acid phenyl ester), N,N'-methylenedicyclohexyl-di(carbamic acid(methylphenyl)ester), N,N'-methylenedicyclohexyl-di(carbamic acid(ethylphenyl)ester), N,N'-methylenedicyclohexyl-di(carbamic acid(propylphenyl)ester), N,N'-methylenedicyclohexyl-di(carbamic acid(butylphenyl)ester), N,N'-methylenedicyclohexyl-di(carbamic acid(pentylphenyl)ester), N,N'-methylenedicyclohexyl-di(carbamic acid(hexylphenyl)ester), N,N'-methylenedicyclohexyl-di(carbamic acid(heptylphenyl)ester), N,N'-methylenedicyclohexyl-di(carbamic acid(octylphenyl)ester), N,N'-methylenedicyclohexyl-di(carbamic acid(nonylphenyl)ester), N,N'-methylenedicyclohexyl-di(carbamic acid(decylphenyl)ester), N,N'-methylenedicyclohexyl-di(carbamic acid(dodecylphenyl)ester), N,N'-methylenedicyclohexyl-di(carbamic acid(octadecylphenyl)ester), N,N'-methylenedicyclohexyl-bis(carbamic acid(dimethylphenyl)ester), N,N'-methylenedicyclohexyl-bis(carbamic acid(diethylphenyl)ester), N,N'-methylenedicyclohexyl-bis(carbamic acid(dipropylphenyl)ester), N,N'-methylenedicyclohexyl-bis(carbamic acid(dibutylphenyl)ester), N,N'-methylenedicyclohexyl-bis(carbamic acid(dipentylphenyl)ester), N,N'-methylenedicyclohexyl-bis(carbamic acid(dihexylphenyl)ester), N,N'-methylenedicyclohexyl-bis(carbamic acid(diheptylphenyl)ester), N,N'-methylenedicyclohexyl-bis(carbamic acid(dioctylphenyl)ester), N,N'-methylenedicyclohexyl-bis(carbamic acid(dinonylphenyl)ester), N,N'-methylenedicyclohexyl-bis(carbamic acid(didecylphenyl)ester), N,N'-methylenedicyclohexyl-bis(carbamic acid(didodecylphenyl)ester), N,N'-methylenedicyclohexyl-bis(carbamic acid(dioctadecylphenyl)ester), N-phenyl carbamic acid phenyl ester, N-phenyl carbamic acid(methylphenyl)ester, N-phenyl carbamic acid(ethylphenyl)ester, N-phenyl carbamic acid(propylphenyl)ester, N-phenyl carbamic acid(butylphenyl)ester, N-phenyl carbamic acid(pentylphenyl)ester, N-phenyl carbamic acid(hexylphenyl)ester, N-phenyl carbamic acid(heptylphenyl)ester, N-phenyl carbamic acid(octylphenyl)ester, N-phenyl carbamic acid(nonylphenyl)ester, N-phenyl carbamic acid(decylphenyl)ester, N-phenyl carbamic acid(dodecylphenyl)ester, N-phenyl carbamic acid(octadecylphenyl)ester, N-phenyl carbamic acid(dimethylphenyl)ester, N-phenyl carbamic acid(diethylphenyl)ester, N-phenyl carbamic acid(dipropylphenyl)ester, N-phenyl carbamic acid(dibutylphenyl)ester, N-phenyl carbamic acid(dipentylphenyl)ester, N-phenyl carbamic acid(dihexylphenyl)ester, N-phenyl carbamic acid(diheptylphenyl)ester, N-phenyl carbamic acid(dioctylphenyl)ester, N-phenyl carbamic acid(dinonylphenyl)ester, N-phenyl carbamic acid(didecylphenyl)ester, N-phenyl carbamic acid(didodecylphenyl)ester, N-phenyl carbamic acid(dioctadecylphenyl)ester, N-phenyl carbamic acid phenyl ester, N-phenyl carbamic acid(methylphenyl)ester, N-phenyl carbamic acid(ethyl phenyl)ester, N-phenyl carbamic acid(propylphenyl)ester, N-phenyl carbamic acid(butylphenyl)ester, N-phenyl carbamic acid(pentylphenyl)ester, N-phenyl carbamic acid(hexylphenyl)ester, N-phenyl carbamic acid(heptylphenyl)ester, N-phenyl carbamic acid(octylphenyl)ester, N-phenyl carbamic acid(nonylphenyl)ester, N-phenyl carbamic acid(decylphenyl)ester, N-phenyl carbamic acid(dodecylphenyl)ester, N-phenyl carbamic acid(octadecylphenyl)ester, N-phenyl carbamic acid(dimethylphenyl)ester, N-phenyl carbamic acid(diethylphenyl)ester, N-phenyl carbamic acid(dipropylphenyl)ester, N-phenyl carbamic acid(dibutylphenyl)ester, N-phenyl carbamic acid(dipentylphenyl)ester, N-phenyl carbamic acid(dihexylphenyl)ester, N-phenyl carbamic acid(diheptylphenyl)ester, N-phenyl carbamic acid(dioctylphenyl)ester, N-phenyl carbamic acid(dinonylphenyl)ester, N-phenyl carbamic acid(didecylphenyl)ester, N-phenyl carbamic acid(didodecylphenyl)ester, N-phenyl carbamic acid(dioctadecylphenyl)ester, N-dimethylphenyl carbamic acid phenyl ester, N-dimethylphenyl carbamic acid(methylphenyl)ester, N-dimethylphenyl carbamic acid(ethylphenyl)ester, N-dimethylphenyl carbamic acid(propyl phenyl)ester, N-dimethylphenyl carbamic acid(butylphenyl)ester, N-dimethylphenyl carbamic acid(pentylphenyl)ester, N-dimethylphenyl carbamic acid(hexylphenyl)ester, N-dimethylphenyl carbamic acid(heptylphenyl)ester, N-dimethylphenyl carbamic acid(octylphenyl)ester, N-dimethylphenyl carbamic acid(nonylphenyl)ester, N-dimethylphenyl carbamic acid(decyl phenyl)ester, N-dimethylphenyl carbamic acid(dodecylphenyl)ester, N-dimethylphenyl carbamic acid(octadecylphenyl)ester, N-dimethylphenyl carbamic acid(dimethylphenyl)ester, N-dimethylphenyl carbamic acid(diethylphenyl)ester, N-dimethylphenyl carbamic acid(dipropylphenyl)ester, N-dimethylphenyl carbamic acid(dibutylphenyl)ester, N-dimethylphenyl carbamic acid(dipentylphenyl)ester, N-dimethylphenyl carbamic acid(dihexylphenyl)ester, N-dimethylphenyl carbamic acid(diheptylphenyl)ester, N-dimethylphenyl carbamic acid(dioctylphenyl)ester, N-dimethylphenyl carbamic acid(dinonylphenyl)ester, N-dimethylphenyl carbamic acid(didecylphenyl)ester, N-dimethylphenyl carbamic acid(didodecylphenyl)ester, and N-dimethylphenyl carbamic acid(dioctadecylphenyl)ester.

<Transesterification>

The carbonyl compound produced by the method of the present embodiment can be preferably used in a production of an isocyanate by a pyrolysis of a carbonyl compound.

The carbonyl compound preferably used in the production of an isocyanate is an N-substituted carbamic acid-O-aryl ester. This is because, as compared with an N-substituted carbamic acid-O-alkyl ester, the N-substituted carbamic acid-O-aryl ester easily induces a pyrolytic reaction and tends to be easily decomposed into the corresponding isocyanate and aromatic hydroxy compound.

The carbonyl compound obtained by the above described production method may be converted to either an N-substituted carbamic acid-O-aryl ester or an N-substituted carbamic acid-O-alkyl ester, depending on the type of a hydroxy compound used. For the aforementioned reason, the carbonyl compound is preferably converted to the N-substituted carbamic acid-O-aryl ester.

When an N-substituted carbamic acid-O-alkyl ester is obtained by the above described production method, it is preferably converted to an easily thermally-decomposed N-substituted carbamic acid-O-aryl ester by a transesterification step described below. After completion of the transesterification step, the N-substituted carbamic acid-O-aryl ester can be preferably used in the reaction of an isocyanate. In the transesterification step, alcohol derived from the N-substituted carbamic acid-O-alkyl ester is generated. The transesterification will be described below.

Herein, the targeted N-substituted carbamic acid-O-alkyl ester is the N-substituted carbamic acid-O-alkyl ester represented by the above formula (7).

The aromatic hydroxy compound to be reacted may be any one of the aromatic hydroxy compounds represented by the above formula (33). In addition, the aromatic hydroxy compounds may be used singly or in combination of multiple types.

It is preferable that the production method of the present embodiment further comprise a step of reacting the N-substituted carbamic acid-O-alkyl ester represented by the above formula (7) with an aromatic hydroxy compound to obtain the N-substituted carbamic acid-O-aryl ester represented by the above formula (6) and alcohol. The hydroxy compound used in the method for producing the carbonyl compound of the present embodiment is preferably the alcohol obtained by the present step.

Referring to known methods (see, for example, WO2008/059953), the transesterification step can be carried out by applying various methods, depending on the types of compounds to be used and the like.

Reaction conditions for the transesterification are different depending on the types of compounds to be reacted. An aromatic hydroxy compound is preferably used at a stoichiometric ratio of 2:1 to 1000:1 based on the amount of ester groups constituting the N-substituted carbamic acid-O-alkyl ester used as a raw material. In order to complete the reaction at an early stage, the aromatic hydroxy compound is preferably used in an excessive amount based on such ester groups constituting the N-substituted carbamic acid-O-alkyl ester used as a raw material. If taking into consideration the size of a reaction vessel, the aromatic hydroxy compound is used at a stoichiometric ratio of more preferably from 3:1 to 100:1, and further preferably from 5:1 to 50:1, based on the ester groups constituting the N-substituted carbamic acid-O-alkyl ester used as a raw material.

The reaction temperature is generally in a range of 100° C. to 300° C. In order to increase the reaction rate, the reaction temperature is preferably high. On the other hand, there is a case in which side reactions easily occur at a high temperature. Thus, the reaction temperature is preferably in a range of 150° C. to 250° C. In order to keep the reaction temperature constant, the above described reaction vessel may be equipped with a known cooling device and/or heating device.

The reaction pressure is different depending on the types of compounds to be used or the reaction temperature. The reaction pressure may be any one of a reduced pressure, an ordinary pressure, and a compressed pressure. In general, the reaction pressure is in a range of 20 to $1 \times 10^6$ Pa.

The reaction time (which is a retention time when a continuous reaction method is applied) is not particularly limited. It is generally 0.001 to 100 hours, preferably 0.01 to 50 hours, and more preferably 0.1 to 30 hours.

In addition, it is also possible that the reaction solution is collected, and that it is then confirmed by liquid chromatography or the like that a desired amount of N-substituted carbamic acid-O-aryl ester of interest has been generated, so that the reaction can be terminated.

In the transesterification step, a catalyst is not always necessary. However, in order to decrease the reaction temperature or to complete the reaction at an early stage, such a catalyst can be used without problems. The catalyst is used at a weight percentage of 0.01% to 30%, and more preferably 0.5% to 20%, based on the weight of the N-substituted carbamic acid-O-alkyl ester.

Examples of such a catalyst include Lewis acids, transition metal compounds for generating such Lewis acids, organic tin compounds, and compounds of copper element metal, zinc and iron element metal. Specific examples include:

Lewis acids represented by $AlX_3$, $TiX_3$, $TiX_4$, $VOX_3$, $VX_5$, $ZnX_2$, $FeX_3$, and $SnX_4$ (wherein X represents a halogen, an acetoxy group, an alkoxy group, or an aryloxy group), and transition metal compounds for generating such Lewis acids;

organic tin compounds represented by $(CH_3)_3SnOCOCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$, $BuSnO(OH)$ and the like;

compounds of copper element metals such as CuCl, $CuCl_2$, CuBr, $CuBr_2$, CuI, $CuI_2$, $Cu(OAc)_2$, $Cu(acac)_2$, copper olefinate, $Bu_2Cu$, $(CH_3O)_2Cu$, $AgNO_3$, AgBr, silver picrate, and $AgC_6H_6ClO_4$;

zinc compounds such as $Zn(acac)_2$; and compounds of iron element metals such as $Fe(C_{10}H_8)(CO)_5$, $Fe(CO)_5$, $Fe(C_4H_6)(CO)_3$, $Co\ (mesitylene)_2(PEt_2Ph_2)$, $CoC_5F_5(CO)_7$, and ferrocene (wherein Bu represents a butyl group, Ph represents a phenyl group, and acac represents an acetylacetone ligand). In addition, amines such as 1,4-diazabicyclo[2,2,2]octane, triethylenediamine, and triethylamine are suitably used. Among others, organic metal catalysts such as dibutyltin dilaurate, lead octoate, and stannane octoate are preferably used as catalysts. These compounds may be used singly or in the form of a mixture of two or more types.

In the present reaction, a reaction solvent is not necessarily used. However, for the purpose of facilitating reaction operations and the like, a suitable inactive solvent may be used. Specific examples of such a reaction solvent are the same as those described in the section <Compound having ureido group>.

In general, the above described transesterification is a static reaction. Accordingly, in order to efficiently carry out the transesterification, the reaction is preferably carried out, while removing the generated alcohol (which is alcohol derived from the N-substituted carbamic acid-O-alkyl ester as a raw material) from the reaction system.

Accordingly, if an aromatic hydroxy compound is selected such that the standard boiling point of the aromatic hydroxy compound used in the transesterification becomes higher than the standard boiling point of the alcohol derived from the N-substituted carbamic acid-O-alkyl ester as a raw material, it results in that the compound having the lowest standard boiling point in the reaction system can be the alcohol derived from the N-substituted carbamic acid-O-alkyl ester as a raw material, and as a result, it becomes easy to remove the product from the reaction system.

Moreover, in order to efficiently carry out the transesterification, it is preferably carried out according to a continuous method. That is to say, it is preferable that the N-substituted carbamic acid-O-alkyl ester as a raw material and the aromatic hydroxy compound be continuously supplied into a reaction vessel to carry out the transesterification, that the generated alcohol derived from the N-substituted carbamic acid-O-alkyl ester as a raw material be removed in the form of a gaseous ingredient from the reaction vessel, and that a reaction solution containing the generated N-substituted carbamic acid-O-aryl ester and the aromatic hydroxy compound be continuously removed from the bottom portion of the reaction vessel.

Materials for the reaction vessel and line, in which the transesterification step is carried out, are not particularly limited, as long as they do not affect the starting materials or the reaction substances. Thus, any types of known materials may be used. For example, the same material as that for the above described reaction vessel for producing the N-substituted carbamic acid ester can be used.

A form of the reaction vessel is not particularly limited. Known tank-type and column-type reaction vessels can be used. Various types of known methods, such as a method of using a reaction vessel comprising any one of an agitation tank, a multi-stage agitation tank, a distillation column, a multi-stage distillation column, a multitubular reaction vessel, a continuous multi-stage distillation column, a packed column, a thin-film evaporator, a reaction vessel comprising a support therein, a forced-circulation reaction vessel, a falling-film evaporator, a falling-drop evaporator, a trickle phase reaction vessel and a bubble column, or a method of combining these devices, are used. From the viewpoint of efficient deviation of equilibrium to the generation system side, a method of using a thin-film evaporator or a column-type reaction vessel is preferable. In addition, a structure having a large gas-liquid contact area, which is able to promptly transfer to the gaseous phase, the generated alcohol derived from the N-substituted carbamic acid-O-alkyl ester as a raw material, is preferable.

The multi-stage distillation column is a distillation column having a multi-stage, in which the number of theoretical plates in distillation is two or more. A type of such a multi-stage distillation column is not particularly limited, as long as it enables continuous distillation. Any type of multi-stage distillation column can be used, as long as it is generally used as a multi-stage distillation column. Examples of the multi-stage distillation column include: plate-column type distillation columns, which use a tray such as a bubble cap tray, a perforated plate tray, a valve tray, or a countercurrent tray; and packed column-type distillation columns, which are filled with various types of fillers such as a Raschig ring, a Lessing ring, a pall ring, a Berl saddle, an intalox saddle, a Dixon packing, a McMahon packing, Heli-Pack, a Sulzer packing, or Melapack. The type of a packed column that can be used herein is not particularly limited, as long as it is a packed column filled with the above described known filler. Moreover, a plate column-packed column, mixed column-type distillation column comprising both a plate column portion and a portion filled with a filler is also preferably used.

A line for supplying inert gas and/or a liquid-state inactive solvent from the lower portion of the reaction vessel may be equipped in the reaction vessel, separately. Otherwise, when the mixed solution containing the N-substituted carbamic acid-O-aryl ester of interest and the aromatic hydroxy compound contains the N-substituted carbamic acid-O-alkyl ester as a raw material, a line for re-circulating a part of or an entire mixed solution in the reaction vessel may also be equipped. When the above described inactive solvent is used, it may be a gaseous and/or liquid solvent.

Gaseous ingredients containing the alcohol derived from the N-substituted carbamic acid-O-alkyl ester as a raw material, which has been discharged from the reaction vessel, are preferably purified by a known method such as a distillation column, and the resultant can be recycled as raw material alcohol for producing an N-substituted carbamic acid-O-alkyl ester.

<Step of Producing Isocyanate by Pyrolytic Reaction of Carbonyl Compound>

The method for producing the isocyanate of the present embodiment comprises a step of subjecting the carbonyl compound obtained by the above described production method to a pyrolytic reaction to produce the isocyanate.

The carbonyl compound that is preferably used in the method for producing the isocyanate of the present embodiment is an N-substituted carbamic acid-O-aryl ester. This is because, as compared with an N-substituted carbamic acid-O-alkyl ester, the N-substituted carbamic acid-O-aryl ester easily induces a pyrolytic reaction and tends to be easily decomposed into the corresponding isocyanate and an aromatic hydroxy compound. Accordingly, the method for producing the isocyanate of the present embodiment preferably comprises a step of subjecting the N-substituted carbamic acid-O-aryl ester obtained by the above described production method to a pyrolytic reaction to obtain a product containing an isocyanate and an aromatic hydroxy compound. In addition, in the method for producing the carbonyl compound of the present embodiment, the used hydroxy compound or aromatic hydroxy compound is preferably the aromatic hydroxy compound obtained in the aforementioned step.

Hereinafter, a step of subjecting an N-substituted carbamic acid-O-aryl ester to a pyrolytic reaction to produce an isocyanate (which is often referred to as a "pyrolytic step" in the present specification) will be described.

The reaction temperature is generally in a range of 100° C. to 300° C. In order to increase the reaction rate, the reaction temperature is preferably high. On the other hand, there is a case in which the above described side reactions are easily caused by an N-substituted carbamic acid ester and/or an isocyanate as a product at a high temperature. Thus, the reaction temperature is preferably in a range of 150° C. to 250° C. In order to keep the reaction temperature constant, the above described reaction vessel may be equipped with a known cooling device and/or heating device.

The reaction pressure is different depending on the types of compounds to be used or the reaction temperature. The reaction pressure may be any one of a reduced pressure, an ordinary pressure, and a compressed pressure. In general, the reaction pressure is in a range of 20 to $1 \times 10^6$ Pa.

The reaction time (which is a retention time when a continuous reaction method is applied) is not particularly limited. It is generally 0.001 to 100 hours, preferably 0.005 to 50 hours, and more preferably 0.01 to 10 hours.

In the method for producing an isocyanate of the present embodiment, a catalyst is not always necessary. However, in order to decrease the reaction temperature or to complete the reaction at an early stage, such a catalyst can be used without problems. The catalyst is used at a weight percentage of 0.01% to 30%, and more preferably 0.5% to 20%, based on the weight of the N-substituted carbamic acid ester.

The same catalysts as those used in the above described transesterification step can be used herein.

Moreover, as described above, when a catalyst is used in any step in the production of the N-substituted carbamic acid ester, there is a case in which the residue of the catalyst or the like is supplied to the pyrolytic step. The presence of such a catalyst residue or the like causes no problems in many cases.

In the pyrolytic step, a reaction solvent other than a hydroxy compound is not necessarily used. However, for the purpose of facilitating reaction operations and the like, a suitable inactive solvent may be used. Specific examples of such a reaction solvent are the same as those described in the section <Compound having ureido group>.

Among the obtained carbonyl compounds, when the N-substituted carbamic acid ester is retained at a high temperature for a long period of time, it may induce side reactions, such as a reaction of generating a compound containing a urea bond according to a reaction of removing a carbonic acid ester from two molecules of N-substituted carbamic acid ester, or a reaction of generating an allophanate group as a result of a reaction with an isocyanate group that has been generated by the pyrolysis of the N-substituted carbamic acid ester, in some cases. Accordingly, the time at which the N-substituted carbamic acid ester and the isocyanate are retained at a high temperature is preferably as short as possible.

Therefore, the pyrolytic reaction is preferably carried out by a continuous method. The continuous method is a method which comprises continuously supplying a mixture containing the N-substituted carbamic acid ester to a reaction vessel to subject it to a pyrolytic reaction, and then continuously discharging the generated isocyanate and hydroxy compound from the pyrolytic reaction vessel.

In the continuous method, a low-boiling ingredient generated as a result of the pyrolytic reaction is preferably recovered as a gaseous phase ingredient from the upper portion of the pyrolytic reaction vessel, and the residue is recovered as a liquid phase ingredient from the bottom portion of the pyrolytic reaction vessel. All of compounds existing in the pyrolytic reaction vessel may be recovered as gaseous phase ingredients. However, the presence of a liquid phase ingredient in the pyrolytic reaction vessel provides an effect of dissolving a polymeric compound generated as a side reaction that is induced by the N-substituted carbamic acid ester and/or isocyanate and thereby preventing the polymeric compound from adhering to and/or accumulating in the pyrolytic reaction vessel.

An isocyanate and a hydroxy compound are generated as a result of the pyrolytic reaction of the N-substituted carbamic acid ester. At least one of these compounds is recovered as a gaseous phase ingredient. Which compound is recovered as a gaseous phase ingredient depends on pyrolytic reaction conditions and the like.

Herein, the expression "low-boiling ingredient generated as a result of the pyrolytic reaction of the N-substituted carbamic acid ester" is used in the present embodiment to mean a hydroxy compound and/or an isocyanate generated as a result of the pyrolytic reaction of the N-substituted carbamic acid ester, and particularly means a compound that can be present in the form of gas under conditions in which the present pyrolytic reaction is carried out.

For example, a method comprising recovering an isocyanate and a hydroxy compound generated as a result of the pyrolytic reaction in the form of gaseous phase ingredients, and also recovering a liquid phase ingredient containing an N-substituted carbamic acid ester, can be adopted. In the present method, the isocyanate and the hydroxy compound may be recovered from the pyrolytic reaction vessel, separately.

The recovered gaseous phase ingredient containing an isocyanate is supplied, preferably in the form of a gaseous phase, to a distillation apparatus for purifying and separating the isocyanate. It is also possible to convert the recovered gaseous phase ingredient containing an isocyanate to a liquid phase using a condenser or the like, and to supply it to a distillation apparatus. However, the apparatus becomes complicated, or enormous energy is required in many cases. Thus, it is not favorable.

When the liquid phase ingredient contains an N-substituted carbamic acid ester, a part of or an entire liquid phase ingredient is preferably supplied to the upper portion of the pyrolytic reaction vessel, and the N-substituted carbamic acid ester is again subjected to a pyrolytic reaction.

Herein, when the pyrolytic reaction vessel is a distillation column for example, the term "the upper portion of the pyrolytic reaction vessel" is used to mean a plate that is two or more theoretical plates higher than the bottom of the column.

When the pyrolytic reaction vessel is a thin-film distillation apparatus, it means a portion higher than the portion to be heated.

The method for producing the isocyanate of the present embodiment further comprises a step of separating a product obtained by the pyrolytic reaction into a gaseous phase ingredient and a liquid phase ingredient and then recovering a part of or an entire liquid phase ingredient. The liquid phase ingredient preferably contains a compound having a urea bond. Moreover, in the method for producing the carbonyl compound of the present embodiment, the compound having the urea bond used is preferably a compound having a urea bond contained in the liquid phase ingredient obtained in the above step.

When a part of or an entire liquid phase ingredient is supplied to the upper portion of the pyrolytic reaction vessel, the liquid phase ingredient is transferred thereto, while retaining it preferably at 50° C. to 180° C., more preferably 70° C. to 170° C., and further preferably 100° C. to 150° C.

Also, a method which comprises recovering an isocyanate and a hydroxy compound generated as a result of the pyrolytic reaction in the form of gaseous phase ingredients, and then recovering a liquid phase ingredient containing an N-substituted carbamic acid ester from the bottom portion of the pyrolytic reaction vessel can be adopted. In the present method as well, the recovered gaseous ingredient containing an isocyanate is supplied, preferably in the form of a gaseous phase, to a distillation apparatus for purifying and separating the isocyanate.

On the other hand, a part of or an entire liquid phase ingredient containing an N-substituted carbamic acid ester is supplied to the upper portion of the pyrolytic reaction vessel, and the N-substituted carbamic acid ester is again subjected to a pyrolytic reaction. When a part of or an entire liquid phase ingredient is supplied to the upper portion of the pyrolytic reaction vessel, the liquid phase ingredient is transferred thereto, while retaining it preferably at 50° C. to 180° C., more preferably 70° C. to 170° C., and further preferably 100° C. to 150° C.

Moreover, a method comprising recovering, for example, an aromatic hydroxy compound, from among an isocyanate and a hydroxy compound generated as a result of the pyrolytic reaction, in the form of a gaseous phase ingredient, and then recovering a mixture containing the isocyanate as a liquid phase ingredient from the bottom portion of the pyrolytic reaction vessel can be adopted.

In this case, the liquid phase ingredient is supplied to a distillation apparatus, and an isocyanate is then recovered. When the liquid phase ingredient contains an N-substituted carbamic acid ester, a part of or an entire mixture containing the N-substituted carbamic acid ester is preferably supplied to the upper portion of the pyrolytic reaction vessel, and the N-substituted carbamic acid ester is again subjected to a pyrolytic reaction.

When a part of or an entire liquid phase ingredient is supplied to the upper portion of the pyrolytic reaction vessel, the liquid phase ingredient is transferred thereto, while retaining it preferably at 50° C. to 180° C., more preferably 70° C. to 170° C., and further preferably 100° C. to 150° C.

As stated above, in the pyrolytic reaction, the liquid phase ingredient is preferably recovered from the bottom portion of the pyrolytic reaction vessel. This is because the above described polymeric by-products generated as a result of side reactions induced by the N-substituted carbamic acid ester and/or the isocyanate can be dissolved, and they can be discharged in the form of liquid phase ingredients from the pyrolytic reaction vessel, and thus because it has an effect of reducing the amount of the polymeric compound adhering to and/or accumulating in the pyrolytic reaction vessel.

When the liquid phase ingredient contains the N-substituted carbamic acid ester, a part of or an entire liquid phase ingredient is supplied to the upper portion of the pyrolytic reaction vessel, the N-substituted carbamic acid ester is subjected to a pyrolytic reaction again. However, if this step is repeatedly carried out, there is a case in which polymeric by-products are accumulated in the liquid phase ingredient. In such a case, a part of or an entire liquid phase ingredient is removed from the reaction system, so that the amounts of the accumulated polymeric by-products can be reduced, or they can be maintained in a certain concentration.

The liquid phase ingredient removed from the reaction system contains a hydroxy compound in many cases. Such a hydroxy compound may be recovered from the liquid phase ingredient according to a method such as distillation. The hydroxy compound can be recycled as a raw material used in the method for producing an N-substituted carbamic acid ester of the present embodiment or as a hydroxy compound used in the above described transesterification.

In addition, the liquid phase ingredient recovered from the bottom portion of the pyrolytic reaction vessel contains a compound having a urea bond in many cases. A step of recycling the compound having the urea bond as a raw material used in the method for producing the carbonyl compound of the present embodiment, and reacting the compound having the urea bond with a carbonic acid derivative under heating at a temperature equal to or higher than the thermal dissociation temperature of the urea bond, may further be added.

There is a case in which the recovered isocyanate contains an aromatic hydroxy compound and the like, depending on reaction conditions, conditions for recovering the isocyanate, the reaction apparatus, etc. In such a case, operations such as distillation may be further carried out, and an isocyanate with a desired purity may be obtained.

A type of the pyrolytic reaction vessel is not particularly limited. In order to efficiently recover the gaseous phase ingredient, a known distillation apparatus is preferably used. For example, various types of known methods such as a method of using a reaction vessel comprising any one of a distillation column, a multi-stage distillation column, a multitubular reaction vessel, a continuous multi-stage distillation column, a packed column, a thin-film evaporator, a reaction vessel comprising a support therein, a forced-circulation reaction vessel, a falling-film evaporator and a falling-drop evaporator, and a method of combining these devices, are used.

From the viewpoint of the prompt removal of a low-boiling ingredient from the reaction system, it is preferably a method of using a tubular reaction vessel, and more preferably, a method of using a reaction vessel such as a tubular thin-film evaporator or a tubular falling-film evaporator. A structure having a large gas-liquid contact area for promptly transferring the generated low-boiling ingredient to the gaseous phase is preferable.

Materials for the pyrolytic reaction vessel and the line are not particularly limited, as long as they do not affect the urethane or the aromatic hydroxy compound as a product, an isocyanate, and the like. Thus, known materials may be used. For example, the same material as that for the above described reaction vessel for producing the N-substituted carbamic acid ester can be used.

<Washing of Reaction Vessel>

In the production of an N-substituted carbamic acid-O-aryl ester of the present embodiment and the production of an isocyanate using the N-substituted carbamic acid-O-aryl ester, there may be a case in which a small amount of polymeric by-product and the like are generated.

Since this polymeric by-product is highly soluble in the aromatic hydroxy compound used in the present embodiment, it is removed in the form of an aromatic hydroxy compound solution from the reaction vessel. However, when conditions for operating the reaction vessel are changed or when such operation is carried out for a long period of time, there is a case in which such a polymeric by-product adheres to the reaction vessel.

In such a case, the inside (particularly, the wall surface) of the concerned reaction vessel is washed with an acid that is a good solvent for the polymeric by-product, so that the inside of the reaction vessel can be maintained clean.

A type of the acid used in the washing is not particularly limited, as long as it dissolves the polymeric by-product. Either an organic acid or an inorganic acid may be used. Preferably, an organic acid is used.

Examples of such an organic acid include carboxylic acid, sulfonic acid, sulfinic acid, phenols, enols, thiophenols, imides, oximes, and aromatic sulfonamides. Preferably, carboxylic acid and phenols are used.

Examples of such a compound include: saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid, octanoic acid, nonanoic acid, decanoic acid, undecanoic acid, dodecanoic acid, tetradecanoic acid, hexadecanoic acid, acrylic acid, crotonoic acid, isocrotonoic acid, vinyl acetate, methacrylic acid, angelic acid, tiglic acid, allyl acetate, or undecenoic acid; saturated or unsaturated aliphatic dicarboxylic acids such as oxalic acid, malonic acid, succinic acid, glutaric acid, adipic acid, heptanedioic acid, octanedioic acid, nonanedioic acid, decanedioic acid, maleic acid, fumaric acid, methyl maleate, methyl fumarate, pentenedioic acid, itaconic acid, or allyl malonate; saturated or unsaturated aliphatic tricarboxylic acid compounds such as 1,2,3-propanetricarboxylic acid, 1,2,3-propenetricarboxylic acid, or 2,3-dimethylbutane-1,2,3-tricarboxylic acid; aromatic carboxylic acid compounds such as benzoic acid, methyl benzoate, ethyl benzoate, propyl benzoate, dimethyl benzoate, or trimethyl benzoate; aromatic dicarboxylic acid compounds such as phthalic acid, isophthalic acid, terephthalic acid, or methyl isophthalate; aromatic tricarboxylic acid compounds such as hemimellitic acid, trimellitic acid, or trimesic acid; mono-substituted phenols such as phenol, methyl phenol, ethyl phenol, propyl phenol, butyl phenol, pentyl phenol, hexyl phenol, heptyl phenol, octyl phenol, nonyl phenol, decyl phenol, dodecyl phenol, phenyl phenol, phenoxy phenol, or cumyl phenol; and dimethyl phenol, diethyl phenol, dipropyl phenol, dibutyl phenol, dipentyl phenol, dihexyl phenol, diheptyl phenol, dioctyl phenol, dinonyl phenol, didecyl phenol, didodecyl phenol, diphenyl phenol, diphenoxy phenol, and dicumyl-phenol.

Taking into consideration the influence caused by the washing solvent, which remains after completion of the operation of washing the pyrolytic reaction vessel, among these organic acids, it is more preferably an aromatic hydroxy compound, and further preferably a compound of the same type as the aromatic hydroxy compound that can be generated as a result of the above described method for producing an N-substituted carbamic acid-O-aryl ester and/or the pyrolytic reaction of the N-substituted carbamic acid-O-aryl ester is used.

When such an aromatic hydroxy compound is used as the acid for the washing, from the viewpoint of washing effect, the standard boiling point of the aromatic hydroxy compound preferably has a difference in boiling point of 10° C. or higher from the standard boiling point of the above described isocyanate generated as a result of the pyrolytic reaction of the N-substituted carbamic acid-O-aryl ester.

As a method of washing the reaction vessel using the above described washing solvent, various methods such as a method of introducing a washing solvent from the upper portion of the reaction vessel into the reaction vessel to wash it, or a method of introducing a washing solvent into the bottom portion of the reaction vessel and then boiling the washing solvent in the reaction vessel to wash the inside thereof, can be applied.

The washing operation is not necessarily carried out every time after completion of the reaction. The number of the washing operations can be arbitrarily determined depending on the compounds used, the operating rate, and the like. The washing operation can be carried out at a frequency of, preferably once in the operation time for 1 to 20000 hours, more preferably once in the operation time for 1 day to 1 year, and further preferably once in the operation time for 1 month to 1 year. The reaction vessel may be equipped with a line for introducing such a washing solvent into the reaction vessel.

A carbonyl compound is industrially useful. In particular, when such a carbonyl compound is an N-substituted carbamic acid ester, an isocyanate can be produced by the pyrolytic reaction of the N-substituted carbamic acid ester. Accordingly, the method for producing the carbonyl compound of the present embodiment is effective, and it is industrially, extremely important.

EXAMPLES

Hereinafter, the present invention will be specifically described based on the following examples. However, these examples are not intended to limit the scope of the present invention.
<Analysis Method>
(1) NMR Analysis Method
Apparatus: JNM-A400 FT-NMR System, Manufactured by JEOL Ltd., Japan
Preparation of $^1$H and $^{13}$C-NMR Analysis Samples Approximately 0.3 g of sample solution was weighed, and thereafter, approximately 0.7 g of deuterated chloroform (manufactured by Aldrich, U.S.A.; 99.8%) and 0.05 g of tetramethyltin (manufactured by Wako Pure Chemical Industries, Ltd., Japan; Wako Ikkyu) used as an internal standard substance were added to the solution, followed by homogeneously mixing them. The thus mixed solution was used as an NMR analysis sample.
Quantitative Analysis Method Each standard substance was analyzed, and based on the prepared calibration curve, the analysis sample solution was subjected to quantitative analysis.
(2) Liquid Chromatography Analysis Method
Apparatus: LC-10AT System, manufactured by Shimadzu Corporation, Japan
Column: Inertsil-ODS Column, manufactured by GL Sciences Inc., Japan (two Inertsil-ODS Columns were connected in series)
Eluent: A mixed solution of 5 mmol/L ammonium acetate aqueous solution (solution A) and acetonitrile (solution B)
Eluent flow rate: 2 mL/min
Column temperature: 35° C.
Detector: R. I. Detector (refractometer), and PDA Detector (photodiode array detector; measured wavelength range: 200 nm to 300 nm)
Liquid Chromatography Analysis Samples Approximately 0.1 g of sample was weighed, and thereafter, approximately 1 g of tetrahydrofuran (manufactured by Wako Pure Chemical Industries, Ltd., Japan; dehydrated) and approximately 0.02 g of 1,1-diethyl urea (manufactured by Tokyo Chemical Industry Co., Ltd., Japan) used as an internal standard substance were added to the sample, followed by homogeneously mixing them. The thus mixed solution was used as a sample in liquid chromatography analysis.
Quantitative Analysis Method Each standard substance was analyzed, and based on the prepared calibration curve, the analysis sample solution was subjected to quantitative analysis.
(3) Method of Measuring Thermal Dissociation Temperature
Apparatus: TGDTA Analyzer TG8120, Manufactured by Rigaku Corporation, Japan
MS Analyzer GCMS-QP 2010Plus, Manufactured by Shimadzu Corporation, Japan
Atmosphere: helium
Temperature rise rate: 10° C./min
Measured temperature range: room temperature (approximately 25° C.) to 400° C.
Analytic Method The sample (approximately 5 mg) was heated under the above described measurement conditions, and the generated gas was then analyzed using an MS analyzer. The temperature, at which a compound containing a $NH_2$ group generated as a result of decomposition of a urea bond was detected, was defined as the thermal dissociation temperature of the concerned compound.

Example 1

Step (1-1): Production of N-substituted Carbamic Acid Ester
Using the reaction vessel shown in FIG. 1, an N-substituted carbamic acid ester was produced.

6.30 kg (28.1 mol) of 1,3-dicyclohexyl urea was mixed with 13.2 kg (59.5 mol) of 2,6-xylenol to prepare a raw material solution. Thereafter, 2,6-xylenol was added into a plate-type distillation column 102 having 40 plates, and it was then boiled with a reboiler 105, so that it could be in a total reflux state. At this time, the temperature of the $15^{th}$ plate (counted from the column top side) on which a line 2 was equipped was 210° C. This temperature was higher than the thermal dissociation temperature (205° C.) of 1,3-dicyclohexyl urea. Through a line 1 equipped on the uppermost plate (the first plate) of the distillation column 102, a mixed solution having the same composition as that of the raw material solution was introduced into the column at a rate of approximately 2.0 kg/Hr. At the same time, through the line 2, a mixed solution of urea and 2,6-xylenol (urea concentration: approximately 5 wt %) was fed to the column at a rate of approximately 6.9 kg/Hr. After operation conditions had been stabilized, the raw material solution was supplied through the line 1 at a rate of approximately 2.0 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 85° C. The thus obtained ingredient was recovered into a storage tank 104.

The reaction solution recovered in the storage tank 105 was analyzed by liquid chromatography and ¹H-NMR. As a result, it was found that the reaction solution was a solution containing an N-cyclohexyl carbamic acid(2,6-dimethylphenyl)ester, and that the yield of the N-cyclohexyl carbamic acid(2,6-dimethylphenyl)ester was approximately 95% based on 1,3-dicyclohexyl urea.

Example 2

Step (2-1): Production of N-substituted Carbamic Acid Ester

Using the reaction vessel shown in FIG. 1, an N-substituted carbamic acid ester was produced.

8.20 kg (37.4 mol) of 1,3-diphenyl urea was mixed with 12.0 kg (162 mol) of n-butanol to prepare a raw material solution. Thereafter, n-butanol was added into a plate-type distillation column 102 having 40 plates, and it was then boiled with a reboiler 105, so that it could be in a total reflux state. At this time, the pressure of the column top was 12 atmospheric pressures, and the temperature of the 15$^{th}$ plate (counted from the top side) on which a line 2 was equipped was 220° C. This temperature was higher than the thermal dissociation temperature (210° C.) of 1,3-dicyclohexyl urea. Through a line 1 equipped on the uppermost plate (the first plate) of the distillation column 102, a mixed solution having the same composition as that of the raw material solution was introduced into the column at a rate of approximately 2.0 kg/Hr. At the same time, through the line 2, a mixed solution of urea and n-butanol (urea concentration: approximately 5 wt %) was fed to the column at a rate of approximately 9.3 kg/Hr. After operation conditions had been stabilized, the raw material solution was supplied through the line 1 at a rate of approximately 2.0 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 50° C. The thus obtained ingredient was recovered into a storage tank 104.

The reaction solution recovered in the storage tank 105 was analyzed by liquid chromatography and ¹H-NMR. As a result, it was found that the reaction solution was a solution containing an N-phenyl carbamic acid(n-butyl)ester, and that the yield of the N-cyclohexyl carbamic acid(2,6-dimethylphenyl)ester was approximately 93% based on 1,3-dicyclohexyl urea.

Example 3

Step (3-1): Production of N-substituted Carbamic Acid Ester

Using the reaction vessel shown in FIG. 1, an N-substituted carbamic acid ester was produced.

7.2 kg (12.8 mol) of 1,3-dioctadecyl urea was mixed with 12.2 kg (130 mol) of phenol to prepare a raw material solution. Thereafter, phenol was added into a plate-type distillation column 102 having 40 plates, and it was then boiled with a reboiler 105, so that it could be in a total reflux state. At this time, the pressure of the column top was 2.3 atmospheric pressures, and the temperature of the 15$^{th}$ plate (counted from the top side) on which a line 2 was equipped was 220° C. This temperature was higher than the thermal dissociation temperature (210° C.) of 1,3-dioctadecyl urea. Through a line 1 equipped on the uppermost plate (the first plate) of the distillation column 102, a mixed solution having the same composition as that of the raw material solution was introduced into the column at a rate of approximately 2.0 kg/Hr. At the same time, through the line 2, a mixed solution of phenyl carbamate and phenol (phenyl carbamate concentration: approximately 7 wt %) was fed to the column at a rate of approximately 4.8 kg/Hr. After operation conditions had been stabilized, the raw material solution was supplied through the line 1 at a rate of approximately 2.0 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 50° C. The thus obtained ingredient was recovered into a storage tank 104.

The reaction solution recovered in the storage tank 105 was analyzed by liquid chromatography and ¹H-NMR. As a result, it was found that the reaction solution was a solution containing an N-octadecyl carbamic acid phenyl ester, and that the yield of the N-octadecyl carbamic acid phenyl ester was approximately 94% based on 1,3-dioctadecyl urea.

Reference Example 1

Step (A-1): Production of N-substituted Carbamic Acid Ester

Using the reaction vessel shown in FIG. 1, an N-substituted carbamic acid ester was produced.

1.2 kg (10.3 mol) of 1,6-hexamethylenediamine, 3.1 kg (17.8 mol) of di(n-butyl)carbonate, and 10.3 kg of n-butanol were mixed to prepare a raw material solution. Thereafter, n-butanol was added into a plate-type distillation column 102 having 40 plates, and it was then boiled with a reboiler 105, so that it could be in a total reflux state. At this time, the pressure of the column top was 11 atmospheric pressures, and the temperature of the 15$^{th}$ plate (counted from the top side) on which a line 2 was equipped was 220° C. Through a line 1 equipped on the uppermost plate (the first plate) of the distillation column 102, a mixed solution having the same composition as that of the raw material solution was introduced into the column at a rate of approximately 2.5 kg/Hr. After operation conditions had been stabilized, the raw material solution was supplied through the line 1 at a rate of approximately 2.5 kg/Hr, and the reaction solution was then recovered into a storage tank 105 through a line 6 equipped at the lowermost portion of the distillation column 102.

The reaction solution recovered in the storage tank 105 was analyzed by liquid chromatography and ¹H-NMR. As a result, it was found that the reaction solution was a solution containing an N,N'-hexanediyl-di(carbamic acid(n-butyl)ester), and that the yield of the N,N'-hexanediyl-di(carbamic acid(n-butyl)ester) was approximately 74% based on 1,6-hexamethylenediamine. In addition, this reaction solution contained di(n-butyl)-6,6'-carbonylbis(azanediyl)bis(hexane-6,1-diyl) dicarbamate as a compound having a urea bond, and the yield of the dibutyl-6,6'-carbonylbis(azanediyl)bis(hexane-6,1-diyl) dicarbamate was approximately 21% based on 1,6-hexamethylenediamine. The thermal dissociation temperature of the urea bond contained in the di(n-butyl)-6,6'-carbonylbis(azanediyl)bis(hexane-6,1-diyl) dicarbamate was 205° C.

Moreover, the reaction solution was collected from a sampling port equipped on the 15$^{th}$ plate of the distillation column during the steady operation, and it was then analyzed. As a result, di(n-butyl)carbonate was not detected.

Example 4

Step (4-1): Production of N-substituted Carbamic Acid Ester

The same method as that in the step (A-1) of Reference example 1 was carried out, with the exception that a mixed solution of di(n-butyl)carbonate and n-butanol (di(n-butyl) carbonate concentration: approximately 50 wt %) was fed through the line 2 at a rate of approximately 1.3 kg/Hr.

The reaction solution recovered in the storage tank 105 was analyzed by liquid chromatography and $^1$H-NMR. As a result, it was found that the reaction solution was a solution containing an N,N'-hexanediyl-di(carbamic acid(n-butyl)ester), and that the yield of the N,N'-hexanediyl-di(carbamic acid(n-butyl)ester) was approximately 92% based on 1,6-hexamethylenediamine. In addition, this reaction solution contained di(n-butyl)-6,6'-carbonylbis(azanediyl)bis(hexane-6,1-diyl) dicarbamate as a compound having a urea bond, and the yield of the din-butyl)-6,6'-carbonylbis(azanediyl)bis(hexane-6,1-diyl) dicarbamate was approximately 2% based on 1,6-hexamethylenediamine. The thermal dissociation temperature of the urea bond contained in the di(n-butyl)-6,6'-carbonylbis(azanediyl)bis(hexane-6,1-diyl) dicarbamate was 205° C. When compared with Reference Example 1, on the 15$^{th}$ plate for supplying the mixed solution of di(n-butyl)carbonate and n-butanol, the compound having the urea bond reacted with the di(n-butyl)carbonate under heating at a temperature equal to or higher than the thermal dissociation temperature of the urea bond (220° C.) to generate an N-substituted carbamic acid ester. Thus, it was considered that the N-substituted carbamic acid ester could be obtained at a high yield.

Reference Example 2

Step (B-1): Production of N-substituted Carbamic Acid Ester

Using the reaction vessel shown in FIG. 1, an N-substituted carbamic acid ester was produced.

3.2 kg (18.8 mol) of 3-aminomethyl-3,5,5-trimethylcyclohexylamine, 6.6 kg (30.8 mol) of diphenyl carbonate, and 8.2 kg (87.2 mol) of phenol were mixed to prepare a raw material solution. Thereafter, phenol was added into a plate-type distillation column 102 having 40 plates, and it was then boiled with a reboiler 105, so that it could be in a total reflux state. At this time, the pressure of the column top was 2.6 atmospheric pressures, and the temperature of the 15$^{th}$ plate (counted from the top side) on which a line 2 was equipped was 230° C. Through a line 1 equipped on the uppermost plate (the first plate) of the distillation column 102, a mixed solution having the same composition as that of the raw material solution was introduced into the column at a rate of approximately 2.8 kg/Hr. After operation conditions had been stabilized, the raw material solution was supplied through the line 1 at a rate of approximately 2.8 kg/Hr, and the reaction solution was then recovered into a storage tank 105 through a line 6 equipped at the lowermost portion of the distillation column 102.

The reaction solution recovered in the storage tank 105 was analyzed by liquid chromatography and $^1$H-NMR. As a result, it was found that the reaction solution was a solution containing a 3-(phenoxycarbonylaminomethyl)-3,5,5-trimethylcyclohexyl carbamic acid ester, and that the yield of the 3-(phenoxycarbonylaminomethyl)-3,5,5-trimethylcyclohexyl carbamic acid ester was approximately 61% based on 3-aminomethyl-3,5,5-trimethylcyclohexylamine. In addition, this reaction solution contained approximately 30% by mass of diphenyl-5,5'-(carbonylbis(azanediyl)bis(methylene))bis(3,3,5-trimethylcyclohexane-5,1-diyl) dicarbamate as a compound having a urea bond. The thermal dissociation temperature of the urea bond contained in the diphenyl-5,5'-(carbonylbis(azanediyl)bis(methylene))bis(3,3,5-trimethylcyclohexane-5,1-diyl) dicarbamate was 206° C.

Moreover, the reaction solution was collected from a sampling port equipped on the 15$^{th}$ plate of the distillation column during the steady operation, and it was then analyzed. As a result, diphenyl carbonate was not detected.

Example 5

Step (5-1): Production of N-substituted Carbamic Acid Ester

The same method as that in the step (B-1) of Reference example 2 was carried out, with the exception that a mixed solution of diphenyl carbonate and phenol (diphenyl carbonate concentration: approximately 63 wt %) was fed through the line 2 at a rate of approximately 2.0 kg/Hr.

The reaction solution recovered in the storage tank 105 was analyzed by liquid chromatography and $^1$H-NMR. As a result, it was found that the reaction solution was a solution containing a 3-(phenoxycarbonylaminomethyl)-3,5,5-trimethylcyclohexyl carbamic acid phenyl ester, and that the yield of the 3-(phenoxycarbonylaminomethyl)-3,5,5-trimethylcyclohexyl carbamic acid phenyl ester was approximately 93% based on 3-aminomethyl-3,5,5-trimethylcyclohexylamine.

In addition, from the above described results of Reference Example 2, it was assumed that a compound having a urea bond was generated (the thermal dissociation temperature of the urea bond: 206° C.) in the production of an N-substituted carbamic acid ester in the present step. In the present example, on the 15$^{th}$ plate for supplying the mixed solution of diphenyl carbonate and phenol, the compound having the urea bond reacted with the diphenyl carbonate under heating at a temperature equal to or higher than the thermal dissociation temperature of the urea bond (230° C.) to generate an N-substituted carbamic acid ester. Thus, it was considered that the N-substituted carbamic acid ester could be obtained at a high yield.

Reference Example 3

Step (C-1): Production of N-substituted Carbamic Acid Ester

Using the reaction vessel shown in FIG. 1, an N-substituted carbamic acid ester was produced.

2.8 kg (13.3 mol) of 4,4'-methylenebis(cyclohexylamine), 5.2 kg (24.3 mol) of diphenyl carbonate, and 18.0 kg (191 mol) of phenol were mixed to prepare a raw material solution. Thereafter, phenol was added into a plate-type distillation column 102 having 40 plates, and it was then boiled with a reboiler 105, so that it could be in a total reflux state. At this time, the pressure of the column top was 2.3 atmospheric pressures, and the temperature of the 15$^{th}$ plate (counted from the top side) on which a line 2 was equipped was 220° C. Through a line 1 equipped on the uppermost plate (the first plate) of the distillation column 102, a mixed solution having the same composition as that of the raw material solution was introduced into the column at a rate of approximately 2.4 kg/Hr. After operation conditions had been stabilized, the raw material solution was supplied through the line 1 at a rate of approximately 2.4 kg/Hr, and the reaction solution was then recovered into a storage tank 105 through a line 6 equipped at the lowermost portion of the distillation column 102.

The reaction solution recovered in the storage tank 105 was analyzed by liquid chromatography and $^1$H-NMR. As a result, it was found that the reaction solution was a solution containing a 4,4'-methylenebis(cyclohexane-4,1-diyl)di(carbamic acid phenyl ester), and that the yield of the 4,4'-methylenebis(cyclohexane-4,1-diyl)di(carbamic acid phenyl ester) was approximately 77% based on 4,4'-methylenebis (cyclohexylamine). In addition, this reaction solution contained approximately 19% by mass of 4,4'-(4,4'-carbonylbis (azanediyl)bis(cyclohexane-4,1-diyl)bis(methylene))bis (cyclohexane-4,1-diyl)di(carbamic acid phenyl ester) as a compound having a urea bond. The thermal dissociation temperature of the urea bond contained in the 4,4'-(4,4'-carbonylbis(azanediyl)bis(cyclohexane-4,1-diyl)bis(methylene)) bis(cyclohexane-4,1-diyl)di(carbamic acid phenyl ester) was 210° C.

Example 6

Step (6-1): Production of N-substituted Carbamic Acid Ester

The same method as that in the step (C-1) of Reference example 3 was carried out, with the exception that a mixed solution of diphenyl carbonate and phenol (diphenyl carbonate concentration: approximately 58 wt %) was fed through the line 2 at a rate of approximately 2.0 kg/Hr.

The reaction solution recovered in the storage tank 105 was analyzed by liquid chromatography and $^1$H-NMR. As a result, it was found that the reaction solution was a solution containing a 4,4'-methylenebis(cyclohexane-4,1-diyl)di(carbamic acid phenyl ester), and that the yield of the 4,4'-methylenebis(cyclohexane-4,1-diyl)di(carbamic acid phenyl ester) was approximately 95% based on 4,4'-methylenebis (cyclohexylamine).

In addition, from the above described results of Reference Example 3, it was assumed that a compound having a urea bond was generated (the thermal dissociation temperature of the urea bond: 210° C.) in the production of an N-substituted carbamic acid ester in the present step. In the present example, on the 15$^{th}$ plate for supplying the mixed solution of diphenyl carbonate and phenol, the compound having the urea bond reacted with the diphenyl carbonate under heating at a temperature equal to or higher than the thermal dissociation temperature of the urea bond (220° C.) to generate an N-substituted carbamic acid ester. Thus, it was considered that the N-substituted carbamic acid ester could be obtained at a high yield.

Reference Example 4

Step (D-1): Production of N-substituted Carbamic Acid Ester

Using the reaction vessel shown in FIG. 1, an N-substituted carbamic acid ester was produced.

3.6 kg (29.5 mol) of 2,4-toluenediamine, 10.8 kg (53.5 mol) of bis(3-methylbutyl)carbonate, and 8.6 kg (85.1 mol) of 3-methyl-1-butanol were mixed to prepare a raw material solution. Thereafter, phenol was added into a plate-type distillation column 102 having 40 plates, and 3-methyl-1-butanol was then boiled with a reboiler 105, so that it could be in a total reflux state. At this time, the pressure of the column top was 9.6 atmospheric pressures, and the temperature of the 15$^{th}$ plate (counted from the top side) on which a line 2 was equipped was 220° C. Through a line 1 equipped on the uppermost plate (the first plate) of the distillation column 102, a mixed solution having the same composition as that of the raw material solution was introduced into the column at a rate of approximately 2.8 kg/Hr. After operation conditions had been stabilized, the raw material solution was supplied through the line 1 at a rate of approximately 2.8 kg/Hr, and the reaction solution was then recovered into a storage tank 105 through a line 6 equipped at the lowermost portion of the distillation column 102.

The reaction solution recovered in the storage tank 105 was analyzed by liquid chromatography and $^1$H-NMR. As a result, it was found that the reaction solution was a solution containing a 4-methyl-1,3-phenylenedi(carbamic acid(3-methylbutyl)ester), and that the yield of the 4-methyl-1,3-phenylenedi(carbamic acid(3-methylbutyl)ester) was approximately 78% based on 2,4-toluenediamine. In addition, this reaction solution contained approximately 15% by mass of 5,5'-carbonylbis(azanediyl)bis(2-methyl-5,1-phenylene)di (carbamic acid (3-methylbutyl)ester) as a compound having a urea bond. The thermal dissociation temperature of the urea bond contained in the 5,5'-carbonylbis(azanediyl)bis(2-methyl-5,1-phenylene)di(carbamic acid(3-methylbutyl)ester) was 208° C.

Example 7

Step (7-1): Production of N-substituted Carbamic Acid Ester

The same method as that in the step (D-1) of Reference example 4 was carried out, with the exception that a mixed solution of bis(3-methylbutyl)carbonate and 3-methyl-1-butanol (di(3-methylbutyl)carbonate concentration: approximately 50 wt %) was fed through the line 2 at a rate of approximately 2.2 kg/Hr.

The reaction solution recovered in the storage tank 105 was analyzed by liquid chromatography and $^1$H-NMR. As a result, it was found that the reaction solution was a solution containing a 4-methyl-1,3-phenylenedi(carbamic acid(3-methylbutyl)ester), and that the yield of the 4-methyl-1,3-phenylenedi(carbamic acid(3-methylbutyl)ester) was approximately 93% based on 2,4-toluenediamine.

In addition, from the above described results of Reference Example 4, it was assumed that a compound having a urea bond was generated (the thermal dissociation temperature of the urea bond: 208° C.) in the production of an N-substituted carbamic acid ester in the present step. In the present example, on the 15$^{th}$ plate for supplying the mixed solution of bis(3-methylbutyl) carbonate and phenol, the compound having the urea bond reacted with the diphenyl carbonate under heating at a temperature equal to or higher than the thermal dissociation temperature of the urea bond (220° C.) to generate an N-substituted carbamic acid ester. Thus, it was considered that the N-substituted carbamic acid ester could be obtained at a high yield.

Example 8

Step (8-1): Production of N-substituted Carbamic Acid Ester

Using the reaction vessel shown in FIG. 1, an N-substituted carbamic acid ester was produced.

4.3 kg of a polyurethane-urea copolymer produced from polyhexamethylene glycol, 4,4'-diphenylmethane diisocyanate and ethylenediamine was mixed with 10.3 kg of 4-(1,1,3, 3-tetramethylbutyl)phenol to prepare a raw material solution. Thereafter, 4-(1,1,3,3-tetramethylbutyl)phenol was added into a plate-type distillation column 102 having 40 plates, and it was then boiled with a reboiler 105, so that it could be in a total reflux state. At this time, the pressure of the column top was 10 kPa, and the temperature of the 15$^{th}$ plate (counted from the column top side) on which a line 2 was equipped was 230° C. This temperature was higher than the thermal dissociation temperature (210° C.) of the urea bond of the polyurethane-urea copolymer, which had been measured, separately. Through a line 1 equipped on the uppermost plate (the first plate) of the distillation column 102, a mixed solution having the same composition as that of the raw material solution was introduced into the column at a rate of approximately 2.2 kg/Hr. At the same time, through the line 2, a mixed solution of urea and 4-(1,1,3,3-tetramethylbutyl)phenol (urea concentration: approximately 5 wt %) was fed to the column at a rate of approximately 8.2 kg/Hr. After operation conditions had been stabilized, the raw material solution was supplied through the line 1 at a rate of approximately 2.2 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 85° C. The thus obtained ingredient was recovered into a storage tank 104.

The reaction solution recovered in the storage tank 105 was analyzed by liquid chromatography and $^1$H-NMR. As a result, it was found that the reaction solution was a solution containing a 4,4'-methylenebis(4,1-phenylene)di(carbamic acid(4-(1,1,3,3-tetramethylbutyl)phenyl)ester).

Example 9

Step (9-1): Production of N-substituted Carbamic Acid Ester

Using the reaction vessel shown in FIG. 1, an N-substituted carbamic acid ester was produced.

2.3 kg (19.8 mol) of 1,6-hexamethylenediamine, 28.3 kg (138 mol) of 4-(1,1,3,3-tetramethylbutyl)phenol, and 2.7 kg (45.0 mol) of urea were mixed to prepare a raw material solution. Thereafter, a plate-type distillation column 102 having 40 plates was heated, so that the pressure of the column top thereof was set at approximately 10 kPa. At this time, the temperature of the 15$^{th}$ plate (counted from the column top side) on which a line 2 was equipped was 240° C. Through a line 1 equipped on the uppermost plate (the first plate) of the distillation column 102, a mixed solution having the same composition as that of the raw material solution was introduced into the column at a rate of approximately 3.1 kg/Hr. At the same time, through the line 2, a mixed solution of urea and 4-(1,1,3,3-tetramethylbutyl)phenol (urea concentration: approximately 5 wt %) was fed to the column at a rate of approximately 4.8 kg/Hr. After operation conditions had been stabilized, the raw material solution was supplied through the line 1 at a rate of approximately 3.1 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 85° C. The thus obtained ingredient was recovered into a storage tank 104.

The reaction solution recovered in the storage tank 105 was analyzed by liquid chromatography and $^1$H-NMR. As a result, it was found that the reaction solution was a solution containing an N,N'-hexanediyl-di(carbamic acid(4-(1,1,3,3-tetramethylbutyl)phenyl)ester), and that the yield of the N,N'-hexanediyl-di(carbamic acid(4-(1,1,3,3-tetramethylbutyl)phenyl)ester) was approximately 95% based on 1,6-hexamethylenediamine.

In addition, from the results of the after-mentioned Comparative Example 1, it was assumed that a compound having a urea bond was generated (the thermal dissociation temperature of the urea bond: 220° C.) in the production of an N-substituted carbamic acid ester in the present step. In the present example, as described above, on the 15$^{th}$ plate for supplying the mixed solution of urea and 4-(1,1,3,3-tetramethylbutyl) phenol, the compound having the urea bond reacted with urea under heating at a temperature equal to or higher than the thermal dissociation temperature of the urea bond (240° C.) to generate an N-substituted carbamic acid ester. Thus, it was considered that the N-substituted carbamic acid ester could be obtained at a high yield.

On the other hand, the ingredient recovered in the storage tank 104 was subjected to $^1$H-NMR measurement. As a result, it was found that the ingredient was a mixture containing 4-(1,1,3,3-tetramethylbutyl)phenol and urea, and that the urea concentration was 9.5 mass %.

Step (9-2): Recycling of Mixture Obtained Using Condenser

Using the mixture recovered in the storage tank 104 in the step (9-1), an N-substituted carbamic acid ester was produced.

The concentration of ammonia in the mixture recovered in the storage tank 104 in the step (9-1) was 440 ppm. 2.3 kg of 1,6-hexamethylenediamine was added to 27.2 kg of the mixture to prepare a raw material solution. Using the raw material solution, the same method as that in the step (9-1) was carried out. As a result, N,N'-hexanediyl-di(carbamic acid(4-(1,1,3, 3-tetramethylbutyl)phenyl)ester) was obtained. The yield of the N,N'-hexanediyl-di(carbamic acid(4-(1,1,3,3-tetramethylbutyl)phenyl)ester) was approximately 95% based on 1,6-hexamethylenediamine.

Figure 2:
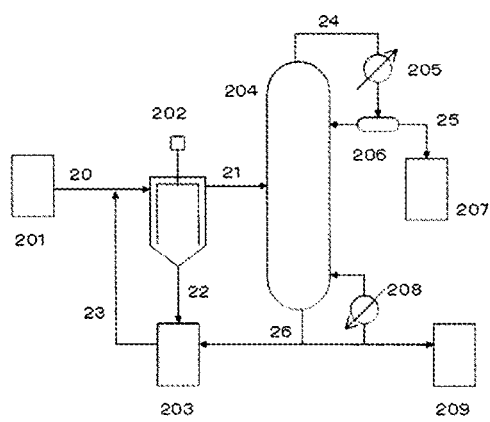
FIG. 2 is a schematic view showing an example of the reaction apparatus used in the production method of the present embodiment.

Step (9-3): Production of Isocyanate by Pyrolysis of N-substituted Carbamic Acid Ester Using the apparatus shown in FIG. 2, an isocyanate was produced.

A thin-film distillation apparatus 202 having a heating surface area of 0.1 m$^2$ was heated to 220° C., so that the pressure in the thin-film distillation apparatus was set at approximately 1.3 kPa. The reaction solution recovered in the storage tank 105 in the step (9-1) was added into a storage tank 201, and it was then supplied via a line 20 to the thin-film distillation apparatus 202 at a rate of approximately 1.8 kg/Hr. A liquid ingredient was discharged from a line 22 equipped at the bottom portion of the thin-film distillation apparatus 202, and it was then recovered in a storage tank 203. A gaseous ingredient containing hexamethylene diisocyanate and 4-(1,1,3,3-tetramethylbutyl)phenol was discharged from a line 21 equipped on the upper portion of the thin-film distillation apparatus 202.

The gaseous ingredient was introduced into a distillation column 204, and hexamethylene diisocyanate was separated from 4-(1,1,3,3-tetramethylbutyl)phenol by distillation. A portion of a high-boiling ingredient containing 4-(1,1,3,3-tetramethylbutyl)phenol was returned to the storage tank 203 via a line 26 equipped at the bottom portion of a distillation column 204, another portion was supplied to the distillation column 204 again via a reboiler 208, and the remaining portion was recovered in a storage tank 209. A gaseous phase ingredient containing hexamethylene diisocyanate was discharged via a line 24 from the column top of the distillation column 204, it was then condensed with a condenser 205, and a portion of the condensate was returned to the distillation column 204. A condensate containing hexamethylene diisocyanate was obtained in a storage tank 207. The yield was approximately 90% based on 1,6-hexamethylenediamine.

Comparative Example 1

Step (E-1): Production of N-substituted Carbamic Acid Ester

The same method as that in the step (9-1) of Example 9 was carried out, with the exception that a mixture of urea and 4-(1,1,3,3-tetramethylbutyl)phenol was not supplied via the line 2.

The reaction solution recovered in the storage tank 105 was analyzed by liquid chromatography and $^1$H-NMR. As a result, it was found that the reaction solution was a solution containing an N,N'-hexanediyl-di(carbamic acid(4-(1,1,3,3-tetramethylbutyl)phenyl)ester), and that the yield of the N,N'-hexanediyl-di(carbamic acid(4-(1,1,3,3-tetramethylbutyl)phenyl)ester) was approximately 72% based on 1,6-hexamethylenediamine. In addition, the reaction solution contained a 6,6'-carbonylbis(azanediyl)bis(hexane-6,1-diyl)di(carbamic acid(4-(1,1,3,3-tetramethylbutyl)phenyl ester) as a compound having a urea bond. The yield of the 6,6'-carbonylbis(azanediyl)bis(hexane-6,1-diyl)di(carbamic acid (4-(1,1,3,3-tetramethylbutyl)phenyl)ester) was approximately 22% based on 1,6-hexamethylenediamine. The thermal dissociation temperature of the urea bond of the 6,6'-carbonylbis(azanediyl)bis(hexane-6,1-diyl)di(carbamic acid(4-(1,1,3,3-tetramethylbutyl) phenyl) ester) was 220° C.

Moreover, the reaction solution was collected from a sampling port equipped on the 15$^{th}$ plate of the distillation column during the steady operation, and it was then analyzed. As a result, urea was not detected. Furthermore, the reaction solution was collected from a sampling port equipped on the 4$^{th}$ plate of the distillation column, in which the temperature was less than the thermal dissociation temperature of the urea bond (220° C.), and it was then analyzed. As a result, urea was not detected.

Comparative Example 2

Step (F-1): Production of N-substituted Carbamic Acid Ester

The same method as that in the step (9-1) of Example 9 was carried out, with the exception that the temperature on the 15$^{th}$ plate of the distillation column was set at 200° C. It is to be noted that the temperatures on the plates on which the reaction in the distillation column took place were all less than the thermal dissociation temperature of the urea bond (220° C.)

The reaction solution recovered in the storage tank 105 was analyzed by liquid chromatography and $^1$H-NMR. As a result, it was found that the reaction solution was a solution containing an N,N'-hexanediyl-di(carbamic acid(4-(1,1,3,3-tetramethylbutyl)phenyl)ester), and that the yield of the N,N'-hexanediyl-di(carbamic acid(4-(1,1,3,3-tetramethylbutyl)phenyl)ester) was approximately 48% based on 1,6-hexamethylenediamine. In addition, the reaction solution contained a 6,6'-carbonylbis(azanediyl)bis(hexane-6,1-diyl)di(carbamic acid(4-(1,1,3,3-tetramethylbutyl)phenyl ester) as a compound having a urea bond, and the yield of the 6,6'-carbonylbis(azanediyl)bis(hexane-6,1-diyl)di(carbamic acid(4-(1,1,3,3-tetramethylbutyl)phenyl ester) was approximately 31% based on 1,6-hexamethylenediamine. The thermal dissociation temperature of the urea bond of the 6,6'-carbonylbis(azanediyl)bis(hexane-6,1-diyl)di(carbamic acid (4-(1,1,3,3-tetramethylbutyl)phenyl ester) was 220° C.

Example 10

Step (10-1): Production of N-substituted Carbamic Acid Ester

Figure 3:
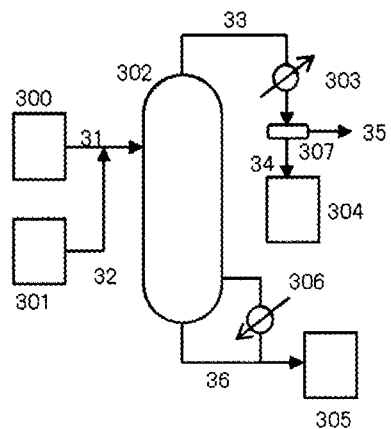
FIG. 3 is a schematic view showing an example of the reaction apparatus used in the production method of the present embodiment.

Using the apparatus shown in FIG. 3, an N-substituted carbamic acid ester was produced.

2.3 kg (19.8 mol) of 1,6-hexamethylenediamine, 28.3 kg (138 mol) of 4-(1,1,3,3-tetramethylbutyl)phenol, and 2.7 kg (45.0 mol) of urea were mixed to prepare a raw material solution. Thereafter, a plate-type distillation column 302 having 40 plates was heated, so that the pressure of the column top thereof was set at approximately 30 kPa. At this time, a line 31 and a line 32 were equipped on the uppermost plate (the first plate) of the distillation column 302, and the temperature of the first plate was 235° C. Through the line 31 equipped on the uppermost plate (the first plate) of the distillation column 302, a mixed solution having the same composition as that of the raw material solution was introduced into the column at a rate of approximately 3.1 kg/Hr. At the same time, through the line 32, a mixed solution of urea and 4-(1,1,3,3-tetramethylbutyl)phenol (urea concentration: approximately 5 wt %) was fed to the column at a rate of approximately 4.8 kg/Hr. After operation conditions had been stabilized, the raw material solution was supplied through the line 31 at a rate of approximately 3.1 kg/Hr, and the reaction solution was then recovered into a storage tank 305 through a line 36 equipped at the lowermost portion of the distillation column 302. A gaseous phase ingredient was recovered through a line 33 equipped at the uppermost portion of the distillation column 302, and it was then condensed using a condenser 303 that was retained at approximately 85° C. The thus obtained ingredient was recovered into a storage tank 304.

The reaction solution recovered in the storage tank 305 was analyzed by liquid chromatography and $^1$H-NMR. As a result, it was found that the reaction solution was a solution containing an N,N'-hexanediyl-di(carbamic acid(4-(1,1,3,3-tetramethylbutyl)phenyl)ester), and that the yield of the N,N'-hexanediyl-di(carbamic acid(4-(1,1,3,3-tetramethylbutyl)phenyl)ester) was approximately 82% based on 1,6-hexamethylenediamine.

In addition, from the above described results of Comparative Example 1, it was assumed that a compound having a urea bond was generated (the thermal dissociation temperature of the urea bond: 220° C.) in the production of an N-substituted carbamic acid ester in the present step. In the present example, as described above, on the first plate for supplying the mixed solution of urea and 4-(1,1,3,3-tetramethylbutyl)phenol, the compound having the urea bond reacted with urea under heating at a temperature equal to or higher than the thermal dissociation temperature of the urea bond (235° C.) to generate an N-substituted carbamic acid ester. Thus, it was considered that the N-substituted carbamic acid ester could be obtained at a high yield.

Example 11

Step (11-1): Production of N-substituted Carbamic Acid Ester

Figure 4:
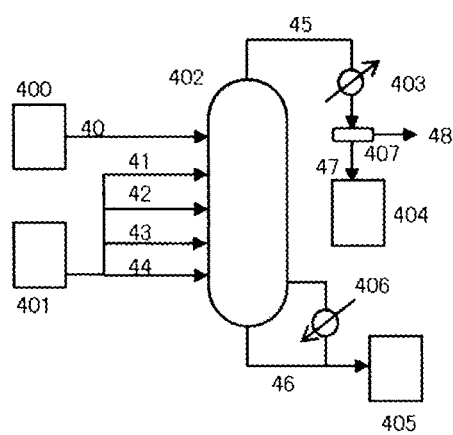
FIG. 4 is a schematic view showing an example of the reaction apparatus used in the production method of the present embodiment.

Using the reaction vessel shown in FIG. 4, an N-substituted carbamic acid ester was produced.

3.20 kg (27.6 mol) of 1,6-hexamethylenediamine, 102.0 kg (481 mol) of 4-(α,α-dimethylbenzyl)phenol, and 5.1 kg (85.0 mol) of urea were mixed to prepare a raw material solution. Thereafter, a plate-type distillation column 402 having 30 plates was heated, so that the pressure of the column top thereof was set at approximately 2 kPa. Thereafter, the total reflux operation of the 4-(α,α-dimethylbenzyl)phenol was conducted. At this time, the temperature of the uppermost plate (the first plate) of the distillation column 402 comprising a line 40 for supplying the raw material solution was 200° C. Through the line 40 equipped on the uppermost plate (the first plate) of the distillation column 402, a mixed solution having the same composition as that of the raw material solution was introduced into the column at a rate of approximately 3.2 kg/Hr. At the same time, through a line 41 equipped on the third plate of the distillation column, a mixed solution of urea and 4-(α,α-dimethylbenzyl)phenol (urea concentration: approximately 7.5 wt %) was fed to the column at a rate of approximately 1.34 kg/Hr. After operation conditions had been stabilized, the raw material solution was supplied through the line 40 at a rate of approximately 3.2 kg/Hr, and the reaction solution was then recovered into a storage tank 405 through a line 46 equipped at the lowermost portion of the distillation column 402. A gaseous phase ingredient was recovered into a storage tank 404 through a line 45 equipped at the uppermost portion of the distillation column 402, and it was then condensed using a condenser 403 that was retained at approximately 85° C. The temperature of the third plate on which the line 41 was equipped was 215° C.

The reaction solution recovered in the storage tank 405 was analyzed by liquid chromatography and $^1$H-NMR. As a result, it was found that the reaction solution was a solution containing an N,N'-hexanediyl-di(carbamic acid(4-(α,α-dimethylbenzyl)phenyl)ester), and that the yield of the N,N'-hexanediyl-di(carbamic acid(4-(α,α-dimethylbenzyl)phenyl)ester) was approximately 83% based on 1,6-hexamethylenediamine.

In addition, from the results of the after-mentioned Comparative Example 3, it was assumed that a compound having a urea bond was generated (the thermal dissociation temperature of the urea bond: 210° C.) in the production of an N-substituted carbamic acid ester in the present step. In the present example, as described above, on the third plate for supplying the mixed solution of urea and 4-(α,α-dimethylbenzyl)phenol, the compound having the urea bond reacted with urea under heating at a temperature equal to or higher than the thermal dissociation temperature of the urea bond (210° C.) to generate an N-substituted carbamic acid ester. Thus, it was considered that the N-substituted carbamic acid ester could be obtained at a high yield.

Comparative Example 3

Step (G-1)

The same method as that in the step (11-1) of Example 11 was carried out, with the exception that a mixture of urea and 4-(α,α-dimethylbenzyl)phenol was not fed through the line 41 equipped on the third plate of the distillation column.

The reaction solution recovered in the storage tank 105 was analyzed by liquid chromatography and $^1$H-NMR. As a result, it was found that the reaction solution was a solution containing an N,N'-hexanediyl-di(carbamic acid(4-(α,α-dimethylbenzyl)phenyl)ester), and that the yield of the N,N'-hexanediyl-di(carbamic acid(4-(α,α-dimethylbenzyl)phenyl)ester) was approximately 52% based on 1,6-hexamethylenediamine. In addition, the reaction solution contained a 6,6'-carbonylbis(azanediyl)bis(hexane-6,1-diyl)di(carbamic acid(4-(α,α-dimethylbenzyl)phenyl ester) as a compound having a urea bond. The yield of the 6,6'-carbonylbis(azanediyl)bis(hexane-6,1-diyl)di(carbamic acid(4-(α,α-dimethylbenzyl)phenyl ester) was approximately 30% based on 1,6-hexamethylenediamine. The thermal dissociation temperature of the urea bond of the 6,6'-carbonylbis(azanediyl)bis(hexane-6,1-diyl)di(carbamic acid(4-(α,α-dimethylbenzyl)phenyl ester) was 210° C.

Moreover, during the steady operation, the reaction solution was collected from a sampling port equipped on the second plate of the distillation column, in which the temperature was less than the thermal dissociation temperature of the urea bond (210° C.), and it was then analyzed. As a result, urea was not detected.

Example 12

Step (12-1): Production of N-substituted Carbamic Acid Ester

The same method as that in the step (11-1) of Example 11 was carried out, with the exception that a mixed solution of urea and 4-(α,α-dimethylbenzyl)phenol (urea concentration: approximately 7.5 wt %) was fed at a rate of approximately 1.34 kg/Hr, through a line 42 equipped on the 5$^{th}$ plate of the distillation column, instead of the line 41 equipped on the third plate thereof.

The reaction solution recovered in the storage tank 405 was analyzed by liquid chromatography and $^1$H-NMR. As a result, it was found that the reaction solution was a solution containing an N,N'-hexanediyl-di(carbamic acid(4-(α,α-dimethylbenzyl)phenyl)ester), and that the yield of the N,N'-hexanediyl-di(carbamic acid(4-(α,α-dimethylbenzyl)phenyl)ester) was approximately 89% based on 1,6-hexamethylenediamine.

In addition, from the above described results of Comparative Example 3, it was assumed that a compound having a urea bond was generated (the thermal dissociation temperature of the urea bond: 210° C.) in the production of an N-substituted carbamic acid ester in the present step. In the present example, as described above, on the 5$^{th}$ plate for supplying the mixed solution of urea and 4-(α,α-dimethylbenzyl)phenol, the compound having the urea bond reacted with urea under heating at a temperature equal to or higher than the thermal dissociation temperature of the urea bond to generate an N-substituted carbamic acid ester. Thus, it was considered that the N-substituted carbamic acid ester could be obtained at a high yield.

Example 13

Step (13-1): Production of N-substituted Carbamic Acid Ester

The same method as that in the step (11-1) of Example 11 was carried out, with the exception that a mixed solution of urea and 4-(α,α-dimethylbenzyl)phenol (urea concentration: approximately 7.5 wt %) was fed at a rate of approximately 1.34 kg/Hr, through a line 43 equipped on the 7$^{th}$ plate of the distillation column, instead of the line 41 equipped on the third plate thereof.

The reaction solution recovered in the storage tank 405 was analyzed by liquid chromatography and $^1$H-NMR. As a result, it was found that the reaction solution was a solution containing an N,N'-hexanediyl-di(carbamic acid(4-(α,α-dimethylbenzyl)phenyl)ester), and that the yield of the N,N'-hexanediyl-di(carbamic acid(4-(α,α-dimethylbenzyl)phenyl)ester) was approximately 96% based on 1,6-hexamethylenediamine.

In addition, from the above described results of Comparative Example 3, it was assumed that a compound having a urea bond was generated (the thermal dissociation temperature of the urea bond: 210° C.) in the production of an N-substituted carbamic acid ester in the present step. In the present example, as described above, on the 7$^{th}$ plate for supplying the mixed solution of urea and 4-(α,α-dimethylbenzyl)phenol, the compound having the urea bond reacted with urea under heating at a temperature equal to or higher than the thermal dissociation temperature of the urea bond to generate an N-substituted carbamic acid ester. Thus, it was considered that the N-substituted carbamic acid ester could be obtained at a high yield.

Example 14

Step (14-1): Production of N-substituted Carbamic Acid Ester

The same method as that in the step (11-1) of Example 11 was carried out, with the exception that a mixed solution of urea and 4-(α,α-dimethylbenzyl)phenol (urea concentration: approximately 7.5 wt %) was fed at a rate of approximately 1.34 kg/Hr, through a line 44 equipped on the 10$^{th}$ plate of the distillation column, instead of the line 41 equipped on the third plate thereof.

The reaction solution recovered in the storage tank 405 was analyzed by liquid chromatography and $^1$H-NMR. As a result, it was found that the reaction solution was a solution containing an N,N'-hexanediyl-di(carbamic acid(4-(α,α-dimethylbenzyl)phenyl)ester), and that the yield of the N,N'-hexanediyl-di(carbamic acid(4-(α,α-dimethylbenzyl)phenyl)ester) was approximately 96% based on 1,6-hexamethylenediamine.

In addition, from the above described results of Comparative Example 3, it was assumed that a compound having a urea bond was generated (the thermal dissociation temperature of the urea bond: 210° C.) in the production of an N-substituted carbamic acid ester in the present step. In the present example, as described above, on the 10$^{th}$ plate for supplying the mixed solution of urea and 4-(α,α-dimethylbenzyl)phenol, the compound having the urea bond reacted with urea under heating at a temperature equal to or higher than the thermal dissociation temperature of the urea bond to generate an N-substituted carbamic acid ester. Thus, it was considered that the N-substituted carbamic acid ester could be obtained at a high yield.

On the other hand, the ingredient recovered in the storage tank 404 was subjected to $^1$H-NMR measurement. As a result, it was found that the ingredient was a mixture containing 4-(α,α-dimethylbenzyl)phenol and urea, and that the urea concentration was 5.0 mass %.

Step (14-2): Recycling of Mixture Obtained Using Condenser

Using the mixture recovered in the storage tank 404 in the step (14-1), an N-substituted carbamic acid ester was produced.

The concentration of ammonia in the mixture recovered in the storage tank 404 in the step (14-1) was 630 ppm. 3.2 kg of 1,6-hexamethylenediamine was added to 71.7 kg of the mixture to prepare a raw material solution. Using the raw material solution, the same method as that in the step (14-1) was carried out. As a result, N,N'-hexanediyl-di(carbamic acid(4-(α,α-dimethylbenzyl)phenyl)ester) was obtained. The yield of the N,N'-hexanediyl-di(carbamic acid(4-(α,α-dimethylbenzyl)phenyl)ester) was approximately 96% based on 1,6-hexamethylenediamine.

Step (14-3): Production of Isocyanate by Pyrolysis of N-substituted Carbamic Acid Ester Using the apparatus shown in FIG. 2, an isocyanate was produced.

A thin-film distillation apparatus 202 having a heating surface area of 0.1 m$^2$ was heated to 220° C., so that the pressure in the thin-film distillation apparatus was set at approximately 1.3 kPa. The same method as that in the step (9-3) of Example 9 was carried out, with the exception that the reaction solution recovered in the storage tank 405 in the step (14-1) was added into a storage tank 201, and it was then supplied via a line 20 to the thin-film distillation apparatus 202 at a rate of approximately 2.0 kg/Hr. A condensate containing hexamethylene diisocyanate was recovered in a storage tank 207.

Example 15

Step (15-1): Production of N-substituted Carbamic Acid Ester

Figure 5:
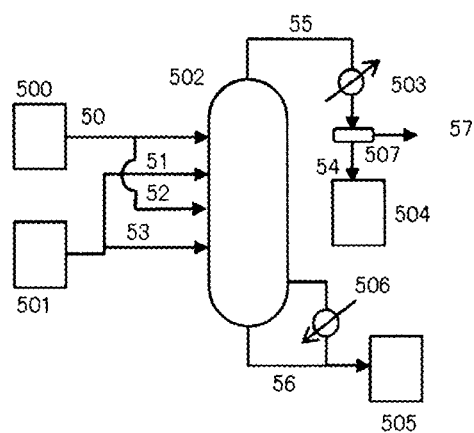
FIG. 5 is a schematic view showing an example of the reaction apparatus used in the production method of the present embodiment.

Using the reaction vessel shown in FIG. 5, an N-substituted carbamic acid ester was produced.

3.20 kg (27.6 mol) of 1,6-hexamethylenediamine, 102.0 kg (481 mol) of 4-(α,α-dimethylbenzyl)phenol, and 5.1 kg (85.0 mol) of urea were mixed to prepare a raw material solution. Thereafter, a plate-type distillation column 502 having 30 plates was heated, so that the pressure of the column top thereof was set at approximately 8 kPa. Thereafter, the total reflux operation of the 4-(α,α-dimethylbenzyl)phenol was conducted. At this time, the temperature of the uppermost plate (the first plate) of the distillation column 502 comprising a line 50 for supplying the taw material solution was 240° C. and the temperature of the other plates was 240° C. or higher. Through the line 50 equipped on the uppermost plate (the first plate) of the distillation column 502, and also through a line 52 equipped on the 20$^{th}$ plate thereof, a mixed solution having the same composition as that of the raw material solution was each introduced into the column at a rate of approximately 1.6 kg/Hr. At the same time, through a line 51 equipped on the 15$^{th}$ plate of the distillation column 502, and also through a line 53 equipped on the 25$^{th}$ plate thereof, a mixed solution of urea and 4-(α,α-dimethylbenzyl)phenol (urea concentration: approximately 7.5 wt %) was each fed to the column at a rate of approximately 0.67 kg/Hr. After operation conditions had been stabilized, the raw material solution was each supplied through the line 50 and the line 52 at a rate of approximately 1.6 kg/Hr, and the reaction solution was then recovered into a storage tank 505 through a line 56 equipped at the lowermost portion of the distillation column 502. A gaseous phase ingredient was recovered through a line 55 equipped at the uppermost portion of the distillation column 502, and it was then condensed using a condenser 503 that was retained at approximately 85° C. The thus obtained ingredient was recovered in a storage tank 504.

The reaction solution recovered in the storage tank 505 was analyzed by liquid chromatography and $^1$H-NMR. As a result, it was found that the reaction solution was a solution containing an N,N'-hexanediyl-di(carbamic acid(4-(α,α-dimethylbenzyl)phenyl)ester), and that the yield of the N,N'-hexanediyl-di(carbamic acid(4-(α,α-dimethylbenzyl)phenyl)ester) was approximately 97% based on 1,6-hexamethylenediamine.

In addition, from the above described results of Comparative Example 3, it was assumed that a compound having a urea bond was generated (the thermal dissociation temperature of the urea bond: 210° C.) in the production of an N-substituted carbamic acid ester in the present step. In the present example, as described above, on the 15$^{th}$ and 25$^{th}$ plates for supplying the mixed solution of urea and 4-(α,α-dimethylbenzyl)phenol, the compound having the urea bond reacted with urea under heating at a temperature equal to or higher than the thermal dissociation temperature of the urea bond to generate an N-substituted carbamic acid ester. Thus, it was considered that the N-substituted carbamic acid ester could be obtained at a high yield.

Example 16

Step (16-1): Production of N-substituted Carbamic Acid Ester

Using the reaction vessel shown in FIG. 1, an N-substituted carbamic acid ester was produced.

The same method as that in the step (13-1) of Example 13 was carried out, with the exceptions that a raw material solution prepared by mixing 1.4 kg (12.1 mol) of 1,6-hexamethylenediamine, 38.3 kg (518 mol) of n-butanol, and 2.7 kg (45.0 mol) of urea was used, that the pressure of the column top thereof was set at approximately 1.2 kPa, and that through the line 1 equipped on the uppermost plate (the first plate) of the distillation column, the raw material solution was supplied to the column at a rate of approximately 2.8 kg/Hr, and through the line 2 equipped on the 15$^{th}$ plate of the distillation column, a mixed solution of urea and n-butanol (urea concentration: approximately 5 wt %) was supplied to the column at a rate of approximately 1.2 kg/Hr. At this time, the temperature of the 15$^{th}$ plate, on which the line 2 was equipped, was 220° C.

The reaction solution recovered in the storage tank 105 was analyzed by liquid chromatography and $^1$H-NMR. As a result, it was found that the reaction solution was a solution containing an N,N'-hexanediyl-di(carbamic acid(n-butyl)ester), and that the yield of the N,N'-hexanediyl-di(carbamic acid(n-butyl)ester) was approximately 90% based on 1,6-hexamethylenediamine.

In addition, from the results of the after-mentioned Reference Example 5, it was assumed that a compound having a urea bond was generated (the thermal dissociation temperature of the urea bond: 210° C.) in the production of an N-substituted carbamic acid ester in the present step. In the present example, as described above, on the 15$^{th}$ plate for supplying the mixed solution of urea and n-butanol, the compound having the urea bond reacted with urea under heating at a temperature equal to or higher than the thermal dissociation temperature of the urea bond (220° C.) to generate an N-substituted carbamic acid ester. Thus, it was considered that the N-substituted carbamic acid ester could be obtained at a high yield.

Reference Example 5

Step (H-1): Production of N-substituted Carbamic Acid Ester

The same method as that in the step (16-1) of Example 16 was carried out with the exception that a mixed solution of urea and n-butanol was not supplied through the line 2.

The reaction solution recovered in the storage tank 105 was analyzed by liquid chromatography and $^1$H-NMR. As a result, the reaction solution was a solution containing an N,N'-hexanediyl-di(carbamic acid(n-butyl)ester), and the yield of the N,N'-hexanediyl-di(carbamic acid(n-butyl)ester) was approximately 65% based on hexamethylenediamine. In addition, the reaction solution contained a 6,6'-carbonylbis (azanediyl)bis(hexane-6,1-diyl)di(carbamic acid(n-butyl)ester) as a compound having a urea bond. The yield of the 6,6'-carbonylbis(azanediyl)bis(hexane-6,1-diyl)di(carbamic acid(n-butyl)ester) was approximately 32% based on 1,6-hexamethylenediamine. The thermal dissociation temperature of the urea bond of the 6,6'-carbonylbis(azanediyl)bis (hexane-6,1-diyl)di(carbamic acid(n-butyl)ester) was 210° C.

Moreover, during the steady operation, the reaction solution was collected from a sampling port equipped on the 15$^{th}$ plate of the distillation column, and it was then analyzed. As a result, urea was not detected.

Example 17

Step (17-1): Production of Compound Having Ureido Group

Figure 6:
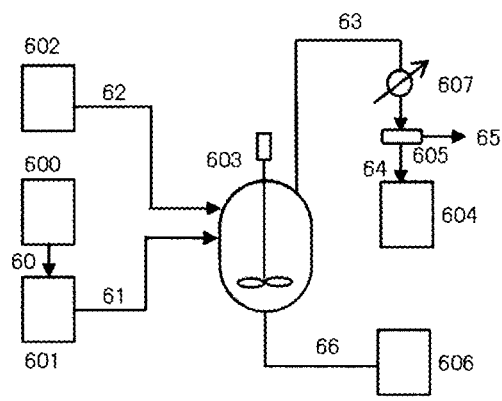
FIG. 6 is a schematic view showing an example of the reaction apparatus used in the production method of the present embodiment.

The apparatus shown in FIG. 6 was used.

In a state in which a line 66 was closed, 83.0 kg (392 mol) of 4-(α,α-dimethylbenzyl)phenol was mixed with 5.1 kg (85.0 mol) of urea in a storage tank 601 that had been heated to 120° C., and the mixed solution was then transferred into an agitation tank 603 that had been heated to 120° C. In a state in which the mixed solution was stirred in the agitation tank 603, 2.5 kg of 1,6-hexamethylenediamine was supplied from a storage tank 602 to the agitation tank 603, through a line 62, at a rate of approximately 2.0 kg/Hr. After completion of the supply of the 1,6-hexamethylenediamine, the mixture was stirred for approximately 4 hours, and the reaction solution was then sampled. The reaction solution was analyzed by liquid chromatography. As a result, 1,6-hexamethylene diurea was generated at a yield of approximately 97% based on 1,6-hexamethylenediamine.

Thereafter, the line 66 was opened, and the reaction solution was then transferred through the line 66 to a storage tank 606.

Step (17-2): Production of N-substituted Carbamic Acid Ester

The apparatus shown in FIG. 1 was used.

4-(α,α-dimethylbenzyl)phenol was added into a plate-type distillation column 102 having 40 plates, and it was then boiled with a reboiler 105, so that it could be in a total reflux state. At this time, the pressure of the column top was 2 kPa, and the temperature of the 15$^{th}$ plate (counted from the column top side) on which a line 2 was equipped was 240° C. Through a line 1 equipped on the uppermost plate (the first plate) of the distillation column 102, a mixed solution having the same composition as that of the reaction solution obtained in the step (17-1) was introduced into the column at a rate of approximately 2.0 kg/Hr. At the same time, through the line 2, a mixed solution of urea and 4-(α,α-dimethylbenzyl)phenol (urea concentration: approximately 7.5 wt %) was fed to the column at a rate of approximately 1.6 kg/Hr. After operation conditions had been stabilized, the reaction solution obtained in the step (17-1) was supplied through the line 1 at a rate of approximately 2.0 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 85° C. The thus obtained ingredient was recovered into a storage tank 104.

The reaction solution recovered in the storage tank 105 was analyzed by liquid chromatography and $^1$H-NMR. As a result, it was found that the reaction solution was a solution containing an N,N'-hexanediyl-di(carbamic acid(4-(α,α-dimethylbenzyl)phenyl)ester), and that the yield of the N,N'-hexanediyl-di(carbamic acid(4-(α,α-dimethylbenzyl)phenyl)ester) was approximately 95% based on 1,6-hexamethylenediamine.

In addition, from the results of the after-mentioned Comparative Example 4, it was assumed that a compound having a urea bond was generated (the thermal dissociation temperature of the urea bond: 210° C.) in the production of an N-substituted carbamic acid ester in the present step. In the present example, as described above, on the 15$^{th}$ plate for supplying the mixed solution of urea and 4-(α,α-dimethylbenzyl)phenol, the compound having the urea bond reacted with urea under heating at a temperature equal to or higher than the thermal dissociation temperature of the urea bond (240° C.) to generate an N-substituted carbamic acid ester. Thus, it was considered that the N-substituted carbamic acid ester could be obtained at a high yield.

Step (17-3)

The condensate recovered in the storage tank 104 in the step (17-2) was analyzed by liquid chromatography and $^1$H-NMR. As a result, it was found that the condensate was a solution containing urea, biutret and 4-(α,α-dimethylbenzyl) phenol, and that the urea was contained at a weight percentage of approximately 6.3% and the biuret was contained at a weight percentage of approximately 0.1%.

The same method as that in the step (17-2) was carried out with the exception that the condensate was fed through the line 2 at a rate of approximately 1.9 kg/Hr, instead of the mixed solution of urea and 4-(α,α-dimethylbenzyl)phenol (urea concentration: approximately 7.5 wt %).

The reaction solution recovered in the storage tank 105 was analyzed by liquid chromatography and $^1$H-NMR. As a result, it was found that the reaction solution was a solution containing N,N'-hexanediyl-di(carbamic acid(4-($\alpha,\alpha$-dimethylbenzyl)phenyl)ester), and that the yield of the N,N'-hexanediyl-di(carbamic acid(4-($\alpha,\alpha$-dimethylbenzyl)phenyl)ester) was approximately 95% based on 1,6-hexamethylenediamine.

Comparative Example 4

Step (I-1)
The same method as that in the step (17-1) of Example 17 was carried out to obtain a reaction solution containing 1,6-hexamethylene diurea.
Step (I-2)
The same method as that in the step (17-2) of Example 17 was carried out with the exception that the mixed solution of urea and 4-($\alpha,\alpha$-dimethylbenzyl)phenol was not fed through the line 2.
The reaction solution recovered in the storage tank 105 was analyzed by liquid chromatography and $^1$H-NMR. As a result, it was found that the reaction solution was a solution containing an N,N'-hexanediyl-di(carbamic acid(4-($\alpha,\alpha$-dimethylbenzyl)phenyl)ester), and that the yield of the N,N'-hexanediyl-di(carbamic acid(4-($\alpha,\alpha$-dimethylbenzyl)phenyl)ester) was approximately 57% based on hexamethylenediamine. In addition, the reaction solution contained a 6,6'-carbonylbis(azanediyl)bis(hexane-6,1-diyl) di(carbamic acid(4-($\alpha,\alpha$-dimethylbenzyl)phenyl)ester) as a compound containing a urea bond. The yield of the 6,6'-carbonylbis(azanediyl)bis(hexane-6,1-diyl)di(carbamic acid (4-($\alpha,\alpha$-dimethylbenzyl)phenyl)ester) was approximately 35% based on 1,6-hexamethylenediamine. The thermal dissociation temperature of the urea bond of the 6,6'-carbonylbis (azanediyl)bis(hexane-6,1-diyl)di(carbamic acid(4-($\alpha,\alpha$-dimethylbenzyl)phenyl)ester) was 210° C.

Moreover, the reaction solution was collected from a sampling port equipped on the 15$^{th}$ plate of the distillation column during the steady operation, and it was then analyzed. As a result, urea was not detected. Furthermore, the reaction solution was collected from a sampling port equipped on the 4$^{th}$ plate of the distillation column, in which the temperature was less than the thermal dissociation temperature of the urea bond (210° C.), and it was then analyzed. As a result, urea was not detected.

Example 18

Step (18-1): Production of Compound Having Ureido Group
The same method as that in the step (17-1) of Example 17 was carried out with the exceptions that 63.2 kg of n-butanol was used instead of 4-($\alpha,\alpha$-dimethylbenzyl)phenol, and that 2.4 kg (20.7 mol) of 1,6-hexamethylenediamine and 4.8 kg (80.0 mol) of urea were used. The reaction solution was sampled and was then analyzed by liquid chromatography. As a result, it was found that 1,6-hexamethylene diurea was generated at a yield of approximately 88% based on 1,6-hexamethylenediamine.
Step (18-2): Production of N-substituted Carbamic Acid Ester
The same method as that in the step (17-2) of Example 17 was carried out, with the exceptions that n-butanol was used instead of 4-($\alpha,\alpha$-dimethylbenzyl) phenol, that the pressure of the column top of the distillation column 102 was set at approximately 1.2 kPa, that the temperature of the 15$^{th}$ plate (counted from the column top side) on which the line 2 was equipped was set at 220° C., and that the reaction solution obtained in the step (18-1) was used instead of the reaction solution obtained in the step (17-1).

The reaction solution recovered in the storage tank 105 was analyzed by liquid chromatography and $^1$H-NMR. As a result, it was found that the reaction solution was a solution containing an N,N'-hexanediyl-di(carbamic acid(n-butyl)ester), and that the yield of the N,N'-hexanediyl-di(carbamic acid(n-butyl)ester) was approximately 85% based on 1,6-hexamethylenediamine.

Figure 7:
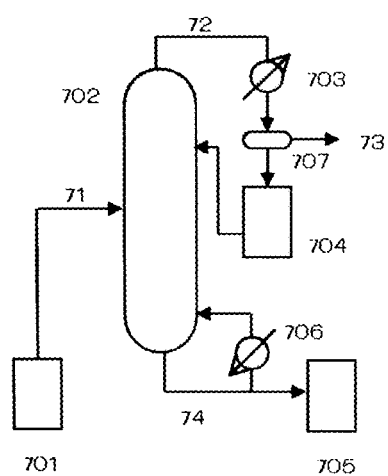
FIG. 7 is a schematic view showing an example of the reaction apparatus used in the production method of the present embodiment.

From the results of the after-mentioned Reference Example 6, it was assumed that a compound having a urea bond was generated (the thermal dissociation temperature of the urea bond: 210° C.) in the production of an N-substituted carbamic acid ester in the present step. In the present example, as described above, on the 15$^{th}$ plate for supplying the mixed solution of urea and n-butanol, the compound having the urea bond reacted with urea under heating at a temperature equal to or higher than the thermal dissociation temperature of the urea bond (220° C.) to generate an N-substituted carbamic acid ester. Thus, it was considered that the N-substituted carbamic acid ester could be obtained at a high yield.
Step (18-3): Transesterification
The apparatus shown in FIG. 7 was used.
The reaction solution recovered in the storage tank 105 in the step (18-2) was added into a storage tank 701, and thereafter, 2,4-di-tert-amyl phenol was added at a stoichiometric ratio of 10:1 based on the amount of N,N'-hexanediyl-di (carbamic acid(n-butyl)ester) contained in the reaction solution, and also, dibutyltin dilaurate was added at a stoichiometric ratio of 0.01:1 based on the same substance as described above, thereby preparing a homogeneous solution.

A packed column 702 filled with a filler (Heli-Pack No. 3) was heated to 240° C., and the pressure of the inside thereof was set at 26 kPa. Through a line 71 equipped in the packed column 702, the mixed solution contained in the storage tank 701 was fed to the column at a rate of approximately 1.2 kg/Hr. Through a line 74 equipped at the lowermost portion of the packed column 702, it was recovered in a storage tank 705. A gaseous phase ingredient was introduced into a condenser 703 through a line 72 equipped at the uppermost portion of the packed column 702, and the obtained liquid phase ingredient was then recovered in a storage tank 704 through a gas-liquid separator 707. The reaction solution recovered in the storage tank 705 was analyzed by liquid chromatography and $^1$H-NMR. As a result, it was found that the reaction solution contained an N,N'-hexanediyl-di(carbamic acid(2,4-di-tert-amylphenyl)ester), and that the yield of the N,N'-hexanediyl-di(carbamic acid(2,4-di-tert-amylphenyl)ester) was 85% based on N,N'-hexanediyl-di (carbamic acid(n-butyl)ester).

Reference Example 6

Step (J-1)
The same method as that in the step (18-1) of Example 18 was carried out to obtain a reaction solution containing 1,6-hexamethylene diurea.
Step (J-2)
The same method as that in the step (18-2) of Example 18 was carried out with the exception that the mixed solution of urea and n-butanol was not fed through the line 2.
The reaction solution recovered in the storage tank 105 was analyzed by liquid chromatography and $^1$H-NMR. As a result, it was found that the reaction solution was a solution containing an N,N'-hexanediyl-di(carbamic acid(n-butyl)ester), and that the yield of the N,N'-hexanediyl-di(carbamic acid(n-butyl)ester) was approximately 68% based on hexamethylenediamine. In addition, the reaction solution contained a 6,6'-carbonylbis(azanediyl)bis(hexane-6,1-diyl)di(carbamic acid(n-butyl)ester) as a compound having a urea bond. The yield of the 6,6'-carbonylbis(azanediyl)bis(hexane-6,1-diyl)di(carbamic acid(n-butyl)ester) was approximately 35% based on 1,6-hexamethylenediamine. The thermal dissociation temperature of the urea bond of the 6,6'-carbonylbis(azanediyl)bis(hexane-6,1-diyl)di(carbamic acid(n-butyl)ester) was 205° C.

Moreover, the reaction solution was collected from a sampling port equipped on the 15$^{th}$ plate of the distillation column during the steady operation, and it was then analyzed. As a result, urea was not detected.

Example 19

Step (19-1): Production of N-substituted Carbamic Acid Ester

The reaction vessel shown in FIG. 1 was used.

2.8 kg (16.4 mol) of 3-aminomethyl-3,5,5-trimethylcyclohexylamine, 42.8 kg (252 mol) of 4-phenyl phenol, and 3.2 kg (53.3 mol) of urea were mixed to prepare a raw material solution. Thereafter, a plate-type distillation column 102 having 40 plates was heated, so that the pressure of the column top thereof was set at approximately 10 kPa. At this time, the temperature of the 15$^{th}$ plate (counted from the column top side) on which a line 2 was equipped was 245° C. Through a line 1 equipped on the uppermost plate (the first plate) of the distillation column 102, a mixed solution having the same composition as that of the raw material solution was introduced into the column at a rate of approximately 2.8 kg/Hr. Through the line 2, a mixed solution of urea and 4-phenyl phenol (urea concentration: approximately 6.3 wt %) was fed to the column at a rate of approximately 1.8 kg/Hr. After operation conditions had been stabilized, the raw material solution was supplied through the line 1 at a rate of approximately 2.8 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 150° C. The thus obtained ingredient was recovered into a storage tank 104.

The reaction solution recovered in the storage tank 105 was analyzed by liquid chromatography and $^1$H-NMR. As a result, it was found that the reaction solution contained a 3-((4-phenylphenoxy)carbonylaminomethyl)-3,5,5-trimethylcyclohexyl carbamic acid(4-phenylphenyl)ester, and that the yield of the 3-((4-phenylphenoxy)carbonylaminomethyl)-3,5,5-trimethylcyclohexyl carbamic acid(4-phenylphenyl)ester was approximately 92% based on 3-aminomethyl-3,5,5-trimethylcyclohexylamine.

In addition, from the results of the after-mentioned Reference Example 7, it was assumed that a compound having a urea bond was generated (the thermal dissociation temperature of the urea bond: 220° C.) in the production of an N-substituted carbamic acid ester in the present step. In the present example, as described above, on the 15$^{th}$ plate for supplying the mixed solution of urea and 4-phenyl phenol, the compound having the urea bond reacted with urea under heating at a temperature equal to or higher than the thermal dissociation temperature of the urea bond (245° C.) to generate an N-substituted carbamic acid ester. Thus, it was considered that the N-substituted carbamic acid ester could be obtained at a high yield.

Reference Example 7

Step (K-1)

The same method as that in the step (19-1) of Example 19 was carried out with the exception that the mixed solution of urea and 4-phenyl phenol was not fed through the line 2.

The reaction solution recovered in the storage tank 105 was analyzed by liquid chromatography and $^1$H-NMR. As a result, it was found that the reaction solution contained a 3-((4-phenylphenoxy)carbonylaminomethyl)-3,5,5-trimethylcyclohexyl carbamic acid(4-phenylphenyl)ester, and that the yield of the 3-((4-phenylphenoxy)carbonylaminomethyl)-3,5,5-trimethylcyclohexyl carbamic acid(4-phenylphenyl)ester was approximately 61% based on 3-aminomethyl-3,5,5-trimethylcyclohexylamine. In addition, the reaction solution contained approximately 30% by mass of di(4-phenylphenyl)-5,5'-(carbonylbis(azanediyl)bis(methylene))bis(3,3,5-trimethylcyclohexane-5,1-diyl) dicarbamate as a compound having a urea bond. The thermal dissociation temperature of the urea bond of the di(4-phenylphenyl)-5,5'-(carbonylbis(azanediyl)bis(methylene))bis(3,3,5-trimethylcyclohexane-5,1-diyl) dicarbamate was 220° C.

Moreover, the reaction solution was collected from a sampling port equipped on the 15$^{th}$ plate of the distillation column during the steady operation, and it was then analyzed. As a result, urea was not detected.

Example 20

Step (20-1): Production of Compound Having Ureido Group

The apparatus shown in FIG. 6 was used.

In a state in which a line 66 was closed, 52.8 kg (249 mol) of 4-(α,α-dimethylbenzyl)phenol was mixed with 4.2 kg (70 mol) of urea in a storage tank 601 that had been heated to 120° C., and the mixed solution was then transferred into an agitation tank 603 that had been heated to 120° C. In a state in which the mixed solution was stirred in the agitation tank 603, 2.9 kg of 3-aminomethyl-3,5,5-trimethylcyclohexylamine was supplied from a storage tank 602 to the agitation tank 603, through a line 62, at a rate of approximately 1.8 kg/Hr. After completion of the supply of the 3-aminomethyl-3,5,5-trimethylcyclohexylamine, the mixture was stirred for approximately 4 hours, and the reaction solution was then sampled. The reaction solution was analyzed by liquid chromatography. As a result, 3-ureidomethyl-3,5,5-trimethylcyclohexyl urea was generated at a yield of approximately 97% based on 3-aminomethyl-3,5,5-trimethylcyclohexylamine.

Thereafter, the line 66 was opened, and the reaction solution was then transferred through the line 66 to a storage tank 606.

Step (20-2): Production of N-substituted Carbamic Acid Ester

The apparatus shown in FIG. 1 was used.

4-(α,α-dimethylbenzyl)phenol was added into a plate-type distillation column 102 having 40 plates, and it was then boiled with a reboiler 105, so that it could be in a total reflux state. At this time, the pressure of the column top was 1.5 kPa, and the temperature of the 15$^{th}$ plate (counted from the column top side) on which a line 2 was equipped was 230° C. Through a line 1 equipped on the uppermost plate (the first plate) of the distillation column 102, a mixed solution having the same composition as that of the reaction solution obtained in the step (20-1) was introduced into the column at a rate of approximately 1.9 kg/Hr. At the same time, through the line 2, a mixed solution of urea and 4-(α,α-dimethylbenzyl)phenol (urea concentration: approximately 5 wt %) was fed to the column at a rate of approximately 1.6 kg/Hr. After operation conditions had been stabilized, the reaction solution obtained in the step (20-1) was supplied through the line 1 at a rate of approximately 1.9 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 85° C. The thus obtained ingredient was recovered into a storage tank 104.

The reaction solution recovered in the storage tank 105 was analyzed by liquid chromatography and $^1$H-NMR. As a result, it was found that the reaction solution was a solution containing a 3-((4-(α,α-dimethylbenzyl)phenoxy)carbonylaminomethyl)-3,5,5-trimethylcyclohexyl carbamic acid(4-(α,α-dimethylbenzyl)phenyl)ester, and that the yield of the 3-((4-(α,α-dimethylbenzyl)phenoxy)carbonylaminomethyl)-3,5,5-trimethylcyclohexyl carbamic acid(4-(α,α-dimethylbenzyl)phenyl)ester was approximately 95% based on 3-aminomethyl-3,5,5-trimethylcyclohexylamine.

In addition, from the results of the after-mentioned Comparative Example 5, it was assumed that a compound having a urea bond was generated (the thermal dissociation temperature of the urea bond: 215° C.) in the production of an N-substituted carbamic acid ester in the present step. In the present example, as described above, on the 15$^{th}$ plate for supplying the mixed solution of urea and 4-(α,α-dimethylbenzyl)phenol, the compound having the urea bond reacted with urea under heating at a temperature equal to or higher than the thermal dissociation temperature of the urea bond (230° C.) to generate an N-substituted carbamic acid ester. Thus, it was considered that the N-substituted carbamic acid ester could be obtained at a high yield.

Comparative Example 5

Step (L-1)

The same method as that in the step (20-2) of Example 20 was carried out with the exception that the mixed solution of urea and 4-(α,α-dimethylbenzyl)phenol was not fed through the line 2.

The reaction solution recovered in the storage tank 105 was analyzed by liquid chromatography and $^1$H-NMR. As a result, it was found that the reaction solution contained a 3-((4-(α,α-dimethylbenzyl)phenoxy)carbonylaminomethyl)-3,5,5-trimethylcyclohexyl carbamic acid(4-(α,α-dimethylbenzyl)phenyl)ester, and that the yield of the 3-((4-(α,α-dimethylbenzyl)phenoxy)carbonylaminomethyl)-3,5,5-trimethylcyclohexyl carbamic acid(4-(α,α-dimethylbenzyl)phenyl)ester was approximately 48% based on 3-aminomethyl-3,5,5-trimethylcyclohexylamine. In addition, the reaction solution contained approximately 30% by mass of di(4-(α,α-dimethylbenzyl)phenyl)-5,5'-(carbonylbis(azanediyl)bis(methylene))bis(3,3,5-trimethylcyclohexane-5,1-diyl) dicarbamate as a compound having a urea bond. The thermal dissociation temperature of the urea bond of the di(4-(α,α-dimethylbenzyl)phenyl)-5,5'-(carbonylbis(azanediyl)bis(methylene))bis(3,3,5-trimethylcyclohexane-5,1-diyl) dicarbamate was 215° C.

Moreover, the reaction solution was collected from a sampling port equipped on the 15$^{th}$ plate of the distillation column during the steady operation, and it was then analyzed. As a result, urea was not detected. Furthermore, the reaction solution was collected from a sampling port equipped on the third plate of the distillation column, in which the temperature was less than the thermal dissociation temperature of the urea bond (215° C.), and it was then analyzed. As a result, urea was not detected.

Example 21

Step (21-1): Production of N-substituted Carbamic Acid Ester

The reaction vessel shown in FIG. 1 was used.

3.5 kg (16.6 mol) of 4,4'-methylenebis(cyclohexylamine), 62.1 kg (323 mol) of 4-heptyl phenol, and 3.8 kg (63.3 mol) of urea were mixed to prepare a raw material solution. Thereafter, a plate-type distillation column 102 having 40 plates was heated, so that the pressure of the column top thereof was set at approximately 3 kPa. At this time, the temperature of the 15$^{th}$ plate (counted from the column top side) on which a line 2 was equipped was 250° C. Through a line 1 equipped on the uppermost plate (the first plate) of the distillation column 102, a mixed solution having the same composition as that of the raw material solution was introduced into the column at a rate of approximately 2.1 kg/Hr. Through the line 2, a mixed solution of urea and 4-heptyl phenol (urea concentration: approximately 3.8 wt %) was fed to the column at a rate of approximately 1.6 kg/Hr. After operation conditions had been stabilized, the raw material solution was supplied through the line 1 at a rate of approximately 2.8 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 150° C. The thus obtained ingredient was recovered into a storage tank 104.

The reaction solution recovered in the storage tank 105 was analyzed by liquid chromatography and $^1$H-NMR. As a result, it was found that the reaction solution contained a 4,4'-(4,4'-carbonylbis(azanediyl)bis(cyclohexane-4,1-diyl)bis(methylene)di(carbamic acid(4-heptylphenyl)ester), and that the yield of the 4,4'-(4,4'-carbonylbis(azanediyl)bis(cyclohexane-4,1-diyl)bis(methylene)di(carbamic acid(4-heptylphenyl)ester) was approximately 90% based on 4,4'-methylenebis(cyclohexylamine).

In addition, from the results of the after-mentioned Reference Example 8, it was assumed that a compound having a urea bond was generated (the thermal dissociation temperature of the urea bond: 210° C.) in the production of an N-substituted carbamic acid ester in the present step. In the present example, as described above, on the 15$^{th}$ plate for supplying the mixed solution of urea and 4-heptyl phenol, the compound having the urea bond reacted with urea under heating at a temperature equal to or higher than the thermal dissociation temperature of the urea bond (250° C.) to generate an N-substituted carbamic acid ester. Thus, it was considered that the N-substituted carbamic acid ester could be obtained at a high yield.

Reference Example 8

Step (M -1)

The same method as that in the step (21-1) of Example 21 was carried out with the exception that the mixed solution of urea and 4-heptyl phenol was not fed through the line 2.

The reaction solution recovered in the storage tank 105 was analyzed by liquid chromatography and $^1$H-NMR. As a result, it was found that the reaction solution contained a 4,4'-methylenebis(cyclohexane-4,1-diyl)di(carbamic acid(4-heptylphenyl)ester), and that the yield of the 4,4'-methylenebis(cyclohexane-4,1-diyl)di(carbamic acid(4-heptylphenyl)ester) was approximately 55% based on 4,4'-methylenebis(cyclohexylamine). In addition, the reaction solution contained approximately 19% by mass of 4,4'-(4,4'-carbonylbis(azanediyl)bis(cyclohexane-4,1-diyl)bis(methylene))bis(cyclohexane-4,1-diyl)di(carbamic acid(4-heptylphenyl)ester) as a compound having a urea bond. The thermal dissociation temperature of the urea bond of the 4,4'-(4,4'-carbonylbis(azanediyl)bis(cyclohexane-4,1-diyl)bis(methylene))bis(cyclohexane-4,1-diyl)di(carbamic acid (4-heptylphenyl)ester) was 210° C.

Moreover, the reaction solution was collected from a sampling port equipped on the 15$^{th}$ plate of the distillation column during the steady operation, and it was then analyzed. As a result, urea was not detected.

Example 22

Step (22-1): Production of Compound Having Ureido Group
The apparatus shown in FIG. 6 was used.
In a state in which a line 66 was closed, 60.1 kg (273 mol) of 4-nonyl phenol was mixed with 3.5 kg (58.3 mol) of urea in a storage tank 601 that had been heated to 120° C., and the mixed solution was then transferred into an agitation tank 603 that had been heated to 120° C. In a state in which the mixed solution was stirred in the agitation tank 603, 2.8 kg of 4,4'-methylenebis(cyclohexylamine) was supplied from a storage tank 602 to the agitation tank 603, through a line 62, at a rate of approximately 3.0 kg/Hr. After completion of the supply of the 4,4'-methylenebis(cyclohexylamine), the mixture was stirred for approximately 4 hours, and the reaction solution was then sampled. The reaction solution was analyzed by liquid chromatography. As a result, 4,4'-methylenebis(cyclohexyl urea) was generated at a yield of approximately 99% based on 4,4'-methylenebis(cyclohexylamine).

Thereafter, the line 66 was opened, and the reaction solution was then transferred through the line 66 to a storage tank 606.
Step (22-2): Production of N-substituted Carbamic Acid Ester
The apparatus shown in FIG. 1 was used.
4-Nonyl phenol was added into a plate-type distillation column 102 having 40 plates, and it was then boiled with a reboiler 105, so that it could be in a total reflux state. At this time, the pressure of the column top was 2.5 kPa, and the temperature of the 15$^{th}$ plate (counted from the column top side) on which a line 2 was equipped was 240° C. Through a line 1 equipped on the uppermost plate (the first plate) of the distillation column 102, a mixed solution having the same composition as that of the reaction solution obtained in the step (26-1) was introduced into the column at a rate of approximately 1.9 kg/Hr. At the same time, through the line 2, a mixed solution of urea and 4-nonyl phenol (urea concentration: approximately 4.2 wt %) was fed to the column at a rate of approximately 1.2 kg/Hr. After operation conditions had been stabilized, the reaction solution obtained in the step (22-1) was supplied through the line 1 at a rate of approximately 1.9 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 85° C. The thus obtained ingredient was recovered into a storage tank 104.

The reaction solution recovered in the storage tank 105 was analyzed by liquid chromatography and $^1$H-NMR. As a result, it was found that the reaction solution was a solution containing a 4,4'-(4,4'-carbonylbis(azanediyl)bis(cyclohexane-4,1-diyl)bis(methylene)di(carbamic acid(4-nonylphenyl)ester), and that the yield of the 4,4'-(4,4'-carbonylbis(azanediyl)bis(cyclohexane-4,1-diyl)bis(methylene)di(carbamic acid(4-nonylphenyl)ester) was approximately 92% based on 4,4'-methylenebis(cyclohexylamine).

In addition, from the results of the after-mentioned Reference Example 9, it was assumed that a compound having a urea bond was generated (the thermal dissociation temperature of the urea bond: 210° C.) in the production of an N-substituted carbamic acid ester in the present step. In the present example, as described above, on the 15$^{th}$ plate for supplying the mixed solution of urea and 4-heptyl phenol, the compound having the urea bond reacted with urea under heating at a temperature equal to or higher than the thermal dissociation temperature of the urea bond (240° C.) to generate an N-substituted carbamic acid ester. Thus, it was considered that the N-substituted carbamic acid ester could be obtained at a high yield.

Reference Example 9

Step (N-1)
The same method as that in the step (22-2) of Example 22 was carried out with the exception that the mixed solution of urea and 4-nonyl phenol was not fed through the line 2.

The reaction solution recovered in the storage tank 105 was analyzed by liquid chromatography and $^1$H-NMR. As a result, it was found that the reaction solution contained a 4,4'-methylenebis(cyclohexane-4,1-diyl)di(carbamic acid(4-nonylphenyl)ester), and that the yield of the 4,4'-methylenebis(cyclohexane-4,1-diyl)di(carbamic acid(4-nonylphenyl)ester) was approximately 52% based on 4,4'-methylenebis(cyclohexylamine). In addition, the reaction solution contained approximately 19% by mass of 4,4'-(4,4'-carbonylbis(azanediyl)bis(cyclohexane-4,1-diyl)bis(methylene))bis(cyclohexane-4,1-diyl)di(carbamic acid(4-nonylphenyl)ester) as a compound having a urea bond. The thermal dissociation temperature of the urea bond of the 4,4'-(4,4'-carbonylbis(azanediyl)bis(cyclohexane-4,1-diyl)bis(methylene))bis(cyclohexane-4,1-diyl)di(carbamic acid (4-nonylphenyl)ester) was 210° C.

Moreover, the reaction solution was collected from a sampling port equipped on the 15$^{th}$ plate of the distillation column during the steady operation, and it was then analyzed. As a result, urea was not detected.

Example 23

Step (23-1): Production of N-substituted Carbamic Acid Ester
The reaction vessel shown in FIG. 1 was used.
1.6 kg (13.1 mol) of 2,4-toluenediamine, 37.8 kg (184 mol) of 4-(1,1,3,3-tetramethylbutyl)phenol, and 2.8 kg (46.7 mol) of urea were mixed to prepare a raw material solution. Thereafter, a plate-type distillation column 102 having 40 plates was heated, so that the pressure of the column top thereof was set at approximately 6 kPa. At this time, the temperature of the 15$^{th}$ plate (counted from the column top side) on which a line 2 was equipped was 250° C. Through a line 1 equipped on the uppermost plate (the first plate) of the distillation column 102, a mixed solution having the same composition as that of the raw material solution was introduced into the column at a rate of approximately 1.7 kg/Hr. Through the line 2, a mixed solution of urea and 4-(1,1,3,3-tetramethylbutyl)phenol (urea concentration: approximately 5 wt %) was fed to the column at a rate of approximately 1.3 kg/Hr. After operation conditions had been stabilized, the raw material solution was supplied through the line 1 at a rate of approximately 1.7 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 150° C. The thus obtained ingredient was recovered into a storage tank 104.

The reaction solution recovered in the storage tank 105 was analyzed by liquid chromatography and $^1$H-NMR. As a result, it was found that the reaction solution contained a 5,5'-carbonylbis(azanediyl)bis(2-methyl-5,1-phenylene)di(carbamic acid(4-(1,1,3,3-tetramethylbutyl)phenyl)ester), and that the yield of the 5,5'-carbonylbis(azanediyl)bis(2-methyl-5,1-phenylene)di(carbamic acid(4-(1,1,3,3-tetramethylbutyl) phenyl) ester) was approximately 90% based on 2,4-toluenediamine.

In addition, from the results of the after-mentioned Comparative Example 6, it was assumed that a compound having a urea bond was generated (the thermal dissociation temperature of the urea bond: 210° C.) in the production of an N-substituted carbamic acid ester in the present step. In the present example, as described above, on the 15$^{th}$ plate for supplying the mixed solution of urea and 4-(1,1,3,3-tetramethylbutyl) phenol, the compound having the urea bond reacted with urea under heating at a temperature equal to or higher than the thermal dissociation temperature of the urea bond (240° C.) to generate an N-substituted carbamic acid ester. Thus, it was considered that the N-substituted carbamic acid ester could be obtained at a high yield.

Comparative Example 6

Step (P-1)

The same method as that in the step (23-1) of Example 23 was carried out with the exception that the mixed solution of urea and 4-(1,1,3,3-tetramethylbutyl) phenol was not fed through the line 2.

The reaction solution recovered in the storage tank 105 was analyzed by liquid chromatography and $^1$H-NMR. As a result, it was found that the reaction solution contained a 4-methyl-1,3-phenylenedi(carbamic acid(4-(1,1,3,3-tetramethylbutyl)phenyl)ester), and that the yield of the 4-methyl-1,3-phenylenedi(carbamic acid(4-(1,1,3,3-tetramethylbutyl) phenyl)ester) was approximately 38% based on 2,4-toluenediamine. In addition, the reaction solution contained approximately 15% by mass of 5,5'-carbonylbis(azanediyl) bis(2-methyl-5,1-phenylene)di(carbamic acid (4-(1,1,3,3-tetramethylbutyl)phenyl)ester) as a compound having a urea bond. The thermal dissociation temperature of the urea bond of the 5,5'-carbonylbis(azanediyl)bis(2-methyl-5,1-phenylene)di(carbamic acid (4-(1,1,3,3-tetramethylbutyl) phenyl) ester) was 210° C.

Moreover, the reaction solution was collected from a sampling port equipped on the 15$^{th}$ plate of the distillation column during the steady operation, and it was then analyzed. As a result, urea was not detected. Furthermore, the reaction solution was collected from a sampling port equipped on the third plate of the distillation column, in which the temperature was less than the thermal dissociation temperature of the urea bond (210° C.), and it was then analyzed. As a result, urea was not detected.

Example 24

Step (24-1): Production of Compound Having Ureido Group

The apparatus shown in FIG. 6 was used.

In a state in which a line 66 was closed, 45.2 kg (205 mol) of 4-nonyl phenol was mixed with 3.3 kg (55.0 mol) of urea in a storage tank 601 that had been heated to 120° C., and the mixed solution was then transferred into an agitation tank 603 that had been heated to 120° C. In a state in which the mixed solution was stirred in the agitation tank 603, 1.4 kg of 2,4-toluenediamine was supplied from a storage tank 602 to the agitation tank 603, through a line 62, at a rate of approximately 2.5 kg/Hr. After completion of the supply of the 4,4'-methylenebis(cyclohexylamine), the mixture was stirred for approximately 4 hours, and the reaction solution was then sampled. The reaction solution was analyzed by liquid chromatography. As a result, 2,4-toluene diurea was generated at a yield of approximately 98% based on 2,4-toluenediamine.

Thereafter, the line 66 was opened, and the reaction solution was then transferred through the line 66 to a storage tank 606.

Step (24-2): Production of N-substituted Carbamic Acid Ester

The apparatus shown in FIG. 1 was used.

4-Nonyl phenol was added into a plate-type distillation column 102 having 40 plates, and it was then boiled with a reboiler 105, so that it could be in a total reflux state. At this time, the pressure of the column top was 2.5 kPa, and the temperature of the 15$^{th}$ plate (counted from the column top side) on which a line 2 was equipped was 250° C. Through a line 1 equipped on the uppermost plate (the first plate) of the distillation column 102, a mixed solution having the same composition as that of the reaction solution obtained in the step (28-1) was introduced into the column at a rate of approximately 2.0 kg/Hr. At the same time, through the line 2, a mixed solution of urea and 4-nonyl phenol (urea concentration: approximately 4.2 wt %) was fed to the column at a rate of approximately 1.1 kg/Hr. After operation conditions had been stabilized, the reaction solution obtained in the step (28-1) was supplied through the line 1 at a rate of approximately 2.0 kg/Hr, and the reaction solution was then recovered into a storage tank 105 through a line 6 equipped at the lowermost portion of the distillation column 102. A gaseous phase ingredient was recovered through a line 3 equipped at the uppermost portion of the distillation column 102, and it was then condensed using a condenser 103 that was retained at approximately 85° C. The thus obtained ingredient was recovered into a storage tank 104.

The reaction solution recovered in the storage tank 105 was analyzed by liquid chromatography and $^1$H-NMR. As a result, it was found that the reaction solution was a solution containing a 5,5'-carbonylbis(azanediyl)bis(2-methyl-5,1-phenylene)di(carbamic acid(4-nonylphenyl)ester), and that the yield of the 5,5'-carbonylbis(azanediyl)bis(2-methyl-5,1-phenylene)di(carbamic acid(4-nonylphenyl)ester) was approximately 89% based on 2,4-toluenediamine.

In addition, from the results of the after-mentioned Reference Example 10, it was assumed that a compound having a urea bond was generated (the thermal dissociation temperature of the urea bond: 210° C.) in the production of an N-substituted carbamic acid ester in the present step. In the present example, as described above, on the 15$^{th}$ plate for supplying the mixed solution of urea and 4-nonyl phenol, the compound having the urea bond reacted with urea under heating at a temperature equal to or higher than the thermal dissociation temperature of the urea bond (250° C.) to generate an N-substituted carbamic acid ester. Thus, it was considered that the N-substituted carbamic acid ester could be obtained at a high yield.

Reference Example 10

Step (Q-1)

The same method as that in the step (24-2) of Example 24 was carried out with the exception that the mixed solution of urea and 4-nonyl phenol was not fed through the line 2.

The reaction solution recovered in the storage tank 105 was analyzed by liquid chromatography and $^1$H-NMR. As a result, it was found that the reaction solution contained a 4-methyl-1,3-phenylenedi(carbamic acid(4-nonylphenyl)ester), and that the yield of the 4-methyl-1,3-phenylenedi(carbamic acid(4-nonylphenyl)ester) was approximately 38% based on 2,4-toluenediamine. In addition, the reaction solution contained approximately 15% by mass of 5,5'-carbonyl-bis(azanediyl)bis(2-methyl-5,1-phenylene)di(carbamic acid (4-nonyl)phenyl)ester) as a compound having a urea bond. The thermal dissociation temperature of the urea bond of the 5,5'-carbonylbis(azanediyl)bis(2-methyl-5,1-phenylene)di (carbamic acid(4-nonyl)phenyl)ester) was 207° C.

Moreover, the reaction solution was collected from a sampling port equipped on the 15$^{th}$ plate of the distillation column during the steady operation, and it was then analyzed. As a result, urea was not detected.

Example 25

Step (25-1)

The same method as that in the step (B-1) of Reference Example 2 was carried out with the exception that a mixed solution of phenyl carbamate and phenol (phenyl carbamate concentration: approximately 30 wt %) was fed through the line 2 at a rate of approximately 2.7 kg/Hr.

The reaction solution recovered in the storage tank 105 was analyzed by liquid chromatography and $^1$H-NMR. As a result, it was found that the reaction solution is a solution containing a 3-(phenoxycarbonylaminomethyl)-3,5,5-trimethylcyclohexyl carbamic acid phenyl ester, and that the yield of the 3-(phenoxycarbonylaminomethyl)-3,5,5-trimethylcyclohexyl carbamic acid phenyl ester was approximately 91% based on 3-aminomethyl-3,5,5-trimethylcyclohexylamine.

In addition, from the above described results of Reference Example 2, it was assumed that a compound having a urea bond was generated (the thermal dissociation temperature of the urea bond: 206° C.) in the production of an N-substituted carbamic acid ester in the present step. In the present example, on the 15$^{th}$ plate for supplying the mixed solution of phenyl carbamate and phenol, the compound having the urea bond reacted with urea under heating at a temperature equal to or higher than the thermal dissociation temperature of the urea bond (230° C.) to generate an N-substituted carbamic acid ester. Thus, it was considered that the N-substituted carbamic acid ester could be obtained at a high yield.

The present application is based on a Japanese patent application (Japanese Patent Application No. 2011-035184), filed on Feb. 21, 2011; the disclosure of which is hereby incorporated by reference.

DESCRIPTION OF REFERENCE NUMERALS (FIG. 1) 100, 101, 104, 105: storage tank; 102: plate-type distillation column; 103: condenser; 106: reboiler; 107: gas-liquid separator; 1, 2, 3, 4, 5, 6: line (FIG. 2) 201, 203, 207, 209: storage tank; 202: thin-film distillation apparatus; 204: distillation column; 205: condenser; 206: gas-liquid separator; 208: reboiler; 20, 21, 22, 23, 24, 25, 26: line (FIG. 3) 300, 301, 304, 305: storage tank; 302: plate-type distillation column; 303: condenser; 306: reboiler; 307: gas-liquid separator; 31, 32, 33, 34, 35, 36: line (FIG. 4) 400, 401, 404, 405: storage tank; 402: plate-type distillation column; 403: condenser; 406: reboiler; 407: gas-liquid separator; 40, 41, 42, 43, 44, 45, 46, 47, 48: line (FIG. 5) 500, 501, 504, 505: storage tank; 502: plate-type distillation column; 503: condenser; 506: reboiler; 507: gas-liquid separator; 50, 51, 52, 53, 54, 55, 56, 57: line (FIG. 6) 600, 601, 602, 604, 606: storage tank; 603: agitation tank; 605: gas-liquid separator; 607: condenser; 60, 61, 62, 63, 64, 65, 66: line (FIG. 7) 701, 704, 705: storage tank; 702: packed column; 703: condenser; 706: reboiler; 707: gas-liquid separator; 71, 72, 73, 74: line

The invention claimed is:

1. A method for producing a carbonyl compound, comprising a step (X) of reacting a compound having a urea moiety of a formula (1) as shown below with a carbonic acid derivative selected from the group consisting of a carbonic acid ester, an N-unsubstituted carbamic acid ester, urea, and phosgene under heating at a temperature equal to or higher than the thermal dissociation temperature of the nitrogen-carbonyl bond to obtain the carbonyl compound;

wherein the step (X) is carried out in a distillation column comprising a supply port A, a supply port B and a discharge port C, the step X comprising:

supplying raw material ingredients containing the compound having the urea moiety, or raw material ingredients containing a precursor of the compound having the urea moiety, to the distillation column via at least the supply port A, supplying the carbonic acid derivative to the distillation column via at least the supply port B, and recovering a generated mixture comprising the carbonyl compound via at least the discharge port C disposed at a lower part of the distillations column; and the supply port B is disposed at a position the same as or lower than the supply port A, the discharge port C is disposed at a position the same as or lower than the supply port B, and a temperature of the distillation column at a height of the supply port B is equal to or higher than the thermal dissociation temperature of the nitrogen-carbonyl bond in the compound having the urea moiety.

2. The method for producing the carbonyl compound according to claim 1, wherein the step (X) is carried out in the coexistence of a hydroxy compound.

3. The method for producing the carbonyl compound according to claim 1, wherein the carbonyl compound comprises an N-substituted carbamic acid ester.

4. The method for producing the carbonyl compound according to claim 1, wherein the carbonic acid derivative is urea or an N-unsubstituted carbamic acid ester.

5. The method for producing the carbonyl compound according to claim 1, wherein the carbonic acid derivative is a carbonic acid ester.

6. The method for producing the carbonyl compound according to claim 1, wherein the compound having the urea moiety is a compound of a formula (2) as shown below, which is produced from raw material ingredients comprising an organic primary amine and a carbonic acid derivative:

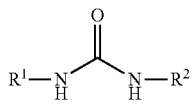

(2)

wherein
R¹ and R² are each independently an organic group comprising a group derived from the organic primary amine.

7. The method for producing the carbonyl compound according to claim 1, wherein the compound having the urea moiety is a polyurethane-urea copolymer.

8. The method for producing the carbonyl compound according to claim 1, wherein
the carbonic acid derivative is phosgene, and
the carbonyl compound comprises a group of the following formula (3):

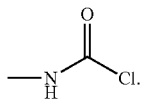

(3)

9. The method for producing the carbonyl compound according to claim 8, wherein the compound having the urea moiety is a compound produced from an organic primary amine and a phosgene.

10. The method for producing the carbonyl compound according to claim 3, further comprising a step of heating the carbonyl compound at a temperature in the range of 100° C. to 300° C. to prepare an isocyanate.

11. The method for producing the carbonyl compound according to claim 1, wherein the precursors of the compound having the urea moiety are an organic primary amine and a carbonic acid derivative.

12. The method for producing the carbonyl compound according to claim 1, wherein the precursor of the compound having the urea moiety is a compound having a ureido group of the following formula (4):

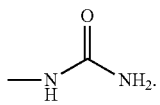

(4)

13. The method for producing the carbonyl compound according to claim 1, wherein the raw material ingredients to be supplied via the supply port A further contain a hydroxy compound.

14. The method for producing the carbonyl compound according to claim 1, wherein
the raw material ingredients to be supplied via the supply port A are a combination (i) or (ii) described below, and the mixture to be recovered via the discharge port C comprises an N-substituted carbamic acid ester and a hydroxy compound:
combination (i): an organic primary amine, urea, and a hydroxy compound; or
combination (ii): a hydroxy compound and a compound having a ureido group of by the following formula (4):

(4)

15. The method for producing the carbonyl compound according to claim 1, wherein
the raw material ingredients to be supplied via the supply port A are combination (iii): an organic primary amine, a carbonic acid ester, and a hydroxy compound, and
the mixture to be recovered via the discharge port C comprises an N-substituted carbamic acid ester and a hydroxy compound.

16. The method for producing the carbonyl compound according to claim 1, wherein
the raw material ingredients to be supplied via the supply port A are combination (iv): a polyurethane-urea copolymer and a hydroxy compound, and
the mixture to be recovered via the discharge port C comprises an N-substituted carbamic acid ester and a hydroxy compound.

17. The method for producing the carbonyl compound according to claim 1, wherein a hydroxy compound is further supplied to the distillation column via the supply port B.

18. The method for producing the carbonyl compound according to claim 1, wherein
the distillation column comprises a plurality of the supply ports B, and
a mixture of a carbonic acid derivative and a hydroxy compound is supplied to the distillation column via the plurality of supply ports B.

19. The method for producing the carbonyl compound according to claim 1, wherein
the distillation column further comprises a condenser;
the method further comprises a step of condensing a portion of gas discharged from a top of the distillation column using the condenser to obtain a condensate;
a hydroxy compound is further supplied to the distillation column via the supply port A and/or the supply port B;
the carbonic acid derivative to be supplied via the supply port B is urea and/or an N-unsubstituted carbamic acid ester;
the gas discharged from the top of the distillation column comprises a hydroxyl compound, ammonia, a compound having a carbonyl group derived from the carbonic acid derivative and/or a compound having a carbonyl group derived from the compound having the urea moiety; and
the condensate contains a compound having a carbonyl group and a hydroxy compound.

20. The method for producing the carbonyl compound according to claim 19, wherein a part of or an entire condensate is circulated inside the distillation column.

21. The method for producing the carbonyl compound according to claim 19, wherein a part of or an entire condensate is supplied to the distillation column via the supply port B.

22. The method for producing the carbonyl compound according to claim 19, wherein a part of or an entire condensate is recycled as a raw material ingredient for producing a compound having a ureido group of the following formula (4):

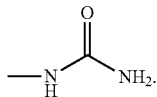  (4)

23. The method for producing the carbonyl compound according to claim 19, further comprising a step of reacting the ammonia contained in the gas discharged from the top of the distillation column with carbon dioxide to produce urea, the urea being recycled back to the distillation column.

24. The method for producing the carbonyl compound according to claim 6, wherein the organic primary amine is a compound of the following formula (5):

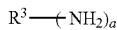  (5)

wherein
  $R^3$ ia an organic group containing 1 to 85 carbon atoms, and
  a is an integer from 1 to 10.

25. The method for producing the carbonyl compound according to claim 2, wherein
  the hydroxy compound is an aromatic hydroxy compound, and
  the carbonyl compound comprises an N-substituted carbamic acid-O-aryl aster of the following formula (6):

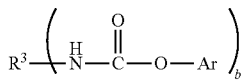  (6)

wherein
  $R^3$ is an organic group containing 1 to 85 carbon atoms,
  Ar is a group derived from an aromatic hydroxy compound, which is a residue obtained by removing one hydroxy group from the aromatic hydroxy compound, and
  b is an integer from 1 to 10.

26. The method for producing the carbonyl compound according to claim 2, wherein
  the hydroxy compound is an alcohol, and
  the carbonyl compound comprises an N-substituted carbamic acid-O-alkyl ester of by the following formula (7):

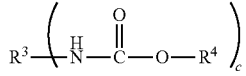  (7)

wherein
  $R^3$ is an organic group containing 1 to 85 carbon atoms,
  $R^4$ is a group derived from an alcohol, which is a residue obtained by removing one hydroxy group from the alcohol, and c is an integer from 1 to 10.

27. The method for producing the carbonyl compound according to claim 26, further comprising a step of reacting the N-substituted carbamic acid-O-alkyl ester with an aromatic hydroxy compound to obtain an N-substituted carbamic acid-O-ary ester of the following formula (6) and an alcohol:

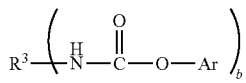  (6)

wherein
  $R^3$ is an organic group containing 1 to 85 carbon atoms,
  Ar is a group derived from an aromatic hydroxy compound, which is a residue obtained by removing one hydroxy group from the aromatic hydroxy compound, and
  b is an integer from 1 to 10.

28. The method for producing the carbonyl compound according to claim 25, further comprising heating the N-substituted carbamic acid-O-aryl ester at a temperature in the range of 100° C. to 300° C. to provide a product comprising an isocyanate and an aromatic hydroxy compound; and
  separating the product into a gaseous phase ingredient and a liquid phase ingredient and then recovering a part of or an entire liquid phase ingredient, wherein
  the liquid phase ingredient contains a compound having a urea moiety.

29. The method for producing the carbonyl compound according to claim 11, wherein the organic primary amine is a compound of the following formula (5):

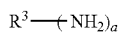  (5)

wherein
  $R^3$ is an organic group containing 1 to 85 carbon atoms, and
  a represents is an integer front 1 to 10.

* * * * *